US012629253B2

(12) United States Patent
Webb et al.

(10) Patent No.: US 12,629,253 B2
(45) Date of Patent: May 19, 2026

(54) ORTHOPAEDIC KNEE CONE COMPONENTS FOR USE IN AN ORTHOPAEDIC SURGICAL PROCEDURE AND INSTRUMENTS AND METHODS FOR INSTALLING THE SAME

(71) Applicant: DEPUY IRELAND UNLIMITED COMPANY, Ringaskiddy (IE)

(72) Inventors: Anthony J. Webb, Fort Wayne, IN (US); Lindsay L. Gilson, Columbia City, IN (US); Jeremiah M. Lewis, Warsaw, IN (US); Matthew D. Schmit, Columbia City, IN (US); Wesley J. Gardner, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 1142 days.

(21) Appl. No.: 17/665,030

(22) Filed: Feb. 4, 2022

(65) Prior Publication Data

US 2023/0190478 A1 Jun. 22, 2023

Related U.S. Application Data

(63) Continuation-in-part of application No. 17/557,635, filed on Dec. 21, 2021, and a continuation-in-part of
(Continued)

(51) Int. Cl.
| | |
|---|---|
| *A61F 2/30* | (2006.01) |
| *A61F 2/38* | (2006.01) |
| *A61F 2/46* | (2006.01) |

(52) U.S. Cl.
CPC ........ *A61F 2/30734* (2013.01); *A61F 2/3859* (2013.01); *A61F 2/4684* (2013.01);
(Continued)

(58) Field of Classification Search
CPC ................ A61F 2/3859; A61F 2/30734; A61F 2002/30736; A61F 2/389
See application file for complete search history.

(56) References Cited

U.S. PATENT DOCUMENTS

| | | | |
|---|---|---|---|
| 2,947,308 | A | 8/1960 | Gorman |
| D230,429 | S | 2/1974 | Davidson et al. |
| (Continued) | | | |

FOREIGN PATENT DOCUMENTS

| | | |
|---|---|---|
| DE | 7716147 U1 | 10/1977 |
| EP | 532585 B1 | 4/2000 |
| (Continued) | | |

OTHER PUBLICATIONS

Exactech Knee Operative Technique Addendum, Optetrak Logic® Metaphyseal Cones, 2016, 20 pages.
(Continued)

*Primary Examiner* — Christopher D. Prone
(74) *Attorney, Agent, or Firm* — Barnes & Thornburg LLP

(57) ABSTRACT

An orthopaedic joint replacement system is shown and described. The system includes a number of prosthetic components configured to be implanted into a patient's knee. The system also includes a number of surgical instruments configured for use in preparing the bones of the patient's knee to receive the implants. A number of methods for using the surgical instruments to prepare the bones is also disclosed.

11 Claims, 47 Drawing Sheets

Related U.S. Application Data application No. 17/557,629, filed on Dec. 21, 2021, now Pat. No. 12,115,084, and a continuation-in-part of application No. 17/557,620, filed on Dec. 21, 2021, now Pat. No. 12,478,477.

(52) U.S. Cl.
  CPC .............. *A61F 2002/30205* (2013.01); *A61F 2002/30736* (2013.01)

(56) References Cited

U.S. PATENT DOCUMENTS

| | | | |
|---|---|---|---|
| 3,891,997 A | 7/1975 | Herbert |
| 4,136,405 A | 1/1979 | Pastrick et al. |
| 4,164,794 A | 8/1979 | Spector et al. |
| 4,206,516 A | 6/1980 | Pilliar |
| 4,216,549 A | 8/1980 | Hillberry et al. |
| 4,219,893 A | 9/1980 | Noiles |
| 4,224,696 A | 9/1980 | Murray et al. |
| 4,523,587 A | 6/1985 | Frey |
| 4,659,331 A | 4/1987 | Matthews et al. |
| 4,711,639 A | 12/1987 | Grundei |
| 4,790,852 A | 12/1988 | Noiles |
| 4,822,366 A | 4/1989 | Bolesky |
| 4,827,919 A | 5/1989 | Barbarito et al. |
| 4,883,488 A | 11/1989 | Bloebaum et al. |
| 4,888,021 A | 12/1989 | Forte et al. |
| 4,944,757 A | 7/1990 | Martinez et al. |
| 4,950,298 A | 8/1990 | Gustilo et al. |
| 5,019,103 A | 5/1991 | Van Zile et al. |
| 5,059,196 A | 10/1991 | Coates |
| 5,152,797 A | 10/1992 | Luckman et al. |
| 5,197,488 A | 3/1993 | Kovacevic |
| 5,226,915 A | 7/1993 | Bertin |
| 5,246,459 A | 9/1993 | Elias |
| 5,356,414 A | 10/1994 | Cohen et al. |
| 5,358,527 A | 10/1994 | Forte |
| 5,358,530 A | 10/1994 | Hodorek |
| 5,370,693 A | 12/1994 | Kelman et al. |
| 5,387,241 A | 2/1995 | Hayes |
| 5,413,604 A | 5/1995 | Hodge |
| 5,480,445 A | 1/1996 | Burkinshaw |
| 5,489,311 A | 2/1996 | Cipolletti |
| 5,549,685 A | 8/1996 | Hayes |
| 5,609,645 A | 3/1997 | Vinciguerra |
| 5,658,349 A | 8/1997 | Brooks et al. |
| 5,766,256 A | 6/1998 | Oudard et al. |
| 5,782,925 A | 7/1998 | Collazo et al. |
| 5,824,103 A | 10/1998 | Williams |
| 5,951,564 A | 9/1999 | Schroder et al. |
| 5,957,979 A | 9/1999 | Beckman et al. |
| 5,984,968 A | 11/1999 | Park |
| 5,997,581 A | 12/1999 | Khalili |
| 6,039,764 A | 3/2000 | Pottenger et al. |
| 6,071,311 A | 6/2000 | O'Neil et al. |
| 6,074,424 A | 6/2000 | Perrone, Jr. et al. |
| 6,080,195 A | 6/2000 | Colleran et al. |
| 6,117,175 A | 9/2000 | Bosredon |
| 6,126,691 A | 10/2000 | Kasra et al. |
| 6,139,581 A | 10/2000 | Engh et al. |
| 6,139,584 A | 10/2000 | Ochoa et al. |
| 6,152,963 A | 11/2000 | Noiles et al. |
| 6,162,254 A | 12/2000 | Timoteo |
| 6,171,342 B1 | 1/2001 | O'Neil et al. |
| 6,264,699 B1 | 7/2001 | Noiles et al. |
| 6,423,096 B1 | 7/2002 | Musset et al. |
| 6,428,578 B2 | 8/2002 | White |
| 6,447,549 B1 | 9/2002 | Taft |
| 6,613,092 B1 | 9/2003 | Kana et al. |
| 7,105,026 B2 | 9/2006 | Johnson et al. |
| 7,208,222 B2 | 4/2007 | Rolfe et al. |
| 7,291,174 B2 | 11/2007 | German et al. |
| 7,846,212 B2 | 12/2010 | Lewis et al. |
| 7,892,288 B2 | 2/2011 | Blaylock et al. |
| 8,382,849 B2 | 2/2013 | Thomas |
| 8,721,733 B2 | 5/2014 | Bonitati |
| 8,900,317 B2 | 12/2014 | Zubok et al. |
| 8,998,996 B2 | 4/2015 | James et al. |
| 9,011,444 B2 | 4/2015 | Primiano et al. |
| 9,149,282 B2 | 10/2015 | Servidio et al. |
| 9,526,513 B2 | 12/2016 | Collazo et al. |
| 9,668,758 B2 | 6/2017 | Collazo et al. |
| 10,085,841 B2 | 10/2018 | Blaylock et al. |
| 10,524,806 B2 | 1/2020 | Collazo et al. |
| 10,893,947 B2 | 1/2021 | Blaylock et al. |
| 2002/0072802 A1 | 6/2002 | O'Neil et al. |
| 2003/0171815 A1 | 9/2003 | Kana et al. |
| 2004/0049270 A1 | 3/2004 | Gewirtz |
| 2004/0049284 A1 | 3/2004 | German et al. |
| 2004/0117024 A1 | 6/2004 | Gerbec et al. |
| 2004/0162619 A1 | 8/2004 | Blaylock et al. |
| 2005/0107883 A1 | 5/2005 | Goodfried et al. |
| 2007/0088443 A1 | 4/2007 | Hanssen et al. |
| 2008/0167722 A1 | 7/2008 | Metzger et al. |
| 2008/0281430 A1 | 11/2008 | Kelman et al. |
| 2010/0114323 A1 | 5/2010 | Deruntz et al. |
| 2013/0172892 A1* | 7/2013 | Servidio ............ A61B 17/1675 623/18.11 |
| 2013/0178947 A1 | 7/2013 | Monaghan et al. |
| 2014/0257293 A1 | 9/2014 | Axelson, Jr. et al. |
| 2014/0277528 A1 | 9/2014 | Mines et al. |
| 2018/0008416 A1 | 1/2018 | Vergari et al. |

FOREIGN PATENT DOCUMENTS

| | | |
|---|---|---|
| EP | 863731 B1 | 4/2001 |
| EP | 2540255 A1 | 1/2013 |
| EP | 2668932 A1 | 12/2013 |
| JP | 10277069 A | 10/1998 |
| JP | 2001526573 A | 12/2001 |
| WO | 9118563 A1 | 12/1991 |
| WO | 9718776 A1 | 5/1997 |
| WO | 9730661 A1 | 8/1997 |
| WO | 9852499 A1 | 11/1998 |
| WO | 9932053 A1 | 7/1999 |
| WO | 0205732 A1 | 1/2002 |
| WO | 2009089581 A1 | 7/2009 |
| WO | 2015145348 A1 | 10/2015 |

OTHER PUBLICATIONS

Zimmer Biomet, Persona Revision Knee System, Surgical Technique, 2019, 72 pages.

Zimmer Biomet, Persona Revision Knee System, Large Defect Surgical Technique, 2019, 14 pages.

Zimmer Biomet, Trabecular Metal Tibial and Femoral Cones, Surgical Technique, 2020, 64 pages.

Stryker, Triathlon Revision Knee System, Surgical Protocol, 2016, 92 pages.

PCT International Search Report for International Application No. PCT/EP2022/087016; Mar. 16, 2023; 24 pages.

* cited by examiner

308

300

322

302

304

158

150

114

10

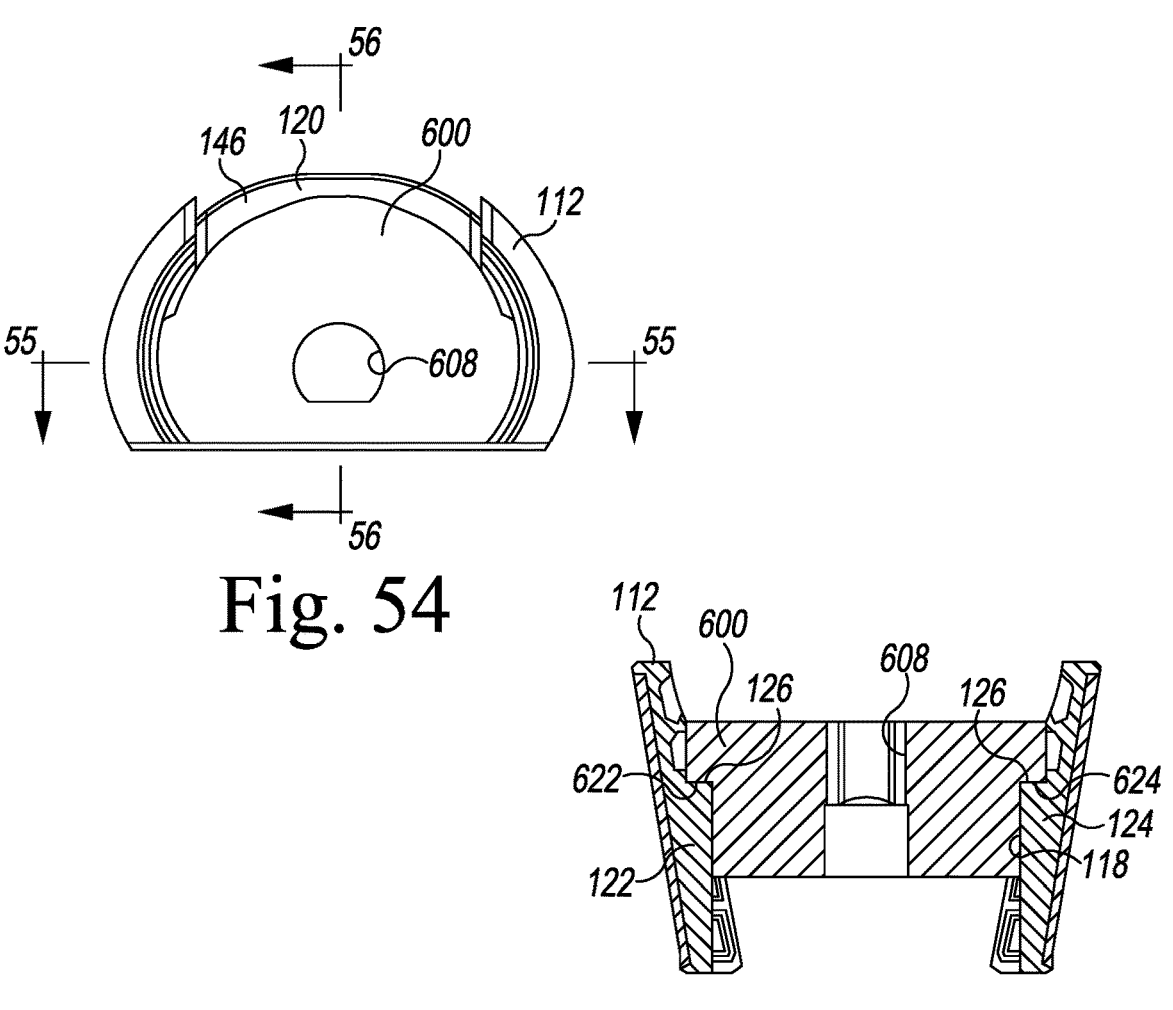
Fig. 54
Fig. 55
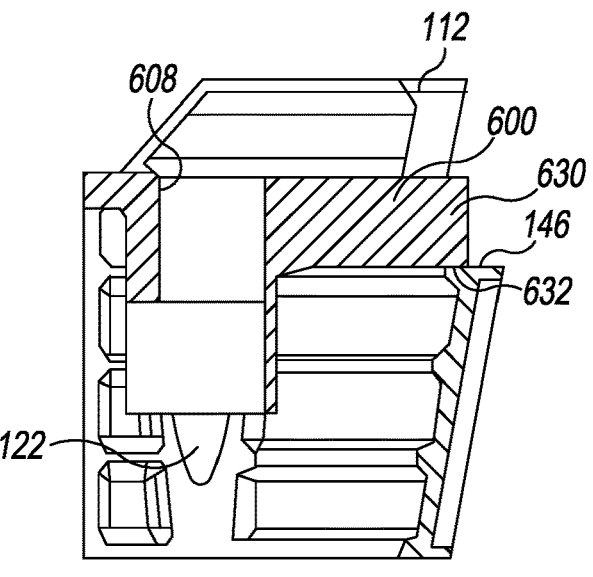
Fig. 56

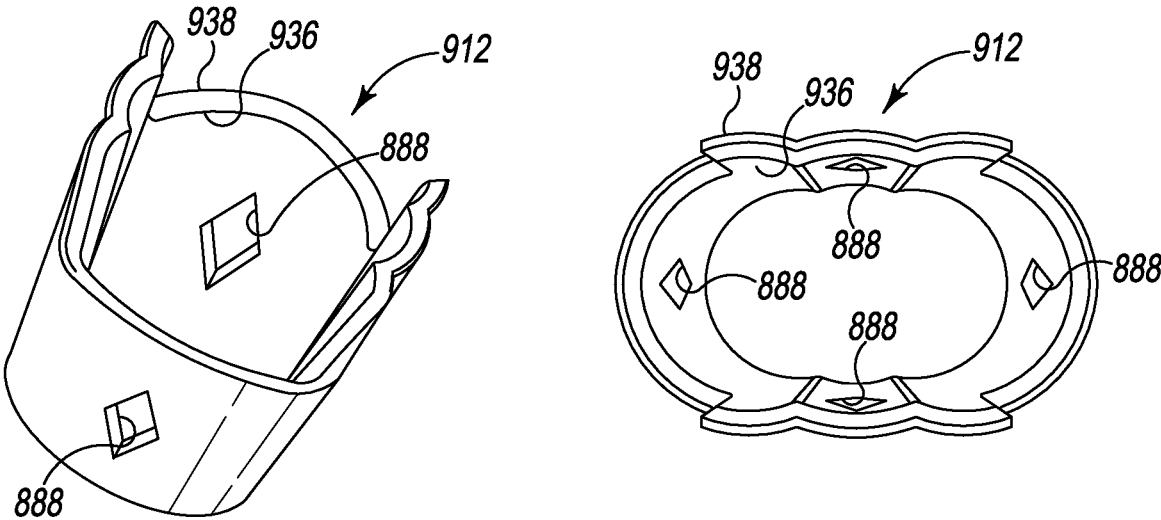
Fig. 80
Fig. 81
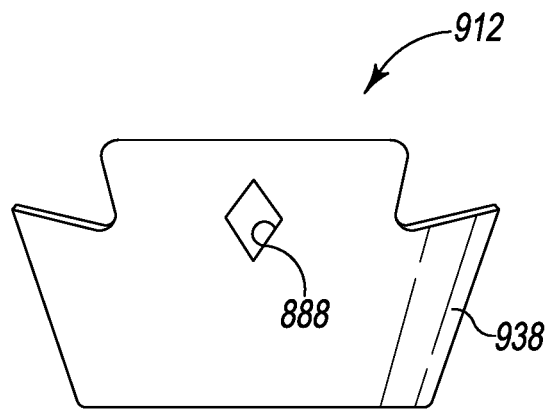
Fig. 82

ORTHOPAEDIC KNEE CONE COMPONENTS FOR USE IN AN ORTHOPAEDIC SURGICAL PROCEDURE AND INSTRUMENTS AND METHODS FOR INSTALLING THE SAME

This continuation-in-part application claims priority to each of U.S. patent application Ser. No. 17/557,620 entitled "MODULAR TIBIAL CONE AUGMENTS AND METHOD OF SURGICALLY USING THE SAME;" U.S. patent application Ser. No. 17/557,629, now U.S. Pat. No. 12,115,084, entitled "METHOD OF INSTALLING A KNEE CONE AUGMENT IN AN ORTHOPAEDIC SURGICAL PROCEDURE;" and U.S. patent application Ser. No. 17/557,635 entitled "KNEE CONE AUGMENTS AND ASSOCIATED SURGICAL BROACHES FOR USE IN AN ORTHOPAEDIC SURGICAL PROCEDURE;" each of which was filed on Dec. 21, 2021, each of which is assigned to the same assignee as the present application, and each of which is hereby incorporated by reference.

CROSS-REFERENCE TO RELATED APPLICATIONS

Cross reference is made to U.S. patent application Ser. No. 17/665,045 entitled "ORTHOPAEDIC SURGICAL SYSTEM FOR INSTALLING A KNEE CONE AUGMENT AND METHOD OF USING THE SAME;" and U.S. patent application Ser. No. 17/665,048 entitled "TRIAL EXTRACTOR OF AN ORTHOPAEDIC SURGICAL SYSTEM AND METHOD OF USING THE SAME;" each of which is assigned to the same assignee as the present application, each of which is filed concurrently herewith, and each of which is hereby incorporated by reference.

TECHNICAL FIELD

The present disclosure relates generally to an orthopaedic system, including prosthetic components, surgical instruments, and methods for use in the performance of an orthopaedic joint replacement procedure, and more particularly to orthopaedic prosthetic components, surgical instruments, and methods for use in the performance of a knee replacement procedure.

BACKGROUND

Joint arthroplasty is a well-known surgical procedure by which a diseased and/or damaged natural joint is replaced by a prosthetic joint. For example, in a knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared intramedullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis, commonly referred to a "primary knee prosthesis," is surgically removed and a replacement or "revision knee prosthesis" is implanted. In some revision knee surgeries, all of the components of the primary knee prosthesis, including, for example, the tibial tray, the femoral component, and the polymer bearing, may be surgically removed and replaced with revision prosthetic components.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis. Other orthopaedic surgical instruments such as trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, and a stem trial component that may be used to size and select a prosthetic stem component.

Moreover, during a revision knee surgery, the orthopaedic surgeon may use an augment in combination with the revision tibial tray and/or the revision femoral component to compensate for bone loss associated with removal of the primary knee prosthesis or other defects in the patient's tibia and/or femur. There are two types of commonly used knee augments—sleeve augments and cone augments. A sleeve augment is mechanically locked to one or more of the components of the revision knee prosthesis prior to implantation of the prosthesis into the patient's bone. For example, a tibial sleeve augment is mechanically locked (e.g., via a taper lock or fastener) to the tibial stem component and/or the tibial tray prior to implantation of the tibial revision prosthesis into the tibia of the patient, whereas a femoral sleeve augment is mechanically locked (e.g., via a taper lock or fastener) to the femoral stem component and/or the femoral component prior to implantation of the femoral revision prosthesis into the femoral of the patient. Cone augments, on the other hand, are not directly locked to the revision knee prosthesis prior to implantation of the prosthesis in the bone of the patient. Instead, a cone augment is first separately implanted into the bone of the patient. Thereafter, the revision knee prosthesis is then implanted into the bone of the patient through the implanted cone augment. Then, the implanted revision knee prosthesis may be secured to the previously-implanted cone augment by use of, for example, bone cement. In the case of a press-fit "cementless" revision knee prosthesis, the implanted prosthesis is not cemented or otherwise secured to the previously-implanted cone augment. For example, a tibial cone augment is first separately implanted in the tibia of a patient, with a tibial revision prosthesis then being implanted such that its tibial stem component extends through the tibial cone augment. Subsequent to implantation of the tibial revision prosthesis, bone cement may be used to secure the tibial stem component and the tibial tray to the tibial cone augment (although use of bone cement may be omitted in the case of use of a cementless tibial revision prosthesis). Similarly, in the case of a femoral procedure, a femoral cone augment is first separately implanted in the femur of a patient, with a femoral revision prosthesis then being implanted such that its femoral stem component extends through the femoral cone augment. Subsequent to implantation of the femoral revision prosthesis, bone cement may be used to secure the femoral stem component and the femoral component to the femoral cone augment (although use of bone cement may be omitted in the case of use of a cementless femoral revision prosthesis).

SUMMARY

An orthopaedic joint replacement system is shown and described. The system includes a number of prosthetic components configured to be implanted into a patient's knee. The system also includes a number of surgical instruments configured for use in preparing the bones of the patient's knee to receive the implants. Methods or techniques for using the surgical instruments to prepare the patient's bones are also disclosed.

According to one aspect of the disclosure, a method of surgically preparing a proximal end of a tibia of a patient includes reaming an intramedullary canal of the tibia with a canal reamer. The method also includes attaching a proximal end of a stem trial component to a distal end of a surgical broach, and thereafter advancing a distal end of the stem trial component within the reamed intramedullary canal of the tibia. The method also includes broaching the proximal end of the tibia using the surgical broach secured to the stem trial component during advancement of the distal end of the stem trial component within the reamed intramedullary canal of the tibia so as to form a surgically-prepared broached cavity in the proximal end of the tibia. A tibial cone augment is then installed in the broached cavity formed in the proximal end of the tibia.

In an embodiment, the proximal end of the tibia may be reamed using a cone reamer secured to the stem trial component so as to form a surgically-prepared reamed cavity in the proximal end of the tibia prior to broaching the proximal end of the tibia. In such an embodiment, the surgical broach is advanced into the reamed cavity formed in the proximal end of the tibia during advancement of the distal end of the stem trial component within the reamed intramedullary canal of the tibia so as to form the surgically-prepared broached cavity in the proximal end of the tibia.

In an embodiment, the stem trial component guides advancement of the surgical broach during broaching of the proximal end of the tibia.

The canal reamer is removed from the intramedullary canal prior to advancement of the distal end of the stem trial component within the reamed intramedullary canal.

The method also includes removing a previously-installed tibial implant from the tibia of the patient prior to reaming the intramedullary canal of the tibia with the canal reamer.

According to another aspect of the disclosure, a method of surgically preparing a distal end of a femur of a patient includes reaming an intramedullary canal of the femur with a canal reamer. The method also includes attaching a proximal end of a stem trial component to a distal end of a surgical broach, and thereafter advancing a distal end of the stem trial component within the reamed intramedullary canal of the femur. The method also includes broaching the distal end of the femur using the surgical broach secured to the stem trial component during advancement of the distal end of the stem trial component within the reamed intramedullary canal of the femur so as to form a surgically-prepared broached cavity in the distal end of the femur. A femoral cone augment is then installed in the broached cavity formed in the distal end of the femur.

In an embodiment, the distal end of the femur may be reamed using a cone reamer secured to the stem trial component so as to form a surgically-prepared reamed cavity in the distal end of the femur prior to broaching the distal end of the femur. In such an embodiment, the surgical broach is advanced into the reamed cavity formed in the distal end of the femur during advancement of the distal end of the stem trial component within the reamed intramedullary canal of the femur so as to form the surgically-prepared broached cavity in the distal end of the femur.

In an embodiment, the stem trial component guides advancement of the surgical broach during broaching of the distal end of the femur.

The canal reamer is removed from the intramedullary canal prior to advancement of the distal end of the stem trial component within the reamed intramedullary canal.

The method also includes removing a previously-installed femoral implant from the femur of the patient prior to reaming the intramedullary canal of the femur with the canal reamer.

According to yet another aspect of the disclosure, a method of surgically preparing a knee of a patient includes reaming an intramedullary canal of a tibia of the patient with a tibial canal reamer, and thereafter broaching a proximal end of the tibia using a surgical broach secured to a stem trial component positioned in the reamed intramedullary canal of the tibia so as to form a surgically-prepared broached cavity in the proximal end of the tibia. A tibial cone augment is then installed in the broached cavity formed in the proximal end of the tibia.

In an embodiment, the proximal end of the tibia is reamed using a cone reamer secured to the stem trial component positioned in the reamed intramedullary canal of the tibia so as to form a surgically-prepared reamed cavity in the proximal end of the tibia prior to broaching the proximal end of the tibia. In such an embodiment, the surgical broach is advanced into the reamed cavity formed in the proximal end of the tibia.

In an embodiment, the stem trial component guides advancement of the surgical broach during broaching of the proximal end of the tibia.

The canal reamer is removed from the intramedullary canal prior to advancement of the distal end of the stem trial component within the reamed intramedullary canal.

The method also includes removing a previously-installed tibial implant from the tibia of the patient prior to reaming the intramedullary canal of the tibia with the canal reamer.

According to a further aspect of the disclosure, a method of surgically preparing a knee of a patient includes reaming an intramedullary canal of a femur of the patient with a femoral canal reamer, and thereafter broaching a distal end of the femur using a surgical broach secured to a stem trial component positioned in the reamed intramedullary canal of the femur so as to form a surgically-prepared broached cavity in the distal end of the femur. A femoral cone augment is then installed in the broached cavity formed in the distal end of the femur.

In an embodiment, the distal end of the femur is reamed using a cone reamer secured to the stem trial component positioned in the reamed intramedullary canal of the femur so as to form a surgically-prepared reamed cavity in the distal end of the femur prior to broaching the distal end of the femur. In such an embodiment, the surgical broach is advanced into the reamed cavity formed in the distal end of the femur.

In an embodiment, the stem trial component guides advancement of the surgical broach during broaching of the distal end of the femur.

The canal reamer is removed from the intramedullary canal prior to advancement of the distal end of the stem trial component within the reamed intramedullary canal.

The method also includes removing a previously-installed femoral implant from the femur of the patient prior to reaming the intramedullary canal of the femur with the canal reamer.

According to another aspect of the disclosure, an orthopaedic system includes a plurality of tibial cone augments configured to be implanted into a surgically-prepared cavity in a proximal end of a tibia of a patient. Each of the plurality of tibial cone augments has (i) a medial/lateral augment taper angle that is the same as each of the other of the plurality of tibial cone augments, and (ii) a medial/lateral augment width that is different from each of the other of the plurality of tibial cone augments. The orthopaedic system also includes a plurality of tibial surgical broaches having cutting teeth configured to cut and remove bone to form the surgically-prepared cavity in the proximal end of the tibia of the patient. Each of the plurality of tibial surgical broaches has (i) a medial/lateral broach taper angle that is the same as each of the other of the plurality of tibial surgical broaches, the medial/lateral broach taper angle being the same as the medial/lateral augment taper angle, and (ii) a medial/lateral broach width that is different from each of the other of the plurality of tibial surgical broaches.

In an embodiment, each of the plurality of tibial cone augments has an anterior/posterior augment taper angle that is the same as each of the other of the plurality of tibial cone augments, and each of the plurality of tibial surgical broaches has an anterior/posterior broach taper angle that is the same as each of the other of the plurality of tibial surgical broaches, with the anterior/posterior broach taper angle being the same as the anterior/posterior augment taper angle.

In an illustrative embodiment, each of the plurality of tibial cone augments is embodied as a tri-lobe tibial cone augment. In another embodiment, each of the plurality of tibial cone augments is embodied as a bi-lobe tibial cone augment.

The orthopaedic system may also include a stem trial component having a threaded post extending from a proximal end thereof. In such an embodiment, each of the plurality of tibial surgical broaches has a threaded aperture formed in a distal end thereof that is sized to threadingly receive the threaded post of the stem trial component.

According to a further aspect, an orthopaedic system includes a plurality of femoral cone augments configured to be implanted into a surgically-prepared cavity in a distal end of a femur of a patient. Each of the plurality of femoral cone augments has (i) a medial/lateral augment taper angle that is the same as each of the other of the plurality of femoral cone augments, and (ii) a medial/lateral augment width that is different from each of the other of the plurality of femoral cone augments. The orthopaedic system also includes a plurality of femoral surgical broaches having cutting teeth configured to cut and remove bone to form the surgically-prepared cavity in the distal end of the femur of the patient. Each of the plurality of femoral surgical broaches has (i) a medial/lateral broach taper angle that is the same as each of the other of the plurality of femoral surgical broaches, the medial/lateral broach taper angle being the same as the medial/lateral augment taper angle, and (ii) a medial/lateral broach width that is different from each of the other of the plurality of femoral surgical broaches.

In an embodiment, each of the plurality of femoral cone augments has an anterior/posterior augment taper angle that is the same as each of the other of the plurality of femoral cone augments, and each of the plurality of femoral surgical broaches has an anterior/posterior broach taper angle that is the same as each of the other of the plurality of femoral surgical broaches, with the anterior/posterior broach taper angle being the same as the anterior/posterior augment taper angle.

The orthopaedic system may also include a stem trial component having a threaded post extending from a proximal end thereof. In such an embodiment, each of the plurality of femoral surgical broaches has a threaded aperture formed in a distal end thereof that is sized to threadingly receive the threaded post of the stem trial component.

According to yet another aspect of the disclosure, an orthopaedic system includes a plurality of knee cone augments configured to be implanted into a surgically-prepared cavity in an end of a bone of a patient's knee. Each of the plurality of knee cone augments has (i) a medial/lateral augment taper angle that is the same as each of the other of the plurality of knee cone augments, and (ii) a medial/lateral augment width that is different from each of the other of the plurality of knee cone augments. The orthopaedic system also includes a plurality of knee surgical broaches having cutting teeth configured to cut and remove bone to form the surgically-prepared cavity in the end of the bone of the patient's knee. Each of the plurality of knee surgical broaches has (i) a medial/lateral broach taper angle that is the same as each of the other of the plurality of knee surgical broaches, the medial/lateral broach taper angle being the same as the medial/lateral augment taper angle, and (ii) a medial/lateral broach width that is different from each of the other of the plurality of knee surgical broaches.

In an embodiment, each of the plurality of knee cone augments has an anterior/posterior augment taper angle that is the same as each of the other of the plurality of knee cone augments, and each of the plurality of knee surgical broaches has an anterior/posterior broach taper angle that is the same as each of the other of the plurality of knee surgical broaches, with the anterior/posterior broach taper angle being the same as the anterior/posterior augment taper angle.

In an illustrative embodiment, each of the plurality of knee cone augments is embodied as a tri-lobe tibial cone augment. In another embodiment, each of the plurality of knee cone augments is embodied as a bi-lobe tibial cone augment. In yet another illustrative embodiment, each of the plurality of knee cone augments is embodied as a femoral cone augment.

The orthopaedic system may also include a stem trial component having a threaded post extending from a proximal end thereof. In such an embodiment, each of the plurality of knee surgical broaches has a threaded aperture formed in a distal end thereof that is sized to threadingly receive the threaded post of the stem trial component.

According to a further aspect of the disclosure, a method of surgically preparing an end of a bone of a patient's knee includes selecting a knee surgical broach having cutting teeth configured to cut bone from a plurality of knee surgical broaches, wherein the selected knee surgical broach has a medial/lateral broach taper angle that is the same as each of the other of the plurality of knee surgical broaches. The selected broach is then advanced into the end of the bone of the patient's knee so as to form a surgically-prepared cavity therein. A knee cone augment is then selected from a plurality of knee cone augments. The selected knee cone augment has (i) a medial/lateral augment taper angle that is the same as the medial/lateral broach taper angle, and (ii) a medial/lateral augment width that is smaller than a medial/lateral broach width of the selected knee surgical broach. Thereafter, the selected knee cone augment is implanted into the surgically-prepared cavity formed in the end of the bone of the patient's knee.

In one embodiment, the selected knee cone augment is a tibial cone augment that is implanted in a proximal end of a tibia of the patient's knee. In another embodiment, the selected knee cone augment is a tri-lobe tibial cone augment that is implanted in a proximal end of a tibia of the patient's knee. In yet another embodiment, the selected knee cone augment is a bi-lobe tibial cone augment that is implanted in a proximal end of a tibia of the patient's knee. In a further embodiment, the selected knee cone augment is a femoral cone augment that is implanted in a distal end of a femur of the patient's knee.

According to another aspect of the disclosure, an orthopaedic knee implant includes a modular tibial cone augment configured to be implanted into a surgically-prepared cavity in a proximal end of a tibia of a patient. The modular tibial cone augment includes a central lobe component having: (i) a round elongated body, (ii) a bore configured to receive a stem of a revision tibial prosthesis extending through the elongated body, (iii) a medial connector formed in a medial side of the elongated body, and (iv) a lateral connector formed in a lateral side of the elongated body. The modular tibial cone augment also includes a medial lobe component having: (i) a body having a curved medial outer surface that tapers from a superior end to an inferior end thereof, (ii) a curved inner sidewall that corresponds in shape to the medial side of the elongated body of the central lobe component, and (iii) a medial connector formed in the curved inner sidewall which mates with the medial connector of the central lobe component so as to selectively lock the medial lobe component to the central lobe component. The modular tibial cone augment further includes a lateral lobe component having: (i) a body having a curved lateral outer surface that tapers from a superior end to an inferior end thereof, (ii) a curved inner sidewall that corresponds in shape to the lateral side of the elongated body of the central lobe component, and (iii) a lateral connector formed in the curved inner sidewall which mates with the lateral connector of the central lobe component so as to selectively lock the lateral lobe component to the central lobe component.

In an embodiment, the medial connector of the central lobe component and the medial connector of the medial lobe component define a dovetail joint. In a similar embodiment, the lateral connector of the central lobe component and the lateral connector of the lateral lobe component also define a dovetail joint.

In another embodiment, the medial connector of the central lobe component is embodied as a tapered slot formed in an outer surface of the elongated body, with the medial connector of the medial lobe component being embodied as a tapered tab extending outwardly from the curved inner sidewall. The tapered tab of the medial lobe component is configured to be received into the tapered slot of the central lobe component so as to selectively lock the medial lobe component to the central lobe component.

In another embodiment, the lateral connector of the central lobe component is embodied as a tapered slot formed in an outer surface of the elongated body, with the lateral connector of the lateral lobe component being embodied as a tapered tab extending outwardly from the curved inner sidewall. The tapered tab of the lateral lobe component is configured to be received into the tapered slot of the central lobe component so as to selectively lock the lateral lobe component to the central lobe component.

In an embodiment, a porous-metal coating is disposed on the outer surfaces of central lobe component, the medial lobe component, and the lateral lobe component.

The bore of the central lobe component is defined by a conically-shaped sidewall extending through the elongated body of the central lobe component, and the conically-shaped sidewall may have a number cement pockets formed therein.

According to another aspect of the disclosure, an orthopaedic knee implant includes a modular tibial cone augment configured to be implanted into a surgically-prepared cavity in a proximal end of a tibia of a patient. The modular tibial cone augment includes a central lobe component having: (i) a round elongated body, (ii) a bore configured to receive a stem of a revision tibial prosthesis extending through the elongated body, and (iii) a connector formed in a side of the elongated body. The modular tibial cone augment also includes a side lobe component having: (i) a body having a curved outer surface that tapers from a superior end to an inferior end thereof, (ii) a curved inner sidewall that corresponds in shape to the side of the elongated body of the central lobe component, and (iii) a connector formed in the curved inner sidewall which mates with the connector of the central lobe component so as to selectively lock the side lobe component to the central lobe component.

In an embodiment, the connector of the central lobe component and the connector of the side lobe component define a dovetail joint.

In another embodiment, the connector of the central lobe component is embodied as a tapered slot formed in an outer surface of the elongated body, with the connector of the side lobe component being embodied as a tapered tab extending outwardly from the curved inner sidewall. The tapered tab of the side lobe component is configured to be received into the tapered slot of the central lobe component so as to selectively lock the side lobe component to the central lobe component.

The side lobe component may be embodied as a medial lobe component or a lateral lobe component.

In an embodiment, a porous-metal coating is disposed on the outer surfaces of central lobe component and the side lobe component.

The bore of the central lobe component is defined by a conically-shaped sidewall extending through the elongated body of the central lobe component, and the conically-shaped sidewall may have a number cement pockets formed therein.

According to a further aspect of the disclosure, a method of surgically preparing a proximal end of a tibia of a patient includes determining a condition of bone tissue of the proximal end of the tibia of the patient, and thereafter forming a surgically-prepared cavity in the proximal end of the tibia of the tibia of a patient. A modular tibial cone augment is then assembled which corresponds to the shape of the surgically-prepared cavity by locking a side lobe component to a central lobe component, with the central lobe component having bore extending therethrough that is configured to receive a stem of a revision tibial prosthesis. The assembled modular tibial cone augment is then installed in the surgically-prepared cavity formed in the proximal end of the tibia.

In an embodiment, the side lobe component is embodied as a medial lobe component assembled to a medial side of the central lobe component.

In another embodiment, the side lobe component is embodied as a lateral lobe component assembled to a lateral side of the central lobe component.

In a further embodiment, the lobe component is embodied as a medial lobe component and a lateral lobe component. In such a case, the medial lobe component is assembled to a medial side of the central lobe component, and the lateral lobe component is assembled to a lateral side of the central lobe component.

According to yet another aspect of the disclosure, an orthopaedic knee implant includes a knee cone augment configured to be implanted into a surgically-prepared cavity in an end of a bone of a patient's knee. The knee cone augment includes a round elongated body having a superior end and an inferior end and a bore configured to receive a stem of a revision knee prosthesis extending through the elongated body. The bore is defined by a conically-shaped inner sidewall extending through the elongated body between its superior end and its inferior end. A number of impact lugs are secured to the inner sidewall at a location between the superior end and the inferior end of the elongated body. Each of the number of impact lugs extends inwardly from the inner sidewall toward a central axis of the bore, and has a flat, inferior-most impact surface.

In one example, the knee cone augment is embodied as a femoral cone augment configured to be implanted into a surgically-prepared cavity in a distal end of a femur of the patient's knee.

In an embodiment, each of the number of impact lugs includes a curved outer body extending superiorly from the impact surface. In such an example, the curved outer body of each of the number of impact lugs may be tapered in the superior/inferior direction such that a superior end thereof blends into the inner sidewall.

In an embodiment, the number of impact lugs includes a medial impact lug secured to a medial side of the inner sidewall and a lateral impact lug secured to a lateral side of the inner sidewall.

In an illustrative embodiment, the knee cone augment is embodied as a femoral cone augment configured to be implanted into a surgically-prepared cavity in a distal end of a femur of the patient's knee. The femoral cone augment has box cutout formed in a posterior side thereof, with the box cutout being configured to receive a box of a revision femoral prosthesis. The box cutout is defined in part by a flat, inferior-facing surface. The impact surface of each of the number of impact lugs is coplanar with the flat, inferior-facing surface of the box cutout.

In an embodiment, the impact surfaces of each of the number of impact lugs are coplanar with one another.

The inner sidewall may have a number cement pockets formed therein.

According to another aspect of the disclosure, an orthopaedic knee implant includes a femoral cone augment configured to be implanted into a surgically-prepared cavity in a distal end of a femur of a patient's knee. The femoral cone augment includes a round elongated body having a superior end and an inferior end and a bore configured to receive a stem of a revision femoral prosthesis extending through the elongated body. The bore is defined by a conically-shaped inner sidewall extending through the elongated body between its superior end and its inferior end. The femoral cone augment also includes a pair of impact lugs secured to the inner sidewall at a location between the superior end and the inferior end of the elongated body. Both of the pair of impact lugs extend inwardly from the inner sidewall toward a central axis of the bore, and have a flat, inferior-most impact surface.

In an embodiment, both of the pair of impact lugs include a curved outer body extending superiorly from the impact surface. In such an embodiment, the curved outer body of both of the pair of impact lugs may be tapered in the superior/inferior direction such that a superior end thereof blends into the inner sidewall.

The pair of impact lugs may include a medial impact lug secured to a medial side of the inner sidewall and a lateral impact lug secured to a lateral side of the inner sidewall.

The femoral cone augment may have a box cutout formed in a posterior side thereof. The box cutout is configured to receive a box of the revision femoral prosthesis and is defined in part by a flat, inferior-facing surface. The impact surface of both of the pair of impact lugs is coplanar with the flat, inferior-facing surface of the box cutout.

The impact surface of each of the number of impact lugs may be coplanar with one another.

The inner sidewall may have a number cement pockets formed therein.

According to a further aspect, an orthopaedic knee system includes a knee cone augment configured to be implanted into a surgically-prepared cavity in an end of a bone of a patient's knee. The knee cone augment includes a round elongated body having a superior end and an inferior end and a bore configured to receive a stem of a revision knee prosthesis extending through the elongated body. The bore is defined by a conically-shaped inner sidewall extending through the elongated body between its superior end and its inferior end. The knee cone augment also includes a number of impact lugs secured to the inner sidewall at a location between the superior end and the inferior end of the elongated body. Each of the number of impact lugs has a flat impact surface. The orthopaedic knee system also includes an impactor head configured to impact the knee cone augment during a surgical procedure to implant the knee cone augment. The impactor head has a proximal surface configured to be secured to an impaction handle and an impact surface opposite the proximal surface. The impact surface has a number of impact shoulders formed therein. Each of the number of impact shoulders has a flat impact surface that is sized and shaped to be positioned on the flat impact surface of one of the number of impact lugs of the knee cone augment when the impactor head is used to impact the knee cone augment.

In an example, the knee cone augment is embodied as a femoral cone augment configured to be implanted into a surgically-prepared cavity in a distal end of a femur of the patient's knee.

Each of the number of impact lugs may include a curved outer body extending away from the impact surface of the impact lug. The impactor head may have a number of guide slots formed therein, with each of the impact shoulders defining a proximal end of one of the number of guide slots. Each of the number of impact lugs of the knee cone implant is received into one of the number of guide slots of the impactor head when the impactor head is used to impact the knee cone augment.

The number of impact lugs may include a medial impact lug secured to a medial side of the inner sidewall and a lateral impact lug secured to a lateral side of the inner sidewall. In such an embodiment, the number of impact shoulders includes a medial impact shoulder formed in a medial side of the impactor head and a lateral impact shoulder formed in a lateral side of the impactor head.

In an example, the knee cone augment is embodied as a femoral cone augment configured to be implanted into a surgically-prepared cavity in a distal end of a femur of the patient's knee. The femoral cone augment has box cutout formed in a posterior side thereof, with the box cutout being configured to receive a box of a revision femoral prosthesis. The box cutout is defined in part by a flat, inferior-facing surface. The impact surface of the impactor head has an impact lip formed therein, with the impact lip having a flat impact surface that is sized and shaped to be positioned on the flat, inferior-facing surface of the box cutout when the impactor head is used to impact the knee cone augment.

The impact surface of each of the number of impact lugs of the femoral cone augment may be coplanar with the flat, inferior-facing surface of the box cutout of the femoral cone augment. In such an embodiment, the flat impact surface of each of the number of impact shoulders of the impactor head is coplanar with the flat impact surface of the impact lip of the impactor head.

According to another aspect, a method of surgically preparing a knee of a patient includes forming a surgically-prepared cavity in an end of a bone of the knee of the patient and thereafter positioning a knee cone augment in the cavity formed in the end of the bone. The knee cone augment has a bore formed therein and a number of impact lugs positioned in the bore. A distal end of an impactor head is advanced into the bore of knee cone augment such that a number of impact shoulders of the impactor head are positioned in contact with the number of impact lugs of the knee cone augment. Thereafter, the impactor head is impacted such that impaction forces are transferred from the number of impact shoulders of the impactor head to the number of impact lugs of the knee cone augment.

In an example, the knee cone augment is embodied as a femoral cone augment configured to be implanted into a surgically-prepared cavity in a distal end of a femur of the patient's knee. The femoral cone augment has box cutout formed in a posterior side thereof. The box cutout is configured to receive a box of a revision femoral prosthesis, and defined in part by a flat, inferior-facing surface. In such an embodiment, the distal end of an impactor head is advanced into the bore of the femoral cone augment such that an impact lip of the impactor head is positioned in contact with the flat, inferior-facing surface of the box cutout of the femoral cone augment. Impaction of the impactor head causes impaction forces to be transferred from the impact lip of the impactor head to the flat, inferior-facing surface of the box cutout of the femoral cone augment.

The method further includes removing a previously-installed knee implant from the end of a bone of the knee of the patient prior to forming the cavity in the end of the bone of the knee of the patient.

According to another aspect of the disclosure, an orthopaedic knee system includes a pair of knee cone components configured to be installed into a surgically-prepared cavity in an end of a bone of a patient's knee. Each of the pair of knee cone components has a conically-shaped hollow body configured to receive a stem of a revision knee prosthesis therethrough. The hollow body of both of the pair of knee cone components has a first end that tapers downwardly to a second end, with the first end of the hollow body defining an annular rim extending radially between an inner sidewall and an outer sidewall of the hollow body. The annular rim of a first knee cone component of the pair of knee cone components has an inner diameter that is smaller than an inner diameter of the annular rim of a second knee component of the pair of knee cone components. The orthopaedic knee system also includes an impactor head configured to impact the pair of knee cone components during a surgical procedure. The impactor head includes a proximal surface configured to be secured to an impaction handle and an impact surface opposite the proximal surface. The impact surface has a pair of annular-shaped concentric impact flanges formed therein. A first impact flange of the pair of impact flanges has a diameter that is larger than the inner diameter of the annular rim of the first knee cone component of the pair of knee cone components, but smaller than the inner diameter of the annular rim of the second knee cone component of the pair of knee cone components. A second impact flange of the pair of impact flanges has a diameter that is larger than the inner diameters of the annular rims of both the first knee cone component and the second knee cone component of the pair of knee cone components.

In an embodiment, the impact surface of the impactor head further has an annular-shaped lead-in flange that is concentric with the pair of impact flanges. The lead-in flange has a diameter that is smaller than the inner diameters of the annular rims of both the first knee cone component and the second knee cone component of the pair of knee cone components.

In an example, the pair of knee cone components is embodied as a pair of knee cone trial components.

In another example, the pair of knee cone components is embodied as a pair of femoral cone augments configured to be implanted into a surgically-prepared cavity in a distal end of a femur of the patient's knee.

The pair of knee cone components may also be embodied as a pair of tibial cone augments configured to be implanted into a surgically-prepared cavity in a proximal end of a tibia of the patient's knee.

Yet further, the pair of knee cone components may be embodied as a pair of concentric knee cone augments configured to be implanted into one or both of a surgically-prepared cavity in a distal end of a femur of the patient's knee and a surgically-prepared cavity in a proximal end of a tibia of the patient's knee.

According to another aspect, an orthopaedic knee system includes a first conically-shaped concentric knee cone component configured to be installed into a surgically-prepared cavity in an end of a bone of a patient's knee. The first concentric knee component has an annular rim with an inner diameter. The orthopaedic knee system also includes a second conically-shaped concentric knee cone component configured to be installed into the surgically-prepared cavity in the end of the bone of the patient's knee. The second concentric knee cone component has an annular rim with an inner diameter. The inner diameter of the annular rim of the second concentric knee cone component is larger than the inner diameter of the annular rim of the first concentric knee cone component. The orthopaedic knee system also includes an impactor head configured to impact the first knee cone component and the second knee cone component during a surgical procedure. The impactor head includes a proximal surface configured to be secured to an impaction handle and an impact surface opposite the proximal surface. The impact surface has a pair of annular-shaped concentric impact flanges formed therein. A first impact flange of the pair of impact flanges has a diameter that is larger than the inner diameter of the annular rim of the first knee cone component, but smaller than the inner diameter of the annular rim of the second knee cone component. A second impact flange of the pair of impact flanges has a diameter that is larger than the inner diameters of the annular rims of both the first knee cone component and the second knee cone component.

The impact surface of the impactor head further has an annular-shaped lead-in flange that is concentric with the pair of impact flanges. The lead-in flange has a diameter that is smaller than the inner diameters of the annular rims of both the first knee cone component and the second knee cone component.

The first knee cone component and the second knee cone component may be embodied as a pair of knee cone trial components.

The first knee cone component and the second knee cone component may be embodied a pair of femoral cone augments configured to be implanted into a surgically-prepared cavity in a distal end of a femur of the patient's knee.

The first knee cone component and the second knee cone component may be embodied a pair of tibial cone augments configured to be implanted into a surgically-prepared cavity in a proximal end of a tibia of the patient's knee.

The first knee cone component and the second knee cone component are configured to be implanted into one or both of a surgically-prepared cavity in a distal end of a femur of the patient's knee and a surgically-prepared cavity in a proximal end of a tibia of the patient's knee.

According to yet another aspect of the disclosure, a method of surgically preparing a knee of a patient includes forming a surgically-prepared cavity in an end of a bone of the knee of the patient. A knee cone augment is selected from a pair of knee cone augments that includes a first knee cone augment and a second knee cone augment, the first knee cone augment having an annular rim that is smaller than an annular rim of the second knee cone augment. The selected knee cone augment is positioned in the cavity formed in the end of the bone. Thereafter, a distal end of an impactor head is advanced into a bore of the selected knee cone augment such that a smaller impact flange of a pair of annular-shaped concentric impact flanges formed in the impactor head is positioned in contact with the annular rim of the selected knee cone augment if the selected knee cone augment is the first knee cone component. Or, the smaller impact flange of the pair of annular-shaped concentric impact flanges of the impactor head is positioned in the bore of the selected knee cone component and a larger impact flange of the pair of annular-shaped concentric impact flanges of the impactor head is positioned in contact with the annular rim of the selected knee cone augment if the selected knee cone augment is the second knee cone component. The impactor head is then impacted such that impaction forces are transferred from one of the pair of annular-shaped concentric impact flanges of the impactor head to the selected knee cone augment.

In an embodiment, the impactor head has an annular-shaped lead-in flange that is concentric with the pair of annular-shaped concentric impact flanges. The lead-in flange is advanced into the bore of the selected knee cone augment during advancement of the distal end of the impactor head.

In an embodiment, the surgically-prepared cavity is formed in a distal end of a femur of the knee of the patient and the selected knee cone augment is positioned in the cavity formed in the distal end of the femur of the knee of the patient.

In an embodiment, the surgically-prepared cavity is formed in a proximal end of a tibia of the knee of the patient and the selected knee cone augment is positioned in the cavity formed in the proximal end of the tibia of the knee of the patient.

The method may also include removing a previously-installed knee implant from the end of a bone of the knee of the patient prior to forming the cavity in the end of the bone of the knee of the patient.

According to a further aspect of the present disclosure, an orthopaedic knee system includes a plurality of knee cone trial components configured to be installed into a surgically-prepared cavity in an end of a bone of a patient's knee. Each of the plurality of knee cone components has a conically-shaped hollow body configured to receive a stem trial component therethrough. The hollow body of each of the plurality of knee cone trial components has a pair of extraction openings formed therein, with each of the pair of extraction openings being positioned on opposite sides of the hollow body from the other. Each of the pair of extraction openings extends between an inner sidewall and an outer sidewall of the hollow body. The orthopaedic knee system also includes a trial extractor operable to extract each of the plurality of knee cone trial components from the surgically-prepared cavity in the end of the bone of the patient's knee. The trial extractor includes a connector body configured to be secured to an impaction handle and a pair of extractor arms pivotally coupled to the connector body. Each of the pair of extractor arms has a prong formed in a distal end thereof. The prong of each of the pair of extractor arms is sized and shaped to be received into one of the extraction openings formed in each of the plurality of knee cone trial components. The trial extractor also includes a spring asserting a spring bias on the pair of extractor arms so as to urge the prongs away from one another.

The connector body of the trial extractor may also include a pair of mounting flanges spaced apart from one another, with each of the pair of mounting flanges having an aperture defined therein. A proximal end of each of the pair of extractor arms has an aperture defined therein. The trial extractor further comprises a pivot pin. The pivot pin is positioned in the aperture of each of the pair of mounting flanges and the aperture of each of the pair of extractor arms so as to pivotally couple the pair of extractor arms to the connector body.

In an embodiment, the proximal end of each of the pair of extractor arms is positioned between the pair of mounting flanges.

In an example, the spring is embodied a torsion spring having a loop and a pair of spring arms. Each of the pair of spring arms is biased against one of the pair of extractor arms, and the pivot pin extends through the loop.

In an embodiment, each of the pair of extraction openings is diamond shaped and each of the prongs formed in the pair of extractor arms comprises a pointed tip that is sized and shaped to be received into one of the diamond shaped extraction openings.

A first extraction opening of the pair of extraction openings may be positioned on a medial side of the hollow body, and a second extraction opening of the pair of extraction openings may be positioned on a lateral side of the hollow body.

The plurality of knee cone trial components may be embodied as a plurality of femoral cone trial components configured to be installed into a surgically-prepared cavity in a distal end of a femur of the patient's knee.

The plurality of knee cone trial components may be embodied as a plurality of tibial cone trial components configured to be installed into a surgically-prepared cavity in a proximal end of a tibia of the patient's knee.

The plurality of knee cone trial components may be embodied as a plurality of concentric knee cone trial components configured to be installed into one or both of a surgically-prepared cavity in a distal end of a femur of the patient's knee and a surgically-prepared cavity in a proximal end of a tibia of the patient's knee.

According to another aspect of the disclosure, an orthopaedic knee instrument assembly includes an impaction handle having an elongated body, an impact plate secured to a proximal end of the elongated body, and a connector positioned on a distal end of the elongated body opposite the impact plate. The orthopaedic knee instrument assembly also includes a trial extractor removabley secured to the impaction handle. The trial extractor includes a connector body having a connector configured to be secured to the connector of the impaction handle and a pair of extractor arms pivotally coupled to the connector body. Each of the pair of extractor arms has a prong formed in a distal end thereof. The prong of each of the pair of extractor arms being sized and shaped to be received into an extraction opening formed in a knee cone trial component. The trial extractor also includes a spring asserting a spring bias on the pair of extractor arms so as to urge the prongs away from one another.

The connector body of the trial extractor may also include a pair of mounting flanges spaced apart from one another, with each of the pair of mounting flanges having an aperture defined therein. A proximal end of each of the pair of extractor arms has an aperture defined therein. The trial extractor further comprises a pivot pin. The pivot pin is positioned in the aperture of each of the pair of mounting flanges and the aperture of each of the pair of extractor arms so as to pivotally couple the pair of extractor arms to the connector body.

In an embodiment, the proximal end of each of the pair of extractor arms is positioned between the pair of mounting flanges.

In an example, the spring is embodied a torsion spring having a loop and a pair of spring arms. Each of the pair of spring arms is biased against one of the pair of extractor arms, and the pivot pin extends through the loop.

In an embodiment, each of the prongs formed in the pair of extractor arms includes a pointed tip that is sized and shaped to be received into a diamond shaped extraction opening.

According to another aspect of the disclosure, a method of surgically preparing a knee of a patient includes forming a surgically-prepared cavity in an end of a bone of the knee of the patient and positioning a knee cone trial component in the cavity formed in the end of the bone. Thereafter, the knee of the patient is moved through a trial range of motion. A trial extractor is then advanced such that a distal end of each of a pair of extractor arms of the trial extractor is positioned in a bore of the knee cone trial component. The distal end of each of the pair of extractor arms has a prong formed therein, with such a prong of each of the pair of extractor arms being positioned into one of a pair of extraction openings formed in the knee cone trial component. An extraction force is asserted on the trial extractor so as to extract the knee cone trial component from the cavity formed in the end of the bone.

The pair of extractor arms may be squeezed toward one another during advancement into the bore of the knee cone trial component. The pair of extractor arms are then released so as to allow a spring bias to urge the prongs formed in the distal end of each of the pair of extractor arms away from one another and into the pair of extraction openings formed in the knee cone trial component.

In an embodiment, the surgically-prepared cavity is formed in a distal end of a femur of the knee of the patient and the knee cone trial component is positioned in the cavity formed in the distal end of the femur of the knee of the patient.

In an embodiment, the surgically-prepared cavity is formed in a proximal end of a tibia of the knee of the patient and the knee cone trial component is positioned in the cavity formed in the proximal end of the tibia of the knee of the patient.

The method may also include removing a previously-installed knee implant from the end of a bone of the knee of the patient prior to forming the cavity in the end of the bone of the knee of the patient.

BRIEF DESCRIPTION OF THE DRAWINGS

The detailed description particularly refers to the following figures, in which:

FIG. 53 illustrates the impactor head of FIG. 50 being used in a surgical procedure to implant the femoral cone augment of FIGS. 12-14 and FIG. 54 illustrates the impactor head of FIG. 50 positioned in contact with the femoral cone augment of FIGS. 12-14 and 42-45;

FIG. 55 is a cross sectional view taken along the line 55-55 of FIG. 54, as viewed in the direction of the arrows;

FIG. 56 is a cross sectional view taken along the line 56-56 of FIG. 54, as viewed in the direction of the arrows;

FIG. 80 is a perspective view of a tibial cone trial component;

FIG. 81 is a superior view of the tibial cone trial component of FIG. 80;

FIG. 82 is an anterior view of the tibial cone trial component of FIG. 80.

DETAILED DESCRIPTION OF THE DRAWINGS

Figures 1, 2, 3, 4:
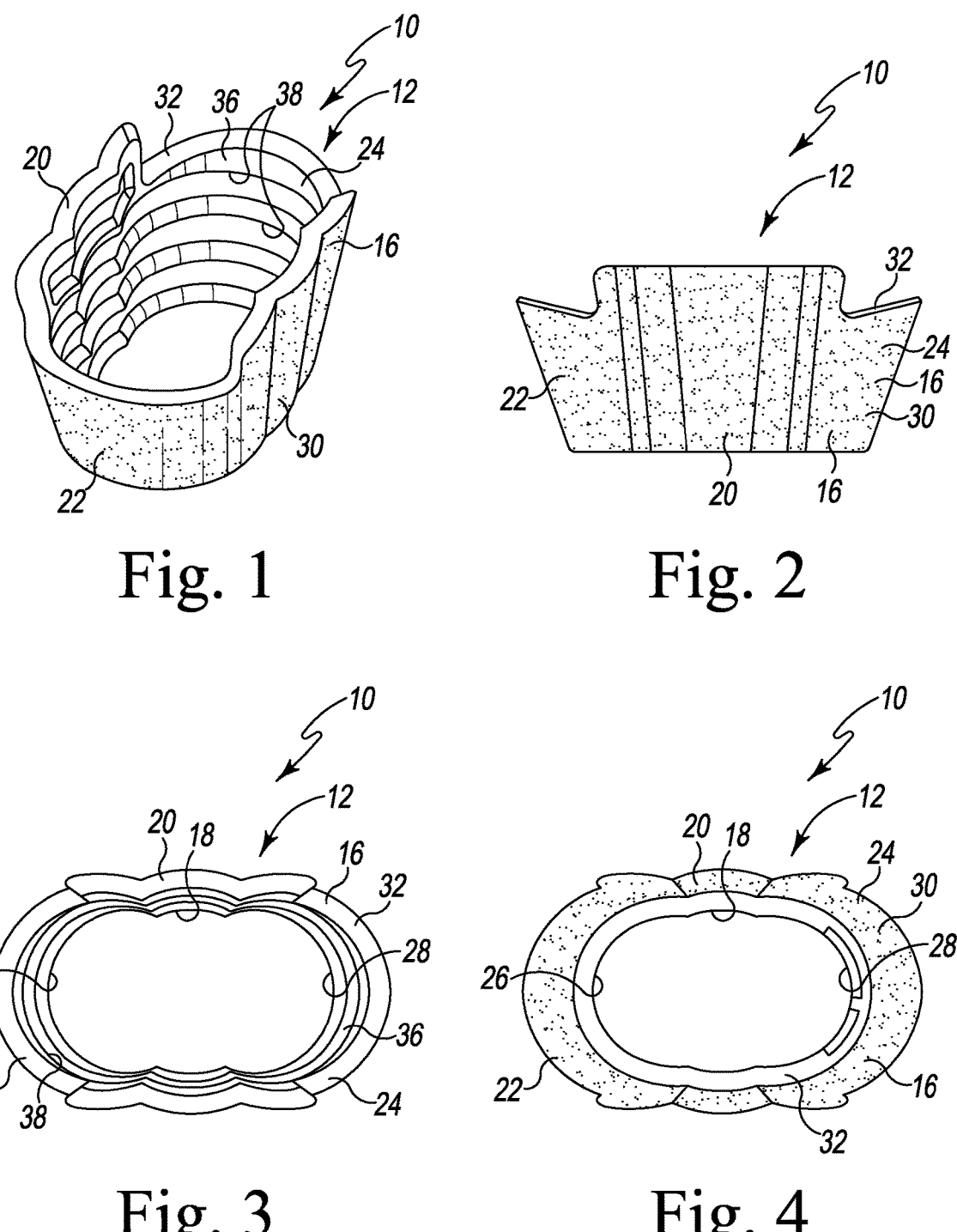
FIG. 1 is perspective view of tibial cone augment for use with a revision knee prosthesis.
FIG. 2 is an anterior view of the tibial cone augment of FIG. 1.
FIG. 3 is a superior view of the tibial cone augment of FIG. 1.
FIG. 4 is an inferior view of the tibial cone augment of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The exemplary embodiments of the present disclosure are described and illustrated below to encompass prosthetic knee joints and knee joint components, as well as methods of implanting and reconstructing knee joints. It will also be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Various illustrative embodiments of knee cone augments are disclosed herein. Consistent with its usage in the art, what is meant herein by the term "cone augment" is an augment component that is not mechanically locked or otherwise secured to a revision knee prosthesis prior to implantation of the prosthesis, but rather is first separately implanted into the bone of the patient and thereafter secured to the subsequently implanted revision knee prosthesis, if secured to it at all, by use of an adhesive, such as bone cement. As a result, when installed in conjunction with the revision knee prosthesis, the cone augment does not physically contact the revision knee prosthesis, but rather is mechanically secured to it by the adhesive (e.g., bone cement), if secured to the revision knee prosthesis at all (e.g., the cone augment is not secured at all to a press-fit (i.e., cementless) stem component). As such, as used herein, a cone augment is distinct from a sleeve augment given sleeve augments are mechanically locked to a revision knee prosthesis prior to implantation of the prosthesis.

Referring now to FIGS. 1-11, an orthopaedic joint replacement system 10 includes a number of orthopaedic prosthetic components such as a tibial cone augment 12 and a number of orthopaedic surgical instruments such as a tibial surgical broach 14 (see, for example, FIGS. 5-7) for use in preparing the bone to receive one or more of the tibial cone augments 12. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic prosthetic components or implants, such as those shown in FIGS. 1-4.

The tibial cone augment 12 includes an elongated hollow body 16 having a central lobe section 20, a medial lobe section 22, and a lateral lobe section 24. It should be appreciated that although the tibial cone augment 12 is herein shown as a tri-lobe tibial augment (i.e., it has three lobe sections 20, 22, 24), the tibial cone augment 12 may be embodied as a bi-lobe tibial augment (i.e., having a central lobe section 20 and only one of the medial lobe section 22 or the lateral lobe section 24, but not both) or a concentric tibial augment (i.e., having a central lobe section 20, but neither the medial lobe section 22 nor the lateral lobe section 24). A bore 18 defined by the hollow body 16 in the central lobe section 20 is sized and shaped to receive a tibial stem component of a tibial revision prosthesis (not shown). Moreover, the size and shape of the bores 26, 28 defined by the hollow body 16 in the medial lobe section 22 and lateral lobe section 24, respectively, allow the position of the tibial stem component of the tibial revision prosthesis to be offset in the medial/lateral direction from the central lobe section as needed to fit the needs of a given surgical installation. Moreover, the bores 18, 26, 28 defined by the hollow body 16 allow for receipt of structures on the inferior side of a revision tibial tray such as one or more keels.

The body 16 of the tibial cone augment 12 is illustratively embodied as a solid-metal base 32 having a porous-metal coating 30 disposed thereon. It should be appreciated that the porous-metal coating 30 could be a separately-applied coating such as Porocoat® Porous Coating which is commercially available from DePuy Synthes of Warsaw, Indiana. However, in the illustrative embodiment described herein, the porous-metal coating 30 is disposed on the solid-metal base 32 by virtue of being additively manufactured contemporaneously with the solid-metal base 32 so as to create a common, monolithic component of the two metal structures.

In one example, the porous-metal coating 30 may be made of a porous material as described in U.S. patent application Ser. No. 16/365,557, which was filed Mar. 26, 2019 and is assigned to the same assignee as the present disclosure, the disclosure of which is hereby incorporated by reference as if set forth in its entirety herein. Additive manufacturing processes can include, by way of example, powder bed fusion printing, such as melting and sintering, cold spray 3D printing, wire feed 3D printing, fused deposition 3D printing, extrusion 3D printing, liquid metal 3D printing, stereolithography 3D printing, binder jetting 3D printing, material jetting 3D printing, and the like.

In one example, the porous material of the porous-metal coating 30 may be defined by a porous three-dimensional structure that includes a plurality of connected unit cells. Each unit cell may define a unit cell structure that includes a plurality of lattice struts that define an outer geometric structure and a plurality of internal struts that define a plurality of internal geometric structures that are disposed within the outer geometric structure. In one example, the outer geometric structure may be a rhombic dodecahedron, and the inner geometric structures may be a rhombic trigonal trapezohedron. It should be appreciated that such geometric structures may be varied to fit the needs of a given design. Further, it should be appreciated that the unit cells that make up the porous-metal coating 30 may also have any suitable alternative geometry to fit the needs of a given design.

The porous material of the porous-metal coating 30 is formed from a metal powder. Illustratively, the metal powders may include, but are not limited to, titanium, titanium alloys, stainless steel, cobalt chrome alloys, tantalum, or niobium powders. The porous-metal coating 30 has a porosity suitable to facilitate bony ingrowth into the tibial cone augment 12 when it is implanted into the surgically-prepared proximal end of the patient's tibia.

In the illustrative embodiment described herein, the porous-metal coating 30 is additively manufactured directly onto the outer surfaces of the solid-metal base 32. In such an embodiment, the two structures—i.e., the solid-metal base 32 and the porous-metal coating 30—may be manufactured contemporaneously during a common additive manufacturing process. For example, the two structures may be manufactured contemporaneously in a single 3D printing operation that yields a common, monolithic metallic component including both structures. Alternatively, the porous-metal coating 30 could be manufactured as a separate component that is secured to the solid-metal base 32.

As can be seen in FIGS. 1 and 3, the inner sidewall 36 that defines the bores 18, 26, 28 of the hollow body 16 has a number of cement pockets 38 formed therein. Bone cement is received into the cement pockets 38 to increase adhesion of the cement to the tibial cone augment 12 during implantation of the tibial revision prosthesis.

Figure 8:
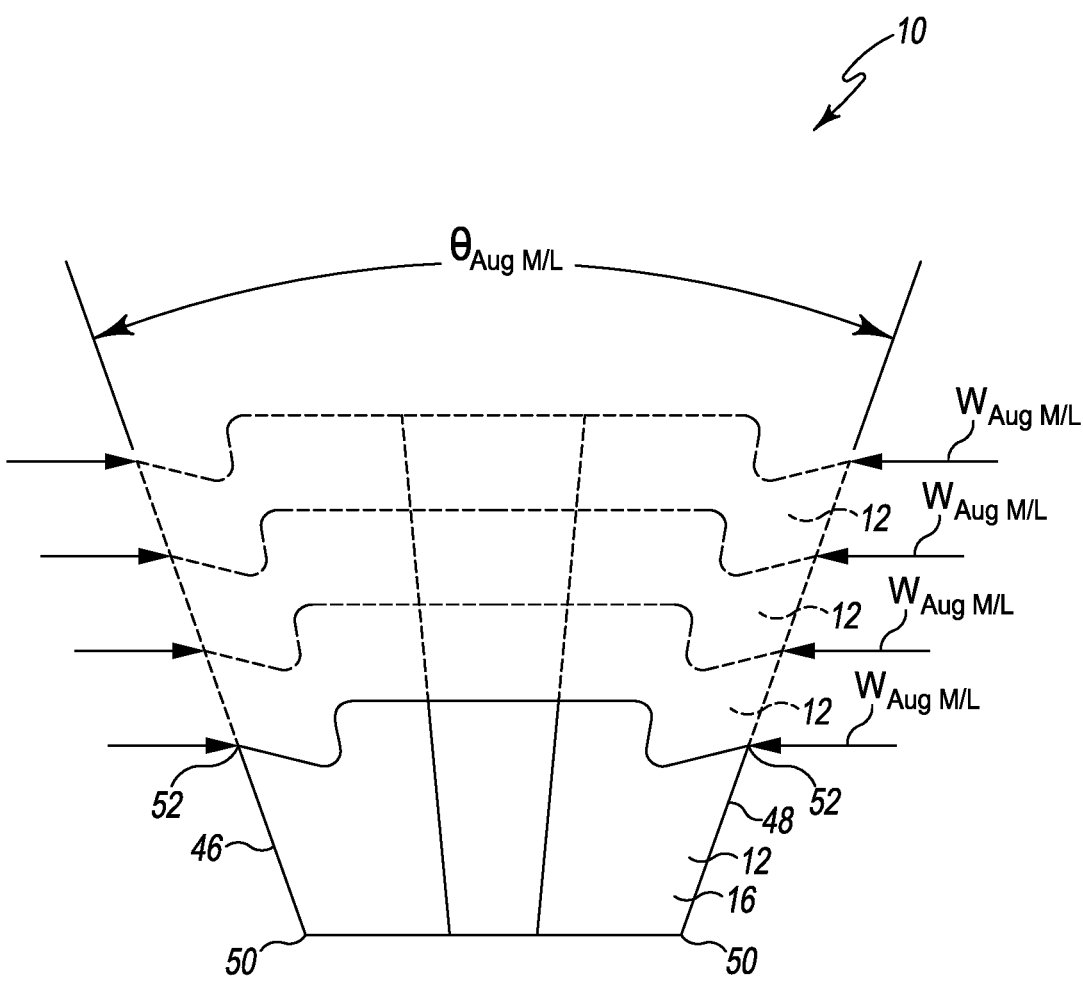
FIG. 8 is a diagrammatic view showing multiple sizes of the tibial cone augment of FIGS. 1-4 superimposed on one another, as viewed in the medial/lateral direction.
Figure 9:
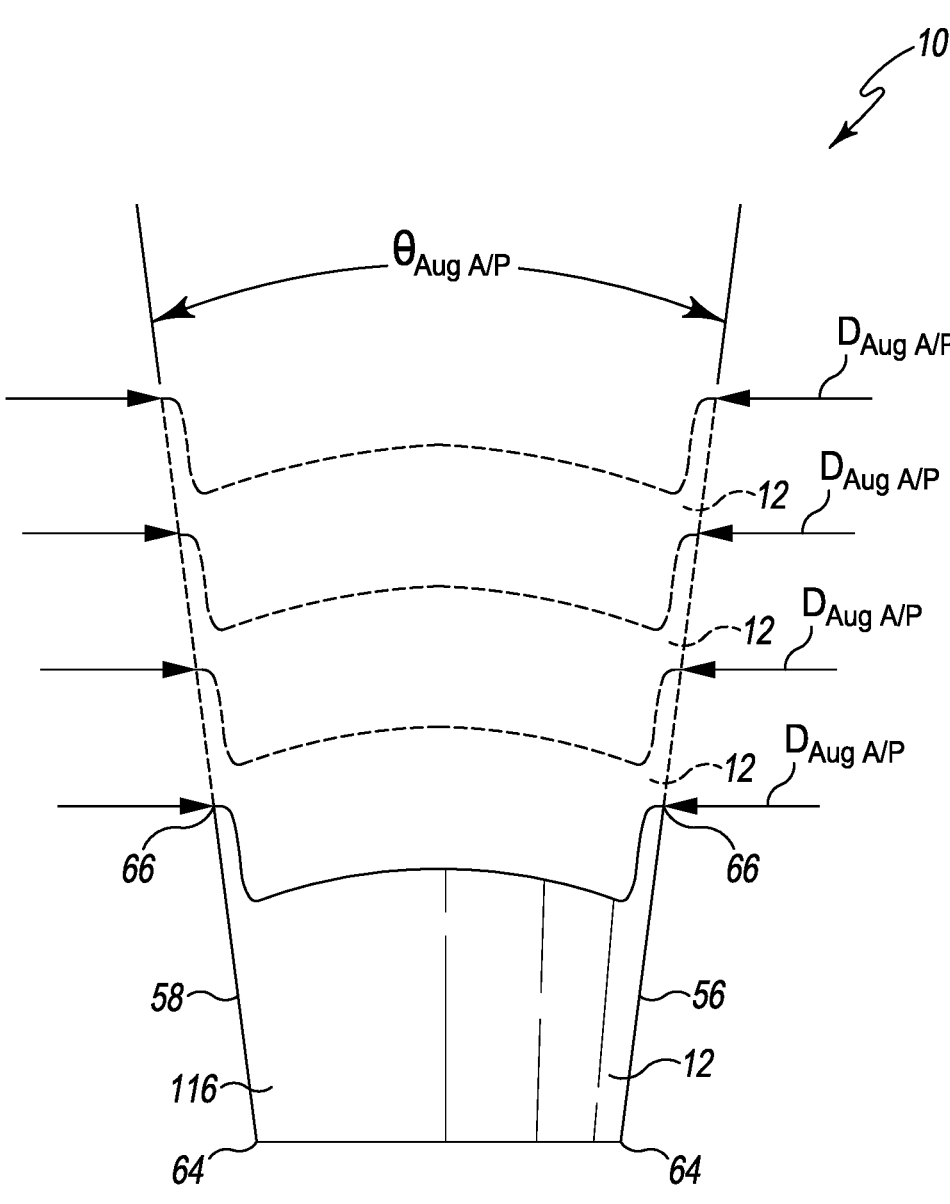
FIG. 9 is a diagrammatic view showing multiple sizes of the tibial cone augment of FIGS. 1-4 superimposed on one another, as viewed in the anterior/posterior direction.

As shown in FIGS. 8 and 9, the tibial cone augment 12 may be provided in a number of different configurations to fit the needs of a given patient's anatomy. In particular, the tibial cone augment 12 may be configured in various different sizes to conform to the patient's anatomy and/or accommodate a wide range of bone loss. In one illustrative embodiment, the tibial cone augment 12 may be provided in four different sizes (e.g., Sizes Small (S), Medium (M), Large (L), Extra Large (XL)). As shown in FIG. 8, the medial/lateral augment width of the body 16 changes as a function of the size of the tibial cone augment 12. As used herein, the term "medial/lateral augment width" refers to the width of the augment at its widest medial/lateral dimension. As can be seen in FIG. 8, the medial/lateral augment width ($W_{AugM/L}$) of the tibial cone augment 12 increases as the size of the tibial cone augment 12 increases. In other words, a Size M tibial cone augment 12 has a larger medial/lateral width than a Size S tibial cone augment 12, but a smaller medial/lateral width than a Size L (or Size XL) tibial cone augment 12.

However, as shown in FIG. 8, each of the differently-sized tibial cone augments 12 has a common taper angle in the medial/lateral direction (i.e., a common medial/lateral augment taper angle). In particular, the cone augment's "medial/lateral augment taper angle" is defined herein as the magnitude of the angle formed by the entirety of the medial-most edge 46 and the entirety of the lateral-most edge 48 of the augment. In other words, the cone augment's "medial/lateral augment taper angle" is defined as the magnitude of the angle formed by the medial-most edge 46 and the lateral-most edge 48 of the augment from the inferior-most end 50 of each edge 46, 48 to the superior-most end 52 of each edge 46, 48. As can be seen in FIG. 8, each of the differently-sized tibial cone augments 12 has a common medial/lateral augment taper angle ($\theta_{AugM/L}$). In the exemplary embodiment described herein, each of the differently-sized tibial cone augments 12 has a medial/lateral augment taper angle of 39° (i.e., $\theta_{AugM/L}$=39°.

As shown in FIG. 9, the anterior/posterior augment depth of the body 16 changes as a function of the size of the tibial cone augment 12. As used herein, the term "anterior/posterior augment depth" refers to the width of the augment at its widest anterior/posterior dimension. As can be seen in FIG. 9, the anterior/posterior augment depth ($D_{AugA/P}$) of the tibial cone augment 12 increases as the size of the tibial cone augment 12 increases. In other words, a Size M tibial cone augment 12 has a larger anterior/posterior augment depth than a Size S tibial cone augment 12, but a smaller anterior/posterior augment depth than a Size L (or Size XL) tibial cone augment 12.

However, as shown in FIG. 9, each of the differently-sized tibial cone augments 12 has a common taper angle in the anterior/posterior direction (i.e., a common anterior/posterior augment taper angle). In particular, the cone augment's "anterior/posterior augment taper angle" is defined herein as the magnitude of the angle formed by the entirety of the anterior-most edge 56 and the entirety of the posterior-most edge 58 of the augment. In other words, the cone augment's "anterior/posterior augment taper angle" is the magnitude of the angle formed by the anterior-most edge 56 and the lateral-most edge 58 of the cone augment from the inferior-most end 64 of each edge 56, 58 to the superior-most end 66 of each edge 56, 58. As can be seen in FIG. 9, each of the differently-sized tibial cone augments 12 has a common anterior/posterior augment taper angle ($\theta_{AugA/P}$). In the exemplary embodiment described herein, each of the differently-sized tibial cone augments 12 has an anterior/posterior augment taper angle of 14° (i.e., $\theta_{AugA/P}$=14°.

Figures 5, 6, 7:
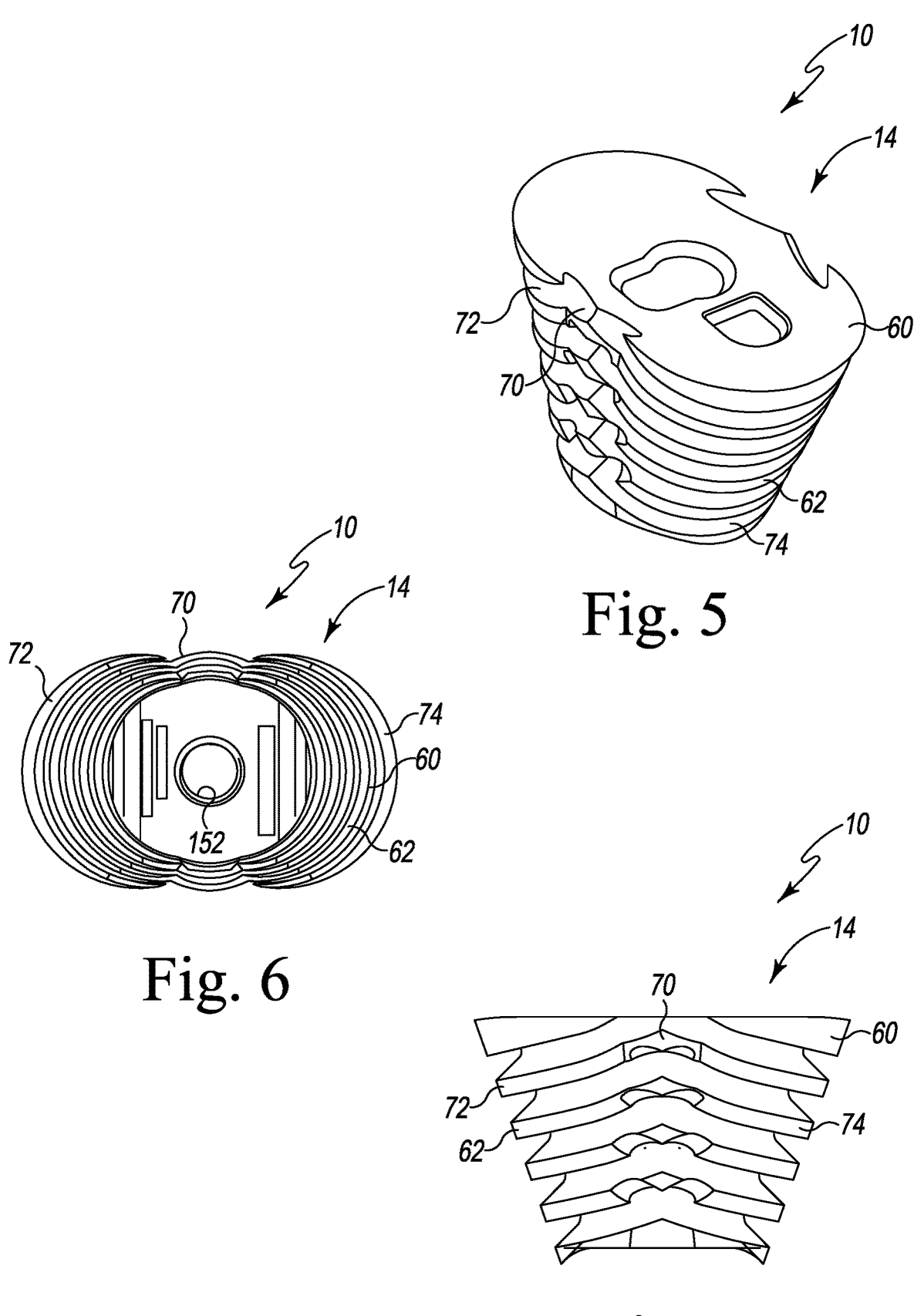
FIG. 5 is a perspective view of a tibial surgical broach for use in an orthopaedic surgical procedure to implant the tibial cone augment of FIGS. 1-4.
FIG. 6 is an inferior view of the tibial surgical broach of FIG. 5.
FIG. 7 is an anterior view of the tibial surgical broach of FIG. 5.

As shown in FIGS. 5-7, the tibial surgical broach 14 has a geometry that closely corresponds to the geometry of the tibial cone augment 12. In particular, the tibial surgical broach 14 has body 60 that includes a number of cutting teeth 62 that are configured to cut and remove bone tissue in a shape that corresponds to the shape of the tibial cone augment 12. As such, the cutting teeth 62 are arranged in a central lobe section 70, a medial lobe section 72, and a lateral lobe section 74. As with the tibial cone augment 12, it should be appreciated that although the tibial surgical broach 14 is herein shown as a tri-lobe tibial surgical broach (i.e., it has three lobe sections 70, 72, 74), the tibial surgical broach 14 may be embodied as a bi-lobe tibial surgical broach (i.e., having a central lobe section 70 and only one of the medial lobe section 72 or the lateral lobe section 74, but not both) or a concentric tibial surgical broach (i.e., having a central lobe section 70, but neither the medial lobe section 72 nor the lateral lobe section 74).

In the illustrative embodiment described herein, the tibial surgical broach 14 is constructed with stainless steel. Other suitable materials may be used to fit the needs of a given design of the broach 14.

Figure 10:
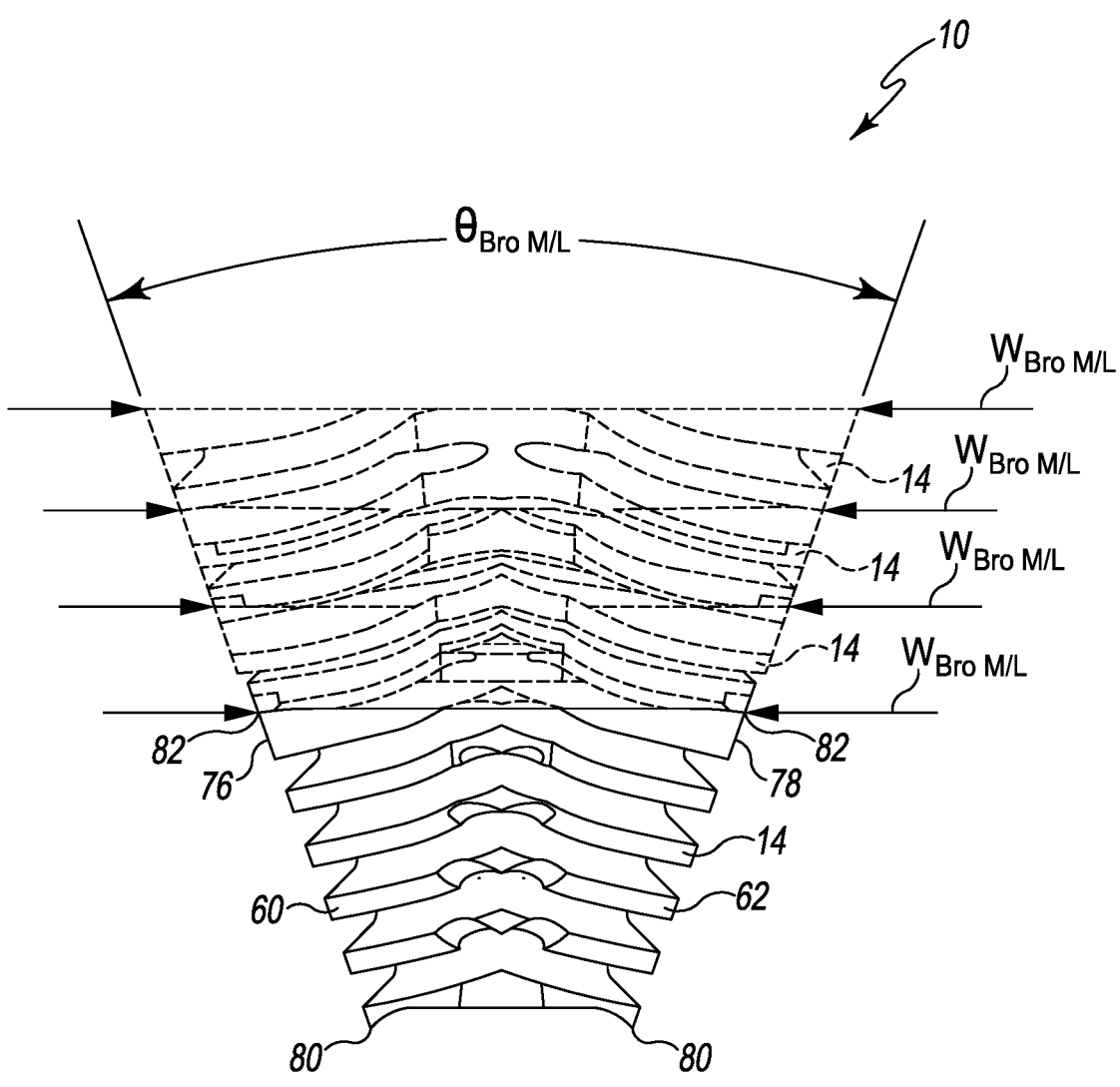
FIG. 10 is a diagrammatic view showing multiple sizes of the tibial surgical broach of FIGS. 5-7 superimposed on one another, as viewed in the medial/lateral direction.
Figure 11:
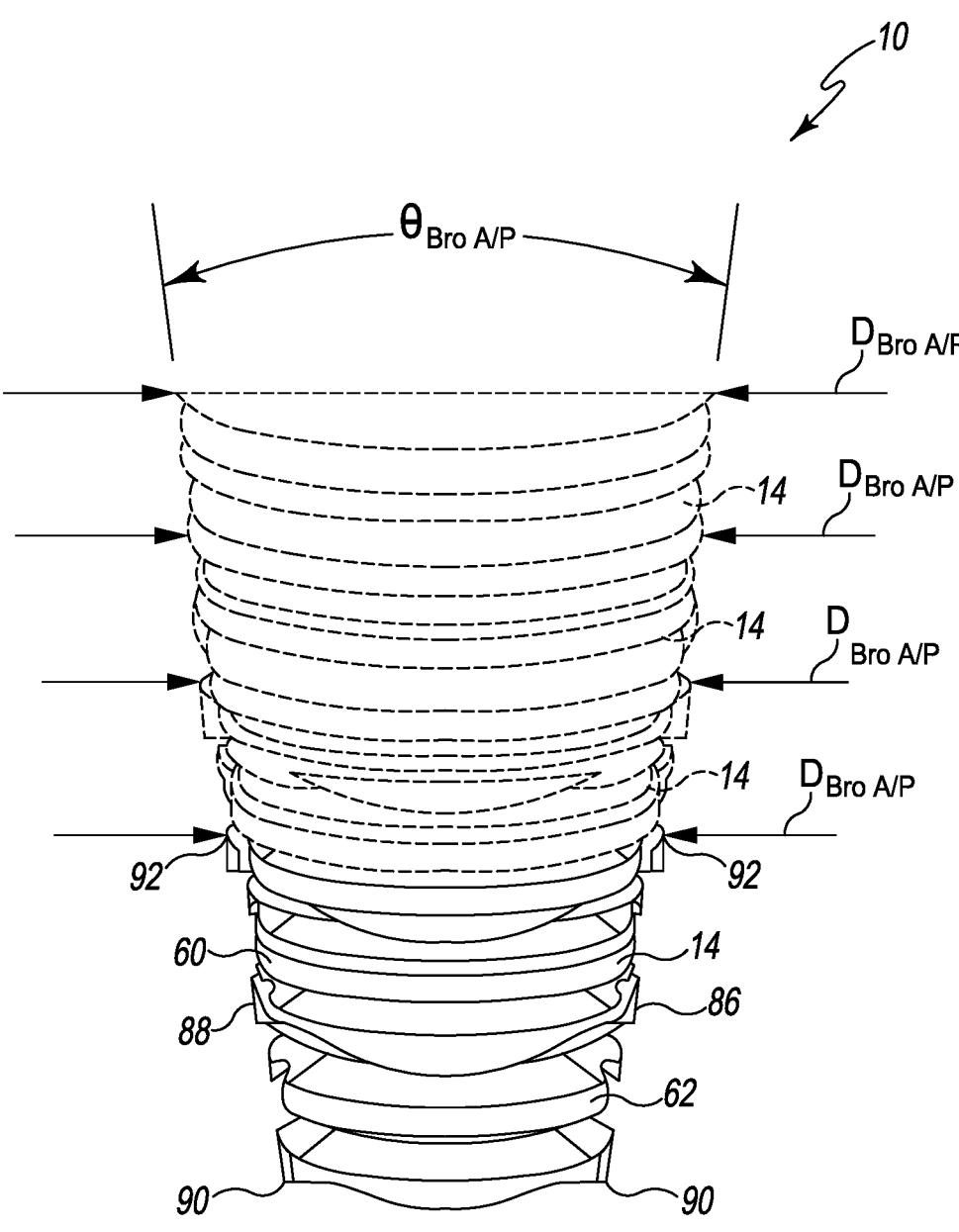
FIG. 11 is a diagrammatic view showing multiple sizes of the tibial surgical broach of FIGS. 5-7 superimposed on one another, as viewed in the anterior/posterior direction.

As shown in FIGS. 10 and 11, the tibial surgical broach 14 may be provided in a number of different configurations to correspond to the different configurations of the tibial cone augment 12. In particular, the tibial surgical broach 14 may be configured in various different sizes to conform to the sizes of the tibial cone augment 12. As such, in one illustrative embodiment, the tibial surgical broach 14 may be provided in four different sizes (e.g., Sizes Small (S), Medium (M), Large (L), Extra Large (XL)). As shown in FIG. 10, the medial/lateral broach width of the body 60 changes as a function of the size of the tibial surgical broach 14. As used herein, the term "medial/lateral broach width" refers to the width of the broach at its widest medial/lateral dimension. As can be seen in FIG. 10, the medial/lateral broach width ($W_{BroM/L}$) of the tibial surgical broach 14 increases as the size of the tibial surgical broach 14 increases. In other words, a Size M tibial surgical broach 14 has a larger medial/lateral broach width than a Size S tibial surgical broach 14, but a smaller medial/lateral broach width than a Size L (or XL) tibial surgical broach 14.

However, like the tibial cone augment 12 and as shown in FIG. 10, each of the differently-sized tibial surgical broaches 14 has a common taper angle in the medial/lateral direction (i.e., a common medial/lateral broach taper angle). In particular, the surgical broach's "medial/lateral broach taper angle" is defined herein as the magnitude of the angle formed by the entirety of an imaginary line extending along and connecting the medial-most edges 76 of the broach's individual cutting teeth 62 and the entirety of an imaginary line extending along and connecting the lateral-most edges 78 of the broach's individual cutting teeth 62. In other words, the surgical broach's "medial/lateral broach taper angle" is the magnitude of the angle formed by the imaginary line extending along and connecting the medial-most edges 76 of the broach's individual cutting teeth 62 and the imaginary line extending along and connecting the lateral-most edges 78 of the broach's individual cutting teeth 62 from the distal-most end 80 of each imaginary line to the proximal-most end 82 of each imaginary line.

Moreover, the medial/lateral broach taper angle of the broach 14 is the same as the medial/lateral augment taper angle of the tibial cone augment 12. Specifically, the medial/lateral taper angle of the broach 14 matches the medial/lateral taper angle of the augment 12. As such and as can be seen in FIGS. 8 and 10, each of the differently-sized tibial surgical broaches 14 has a common medial/lateral broach taper angle ($\theta_{BroM/L}$), which is the same as the medial/lateral augment taper angle ($\theta_{AugM/L}$) common to each of the tibial cone augments 12. In the exemplary embodiment described herein, each of the differently-sized tibial surgical broaches has a medial/lateral broach taper angle of 39° (i.e., $\theta_{BroM/L}$=39°.

As shown in FIG. 11, the anterior/posterior broach depth of the body 60 changes as a function of the size of the tibial surgical broach 14. As used herein, the term "anterior/posterior broach depth" refers to the width of the broach at its widest anterior/posterior dimension. As can be seen in FIG. 11, the anterior/posterior broach depth ($D_{BroA/P}$) of the tibial surgical broach 14 increases as the size of the tibial surgical broach 14 increases. In other words, a Size M tibial surgical broach 14 has a larger anterior/posterior broach depth than a Size S tibial surgical broach 14, but a smaller anterior/posterior augment depth than a Size L (or Size XL) tibial surgical broach 14.

However, as shown in FIG. 11, each of the differently-sized tibial surgical broaches 14 has a common taper angle in the anterior/posterior direction (i.e., a common anterior/posterior broach taper angle). In particular, the tibial surgical broach's "anterior/posterior broach taper angle" is defined herein as the magnitude of the angle formed by the entirety of an imaginary line extending along and connecting the anterior-most edges 86 of the broach's individual cutting teeth 62 and the entirety of an imaginary line extending along and connecting the posterior-most edges 88 of the broach's individual cutting teeth 62. In other words, the surgical broach's "anterior/posterior broach taper angle" is the magnitude of the angle formed by the imaginary line extending along and connecting the anterior-most edges 86 of the broach's individual cutting teeth 62 and the imaginary line extending along and connecting the posterior-most edges 88 of the broach's individual cutting teeth 62 from the distal-most end 90 of each imaginary line to the proximal-most end 92 of each imaginary line.

Moreover, the anterior/posterior broach taper angle of the broach 14 is the same as the anterior/posterior augment taper angle of the tibial augment component 12. Specifically, the anterior/posterior taper angle of the broach 14 matches the anterior/posterior taper angle of the augment 12. As such and as can be seen in FIGS. 9 and 11, each of the differently-sized tibial surgical broach's 14 has a common anterior/posterior broach taper angle ($\theta_{BroA/P}$), which is the same as the anterior/posterior augment taper angle ($\theta_{AugA/P}$) common to each of the tibial cone augments 12. In the exemplary embodiment described herein, each of the differently-sized tibial surgical broaches has an anterior/posterior broach taper angle of 14° (i.e., $\theta_{BroA/P}$=14°.

Referring now to FIGS. 12-21, the orthopaedic joint replacement system 10 also includes a femoral cone augment 112 and a femoral surgical broach 114 for use in preparing the bone to receive one of the femoral cone augments 112. The femoral cone augment 112 includes an elongated hollow body 116 that is open on its anterior side. The bore 118 defined by the hollow body 116 is sized and shaped to receive a femoral stem component of a femoral revision prosthesis (not shown). Moreover, the size and shape of the bore 118 allow the position of the femoral stem component of the femoral revision prosthesis to be offset in the medial/lateral direction from the center of the augment 112 as needed to fit the needs of a given surgical installation. Moreover, the body 116 has a cutout 120 formed in the posterior side of the femoral cone augment 112. The cutout 120 provides clearance for the box of the revision femoral component.

Like the body 16 of the tibial cone component 12, the body 116 of the femoral cone augment 112 is illustratively embodied as a solid-metal base 132 having a porous-metal coating 130 disposed thereon. The solid-metal base 132 and the porous-metal coating 130 may be embodied and manufactured in a similar manner as to the solid-metal base 32 and the porous metal coating 30 discussed above in regard to the tibial cone component 12, with all such features, methods, starting materials, and alternatives not being repeated herein for purposes of brevity. In the illustrative embodiment described herein, like as was described above in regard to the tibial cone augment 12, the porous-metal coating 130 is disposed on the solid-metal base 132 of the femoral cone augment 112 by virtue of being additively manufactured contemporaneously with the solid-metal base 132 so as to create a common, monolithic component of the two metal structures.

Figure 12:
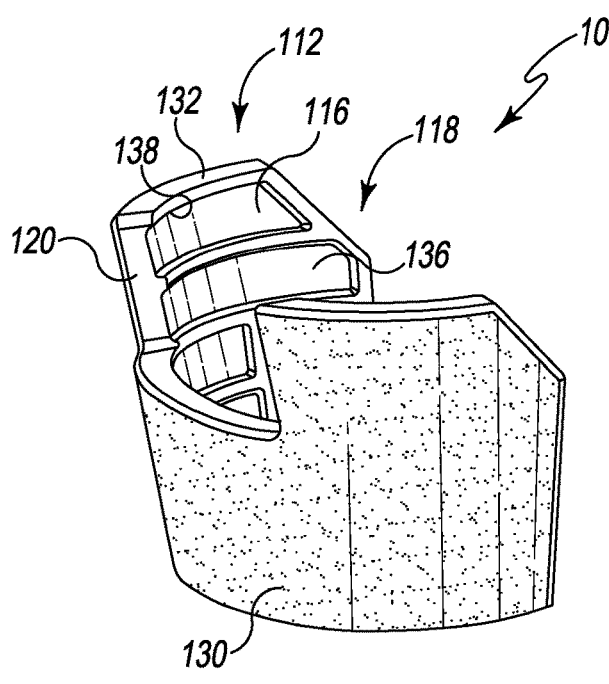
FIG. 12 is perspective view of femoral cone augment for use with a revision knee prosthesis.
Figures 13, 14:
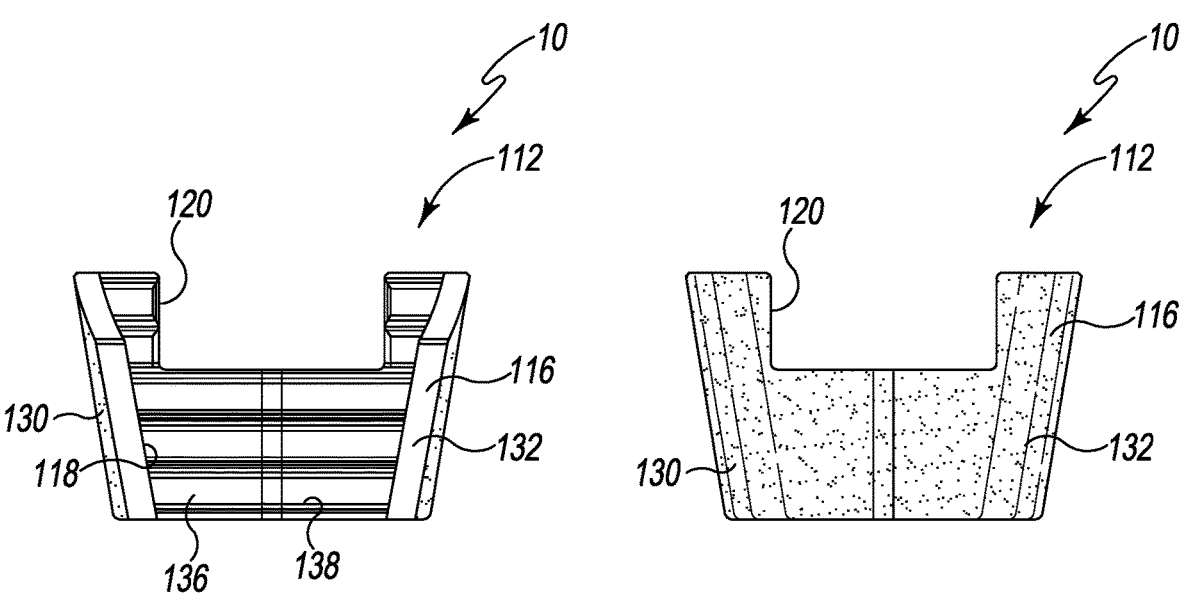
FIG. 13 is an anterior view of the femoral cone augment of FIG. 12.
FIG. 14 is a posterior view of the femoral cone augment of FIG. 12.

As can be seen in FIGS. 12 and 13, the inner sidewall 136 that defines the bore 118 of the hollow body 116 has a number of cement pockets 138 formed therein. Bone cement is received into the cement pockets 138 to increase adhesion of the cement to the femoral cone augment 112 during implantation of the femoral revision prosthesis.

Figure 18:
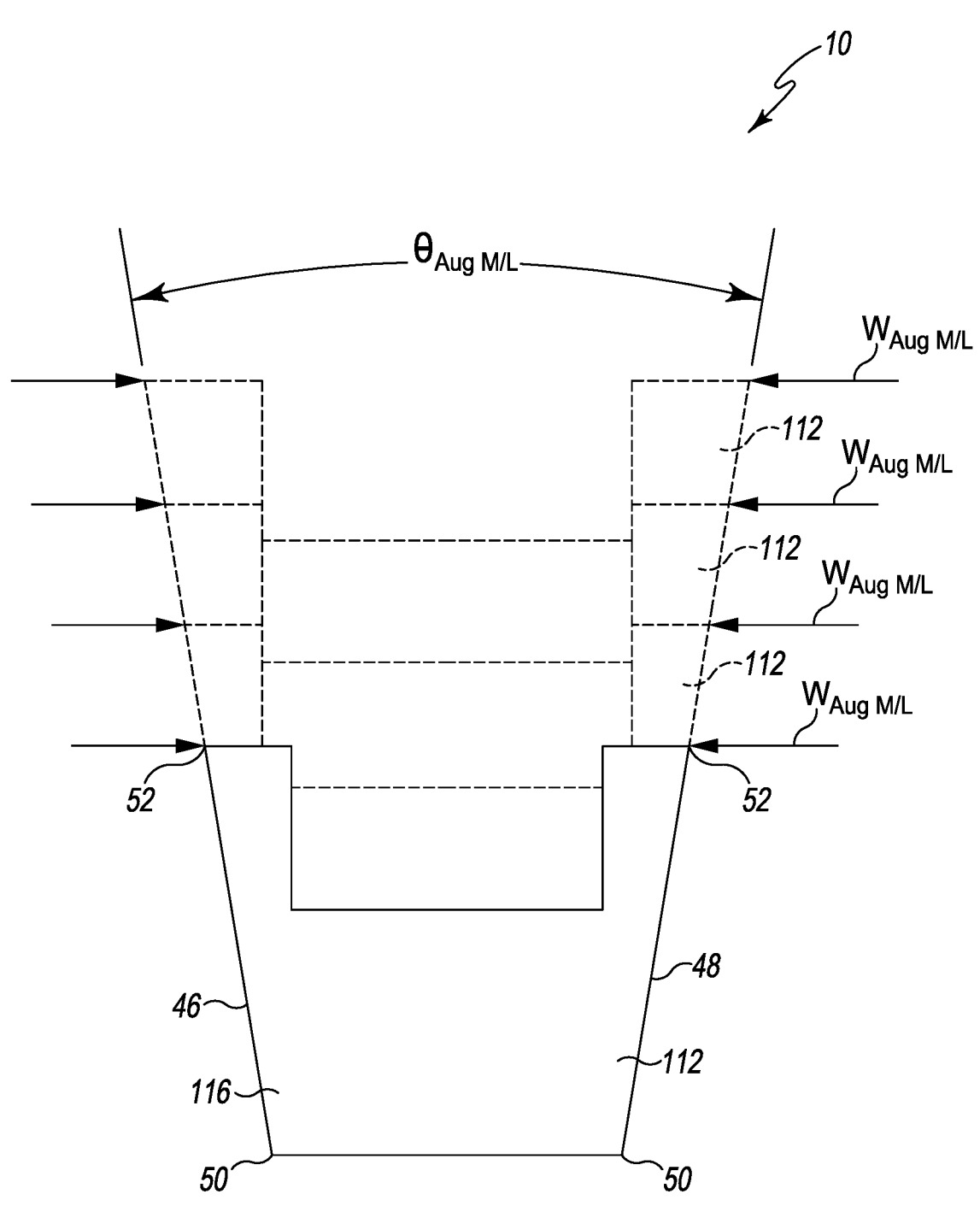
FIG. 18 is a diagrammatic view showing multiple sizes of the femoral cone augment of FIGS. 12-14 superimposed on one another, as viewed in the medial/lateral direction.
Figure 19:
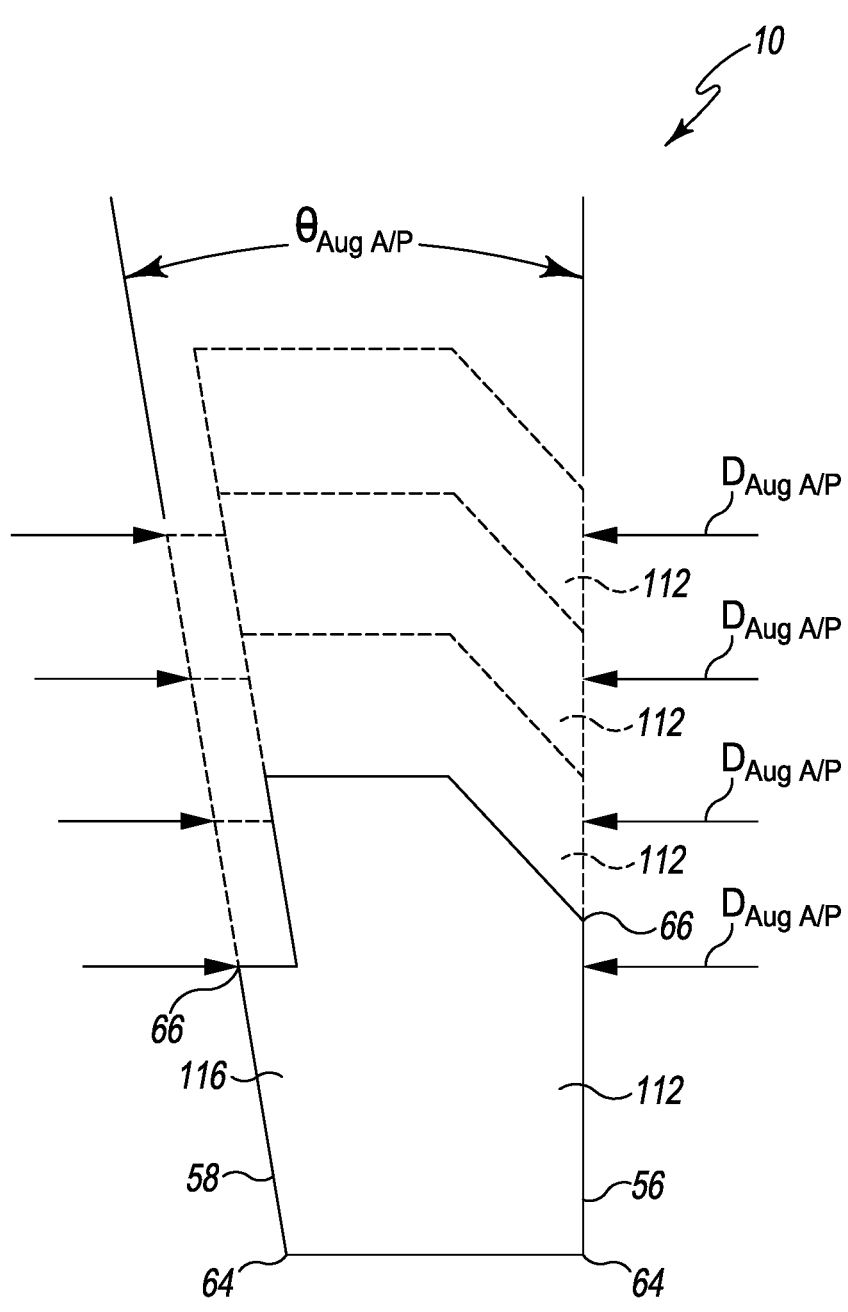
FIG. 19 is a diagrammatic view showing multiple sizes of the femoral cone augment of FIGS. 12-14 superimposed on one another, as viewed in the anterior/posterior direction.

As shown in FIGS. 18 and 19, like the tibial cone augment 12, the femoral cone augment 112 may be provided in a number of different configurations to fit the needs of a given patient's anatomy. In particular, the femoral cone augment 112 may be configured in various different sizes to conform to the patient's anatomy and/or accommodate a wide range of bone loss. In one illustrative embodiment, the femoral cone augment 112 may be provided in four different sizes (e.g., Sizes Small (S), Medium (M), Large (L), Extra Large (XL)), although other sizes (e.g., Size Double Extra Large (XXL)) could also be provided to fit the needs of a given design of the orthopaedic joint replacement system 10. As shown in FIG. 18, the medial/lateral augment width of the body 116 changes as a function of the size of the femoral cone augment 112. As can be seen in FIG. 18, the medial/lateral augment width ($W_{AugM/L}$) of the femoral cone augment 112 increases as the size of the femoral cone augment 112 increases. In other words, a Size M femoral cone augment 112 has a larger medial/lateral width than a Size S femoral cone augment 112, but a smaller medial/lateral width than a Size L (or Size XL) femoral cone augment 112.

However, as also shown in FIG. 18, like the tibial cone augment 12, each of the differently-sized femoral cone augments 112 has a common taper angle in the medial/lateral direction (i.e., a common medial/lateral augment taper angle). Specifically, each of the differently-sized femoral cone augments 112 has a common medial/lateral augment taper angle ($\theta_{AugM/L}$). In the exemplary embodiment described herein, each of the differently-sized femoral cone augments 112 has a medial/lateral augment taper angle of 19° (i.e., $\theta_{AugM/L}$=19°).

As shown in FIG. 19, the anterior/posterior augment depth of the body 116 changes as a function of the size of the femoral cone augment 112. In particular, the anterior/posterior augment depth ($D_{AugA/P}$) of the femoral cone augment 112 increases as the size of the femoral cone augment 112 increases. In other words, a Size M femoral cone augment 112 has a larger anterior/posterior augment depth than a Size S femoral cone augment 112, but a smaller anterior/posterior augment depth than a Size L (or Size XL) femoral cone augment 112.

However, as shown in FIG. 19, each of the differently-sized femoral cone augments 112 has a common taper angle in the anterior/posterior direction (i.e., a common anterior/posterior augment taper angle). Specifically, each of the differently-sized femoral cone augments 112 has a common anterior/posterior augment taper angle ($\theta_{AugA/P}$). In the exemplary embodiment described herein, each of the differently-sized femoral cone augments 112 has an anterior/posterior augment taper angle of 9.5° (i.e., $\theta_{AugA/P}$=9.5°).

Figure 15:
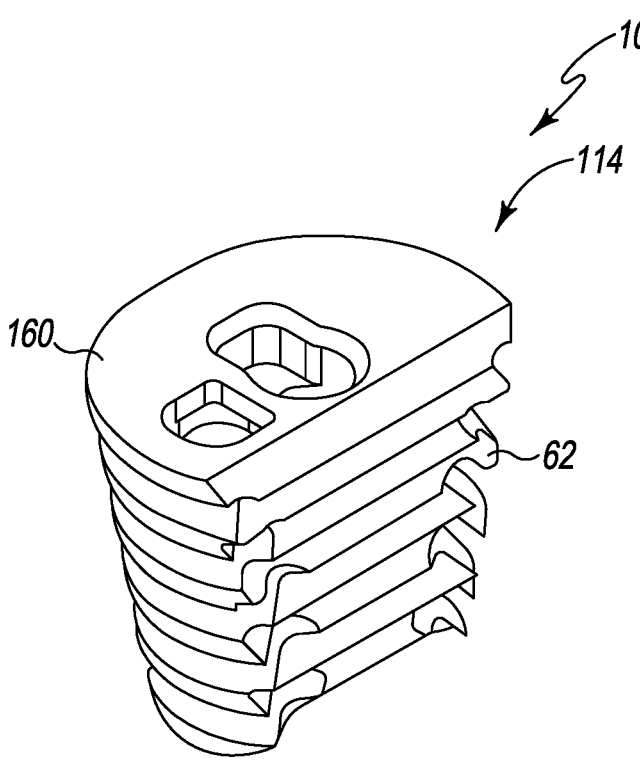
FIG. 15 is a perspective view of a femoral surgical broach for use in an orthopaedic surgical procedure to implant the femoral cone augment of FIGS. 12-14.
Figures 16, 17:
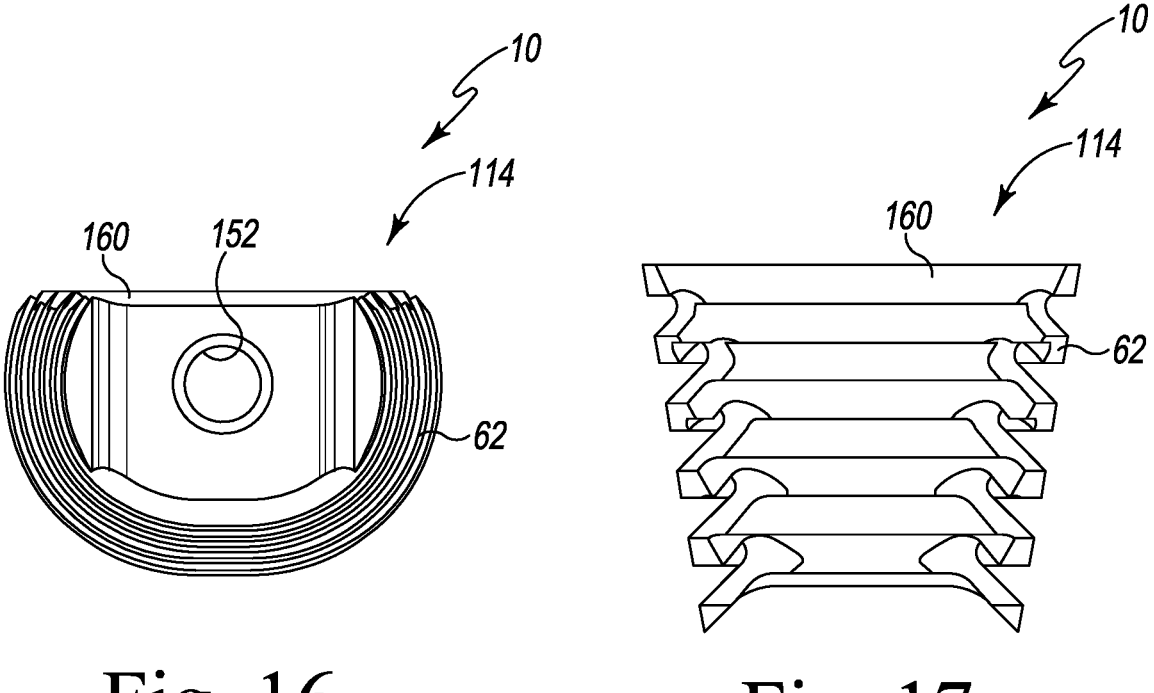
FIG. 16 is an inferior view of the femoral surgical broach of FIG. 15.
FIG. 17 is an anterior view of the femoral surgical broach of FIG. 15.

As shown in FIGS. 15-17, the femoral surgical broach 114 has a geometry that closely corresponds to the geometry of the femoral cone augment 112. In particular, the femoral surgical broach 114 has body 160 that includes a number of cutting teeth 62 that are configured to cut bone tissue in a shape that corresponds to the shape of the femoral cone augment 112. Like the tibial surgical broach 14, in the illustrative embodiment described herein, the femoral surgical broach 114 is constructed with stainless steel. Other suitable materials may be used to fit the needs of a given design of the broach 114.

Figure 20:
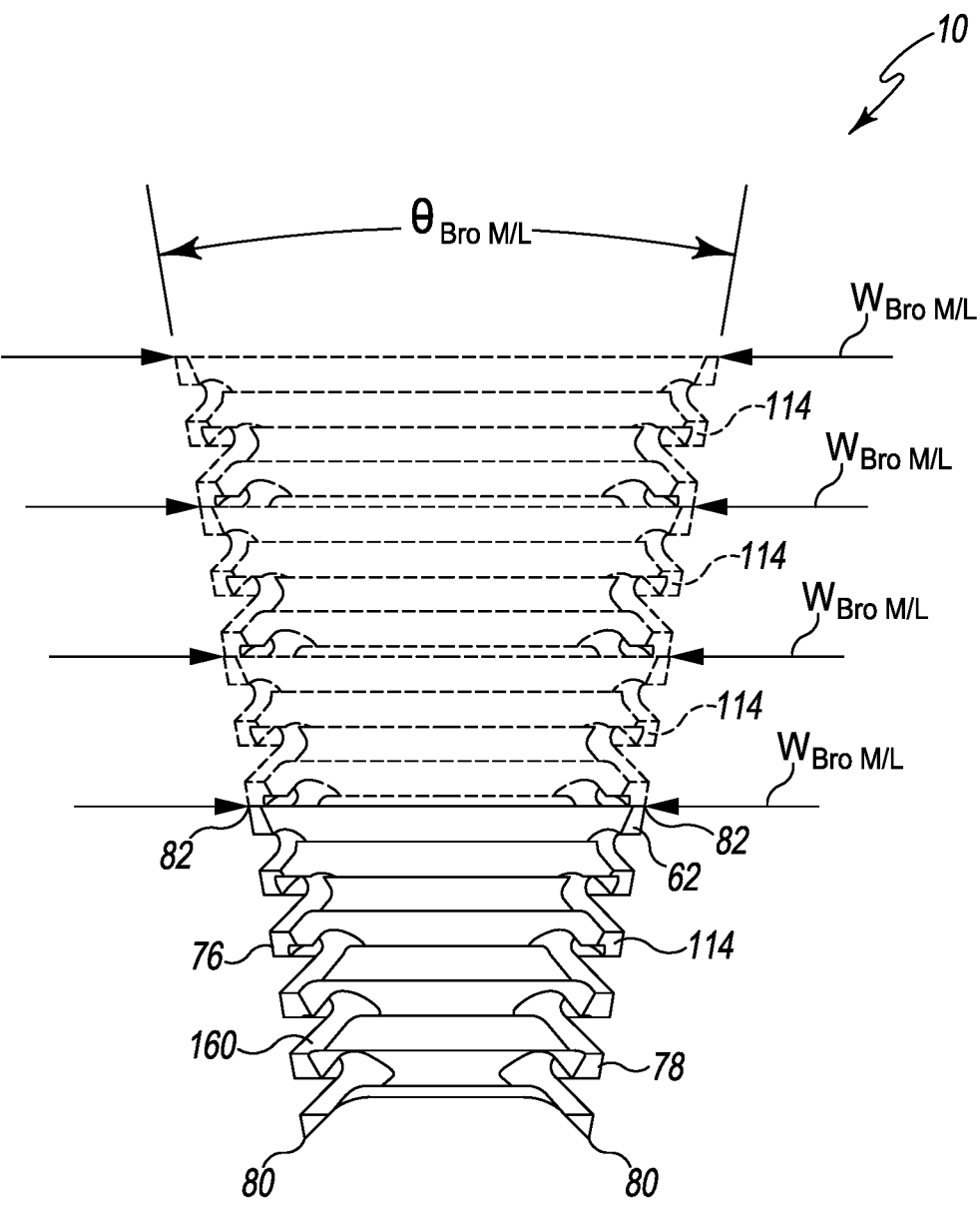
FIG. 20 is a diagrammatic view showing multiple sizes of the femoral surgical broach of FIGS. 15-17 superimposed on one another, as viewed in the medial/lateral direction.
Figure 21:
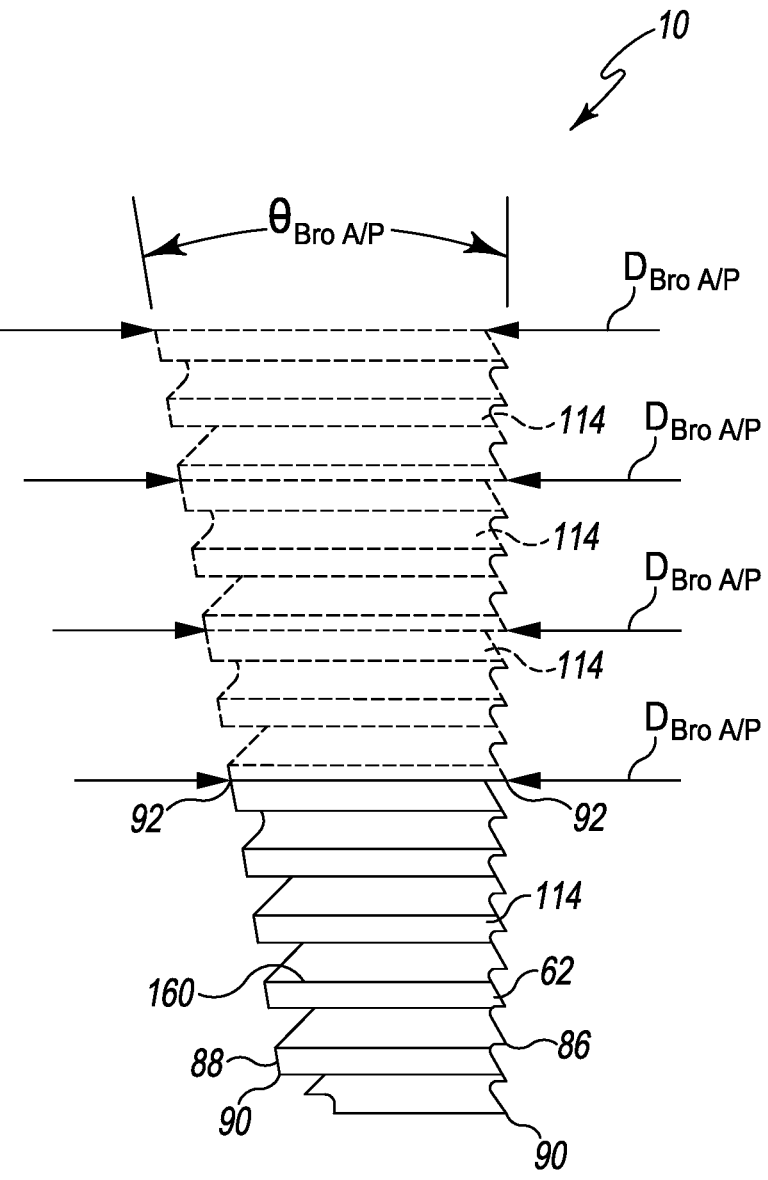
FIG. 21 is a diagrammatic view showing multiple sizes of the femoral surgical broach of FIGS. 15-17 superimposed on one another, as viewed in the anterior/posterior direction.

As shown in FIGS. 20 and 21, the femoral surgical broach 114 may be provided in a number of different configurations to correspond to the different configurations of the femoral cone augment 112. In particular, the femoral surgical broach 114 may be configured in various different sizes to conform to the sizes of the femoral cone augment 112. As such, in one illustrative embodiment, the femoral surgical broach 114 may be provided in four different sizes (e.g., Sizes Small (S), Medium (M), Large (L), Extra Large (XL)), although additional sizes of the femoral surgical broach 114 (e.g., Size Double Extra Large (XXL)) could also be provided if the femoral cone augment 112 is provided in such additional sizes. As shown in FIG. 20, the medial/lateral broach width of the body 160 changes as a function of the size of the femoral surgical broach 114. Specifically, as can be seen in FIG. 20, the medial/lateral broach width ($W_{BroM/L}$) of the femoral surgical broach 114 increases as the size of the femoral surgical broach 114 increases. In other words, a Size M femoral surgical broach 114 has a larger medial/lateral broach width than a Size S femoral surgical broach 114, but a smaller medial/lateral broach width than a Size L (or Size XL) femoral surgical broach 114.

However, like the femoral cone augment 112 and as shown in FIG. 20, each of the differently-sized femoral surgical broaches 114 has a common taper angle in the medial/lateral direction (i.e., a common medial/lateral broach taper angle). Moreover, the medial/lateral broach taper angle of the broach 114 is the same as the medial/lateral augment taper angle of the femoral cone augment 112. Specifically, the medial/later taper angle of the broach 114 matches the medial/lateral taper angle of the augment 112. As such and as can be seen in FIGS. 18 and 20, each of the differently-sized tibial surgical broaches 114 has a common medial/lateral broach taper angle ($\theta_{BroM/L}$), which is the same as the medial/lateral augment taper angle ($\theta_{AugM/L}$) common to each of the femoral cone augments 112. In the exemplary embodiment described herein, each of the differently-sized femoral surgical broaches 114 has a medial/lateral broach taper angle of 19° (i.e., $\theta_{BroM/L}$=19°).

As shown in FIG. 21, the anterior/posterior broach depth of the body 160 changes as a function of the size of the femoral surgical broach 114. Specifically, the anterior/posterior broach depth ($D_{BroA/P}$) of the femoral surgical broach 114 increases as the size of the femoral surgical broach 114 increases. In other words, a Size M femoral surgical broach 114 has a larger anterior/posterior broach depth than a Size S femoral surgical broach 114, but a smaller anterior/posterior augment depth than a Size L (or Size XL) femoral surgical broach 114.

However, as shown in FIG. 21, each of the differently-sized femoral surgical broaches 114 has a common taper angle in the anterior/posterior direction (i.e., a common anterior/posterior broach taper angle). Moreover, the anterior/posterior broach taper angle of the broach 114 is the same as the anterior/posterior augment taper angle of the femoral cone augment 112. Specifically, the anterior/posterior taper angle of the broach 114 matches the anterior/posterior taper angle of the augment 112. As such and as can be seen in FIGS. 19 and 21, each of the differently-sized tibial surgical broaches 114 has a common anterior/posterior broach taper angle ($\theta_{BroA/P}$), which is the same as the anterior/posterior augment taper angle ($\theta_{AugA/P}$) common to each of the femoral cone augments 112. In the exemplary embodiment described herein, each of the differently-sized femoral surgical broaches 114 has an anterior/posterior broach taper angle of 9.5° (i.e., $\theta_{BroA/P}$=9.5°).

As described above, the geometry of the surgical broaches 14, 114 closely corresponds to the geometry of the cone augments 12, 112. Specifically, a common medial/lateral taper angle and a common anterior/posterior taper angle is used between all the different sizes of the tibial surgical broaches 12 and the tibial cone augments 14, with a common medial/lateral taper angle and a common anterior/posterior taper angle also being used between all the different sizes of the femoral surgical broaches 112 and the femoral cone augments 114. Such an arrangement provides for enhanced ease of use during performance of an orthopaedic surgical procedure given it provides for enhanced flexibly in the intra-operative decision making by the surgeon. For example, if during the trialing process, the surgeon determines that the patient's bone was over prepped (i.e., a larger bone cavity was created than needed), the surgeon can simply substitute a larger cone augment than originally planned since the augments all "grow" along the same taper angles throughout the range of sizes. Similarly, in the case of when the surgeon determines that the patient's bone was under prepped (i.e., a smaller bone cavity was created than needed), the surgeon can simply broach the cavity with the next size up broach. Alternatively, the surgeon can also substitute a smaller cone augment than originally planned and simply allow the smaller cone augment to sit a bit deeper in the prepared cavity since the cavity has been broached to common taper angles relative to the entire range of augment sizes. Use of a smaller cone augment sitting deeper in the cavity may be preferred over re-broaching the cavity to a larger size in the case of when the larger broach might be less than ideal due to the anatomy of the patient or the magnitude of bone available in one direction or the other (e.g., the amount of bone available in the anterior/posterior direction may be limited even though ample bone exists for the larger broach in the medial/lateral direction).

As will be described below in greater detail, the surgical broaches 14, 114 are used in combination with a stem trial component 150 to surgically prepare the proximal end of a patient's tibia (in the case of the tibial surgical broach 14) or the distal end of the patient's femur (in the case of the femoral surgical broach 114). As used herein, the term "stem trial component" refers to is an orthopaedic surgical instrument for use by a surgeon in trialing or otherwise assessing the fit of an intramedullary stem component during performance an orthopaedic surgical procedure. As such, it should be appreciated that, as used herein, the term "stem trial component" is distinct from orthopaedic implants or prostheses that are surgically implanted in the body of the patient or other orthopaedic surgical instruments (such as canal reamers, intramedullary rods, etcetera) that are used to perform other functions during an orthopaedic surgical procedure.

As can be seen in FIGS. 6 and 16, the surgical broaches 14, 114 have a threaded bore 152 formed in their respective distal ends 154. The threaded bore 152 is sized to receive a threaded post 154 formed in the proximal end 156 of the stem trial component 150 (the threaded post 154 can be seen, for example, in FIG. 27) so as to selectively secure the stem trial component 150 to the broach 14, 114. In such a way, and as discussed below in more detail, the stem trial component 150 may be used as a guide instrument during use of the broach 14, 114. In doing so, the stem trial component 150 provides an enhanced and simplified approach to guiding the broaching process relative to use of heretofore designed systems which can require complex apparatus to be assembled to the bone.

Figure 22:
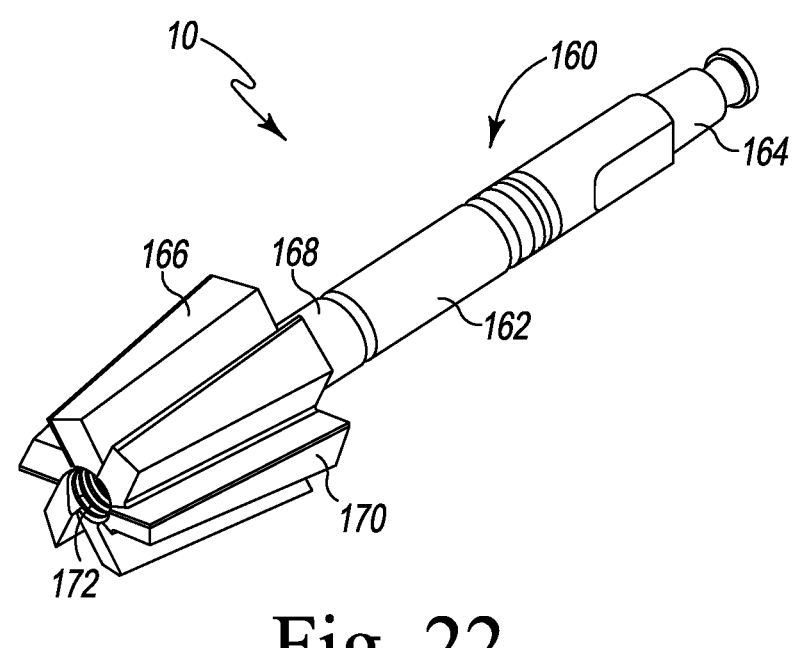
FIG. 22 is a perspective view of a cone reamer.
Figure 23:
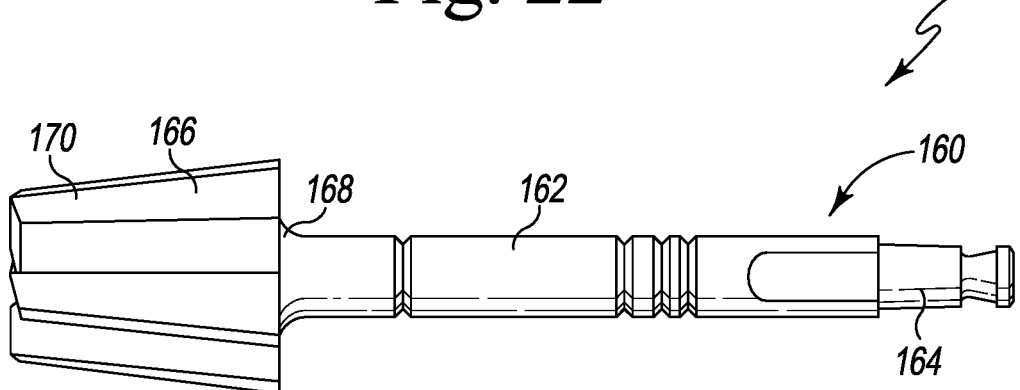
FIG. 23 is a side view of the cone reamer of FIG. 22.
Figure 24:
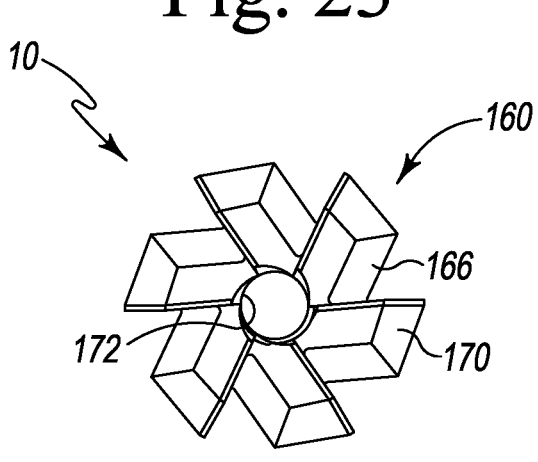
FIG. 24 is an end view of the cone reamer of FIG. 22.

The stem trial component 150 may also be used to guide a cone reamer 160 during a preliminary step in the orthopaedic surgical procedure to implant the cone augments 12, 112. As shown in FIGS. 22-24, the cone reamer 160 includes an elongated shaft 162 having a proximal end 164 that fits into the chuck of a rotary power tool or a manual handle (not shown). The cone reamer 160 also includes a cutting head 166 located at the opposite, distal end 168 of the shaft 162. The cutting head 166 of the cone reamer 160 includes a plurality of helical cutting flutes 170. The cutting head 166 is generally conical in shape. When the cone reamer 160 is positioned in the patient's tibia or femur and rotated, the cutting flutes 170 ream or otherwise cut the bone tissue to form a surgically-prepared cavity to accommodate the geometry of one of the broaches 14, 114. As such, the cone reamer 160 may be used to form an initial surgically-prepared cavity in the patient's bone, with one of the broaches 14, 114 then being used to form the final shape and size of the surgically-prepared cavity.

As shown in FIGS. 22 and 24, the cone reamer 160 has a threaded bore 172 formed in its distal end 168. Like the threaded bores 152 formed in the broaches 14, 114, the threaded bore 172 of the reamer 160 is sized to receive the threaded post 154 formed in the proximal end 156 of the stem trial component 150 so as to selectively secure the stem trial component 150 to the cone reamer 160. In such a way, and as discussed below in more detail, the stem trial component 150 may be used as a guide instrument during use of the cone reamer 160. Like the surgical broaches 14, 114, in the illustrative embodiment described herein, the cone reamer 160 is constructed with stainless steel. Other suitable materials may be used to fit the needs of a given design of the reamer 160.

As described above, the orthopaedic system 10 may be used to surgically-prepare a patient's knee to receive a revision knee prosthesis. In particular, as shown in FIGS.

25-31, the orthopaedic system 10 may be used to surgically prepare a patient's tibia 200 to receive a revision tibial prosthesis. As shown in FIGS. 32-36, the orthopaedic system 10 may also be used to surgically prepare a patient's femur 250 to receive a revision femoral prosthesis.

Figure 25:
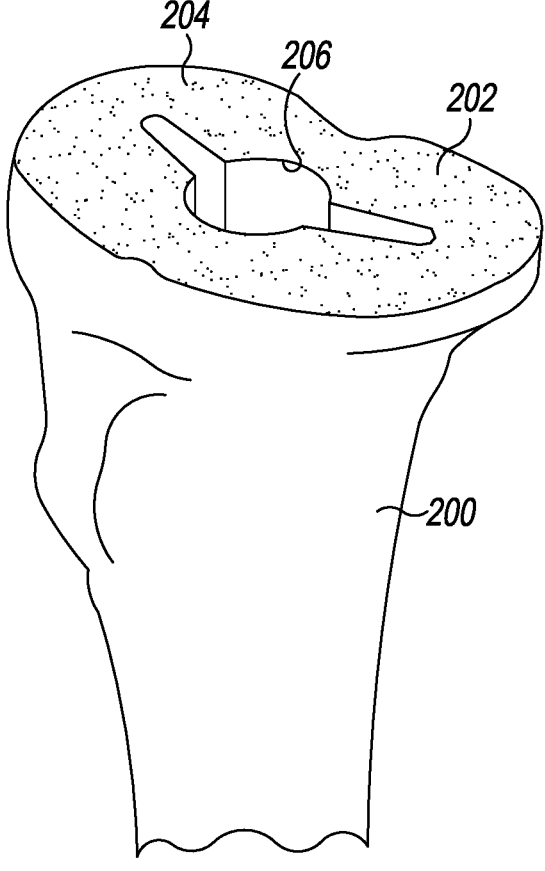
FIGS. 25-31 illustrate a number of steps of a surgical procedure to implant the tibial cone augment of FIGS. 1-4.

As shown in FIG. 25, the orthopaedic system 10 is used in a revision procedure in which a primary tibial implant has been removed from the proximal end 202 of the patient's tibia 200. As shown in FIG. 25, in a revision procedure, the proximal end 202 of the patient's tibia 200 includes a plurality of surfaces that had been previously surgically-shaped to receive the primary implant. During a revision procedure, the proximal end 202 of the patient's tibia 200 is further surgically-resected to prepare the bone to receive a revision tibial prosthesis. FIGS. 25-31 illustrate a number of exemplary steps of a procedure for surgically-preparing the proximal end 202 of the patient's tibia 200 during a revision procedure. It should be appreciated that any surgical procedure may include additional or fewer steps depending on the state of the patient's bony anatomy and the preferences of the surgeon.

Figure 26:
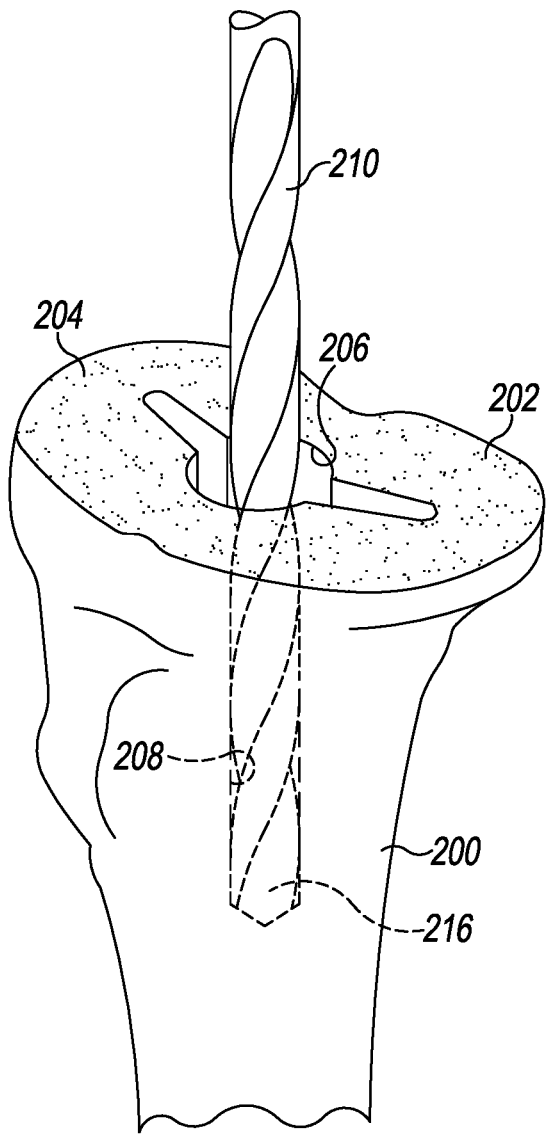

Referring specifically now to FIG. 25, the proximal end 202 of the patient's tibia 200 includes an opening 206 defined in a planar resected surfaces 204. The opening 206 was formed during the previous procedure to implant the primary implant and now permits the surgeon to access the intramedullary canal 208 of the patient's tibia subsequent to removal of the primary implant. With access to the intramedullary canal 208 now achieved, the surgeon then prepares the intramedullary canal 208 of the patient's tibia 200 to receive the stem of a revision tibial prosthesis. To do so, as shown in FIG. 26, the surgeon uses a canal reamer 210 to ream the portion of the patient's intramedullary canal 208 into which the stem component of the tibial revision prosthesis is implanted. To do so, the surgeon inserts the proximal end of the canal reamer 210 into the chuck of the manual handle or a rotary power tool. The surgeon then positions the cutting head 216 of the canal reamer 210 in the intramedullary canal 208 of the patient's tibia 200 and thereafter rotates the cutting head 216 manually (by use of a handle) or under the control of a rotary power tool. Such rotation of the cutting head 216 causes its cutting flutes 218 to ream or otherwise cut the bone tissue of the tibia 200. The canal reamer 210 is driven to a desired depth and then removed.

Figure 27:
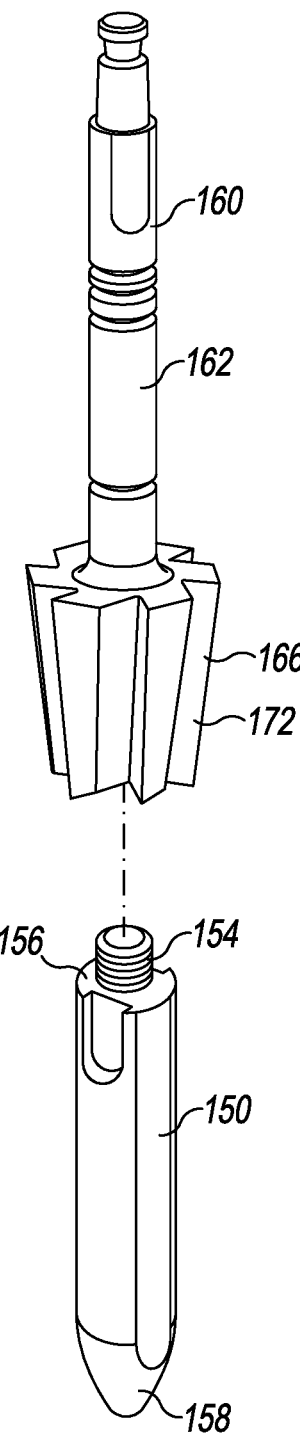
Figure 28:
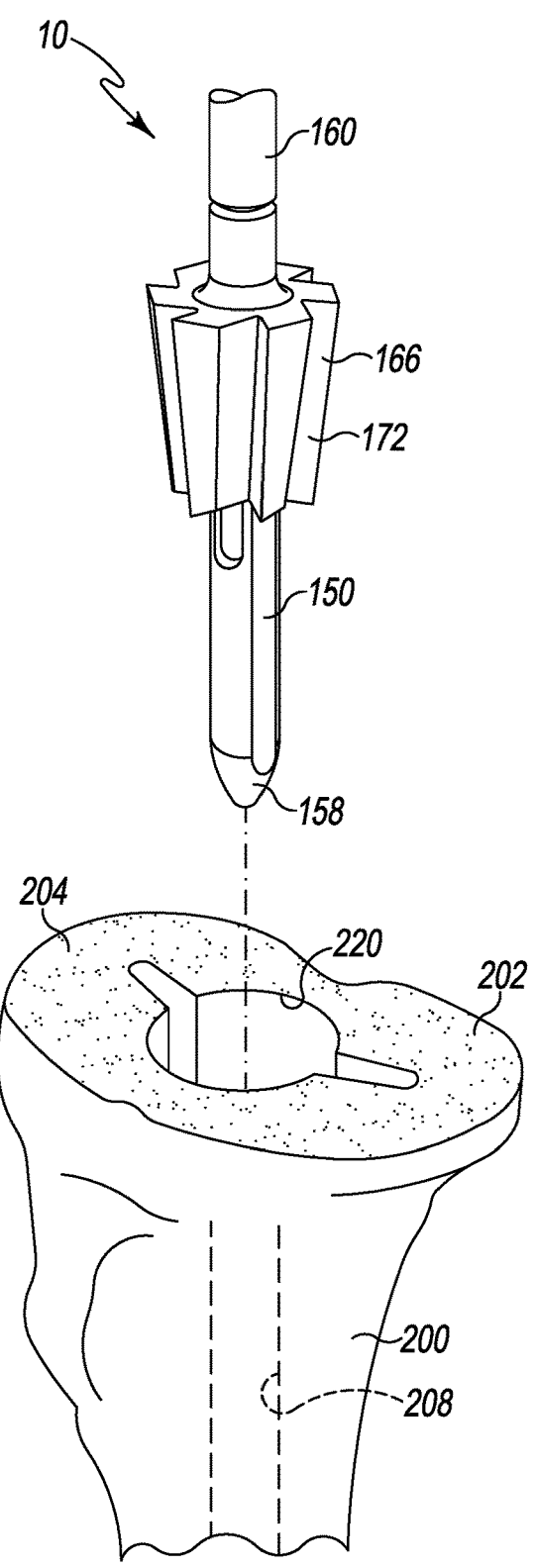

The surgeon then prepares the proximal end 202 of the patient's tibia 200 to receive one of the tibial cone augments 12. To do so, the surgeon first reams a starter cavity 220 in the proximal end 202 of the patient's tibia 200. As shown in FIGS. 27 and 28, the surgeon installs the stem trial component 150 on the cone reamer 160 by threading the stem's threaded post 154 into the threaded bore 172 formed in the distal end 168 of the reamer 160. It should be appreciated that the surgeon selects a stem trial component 150 that has a diameter that closely matches the diameter of the canal reamer 210 previously used to ream the patient's intramedullary canal 208 such that the stem trial component 150 forms a substantially tight fit within the reamed canal 208. In such a way, the stem trial component 150 is tightly captured within the reamed intramedullary canal 208 and, as a result, functions as a guide instrument for the cone reamer 160 so as to maintain the rotary axis of the reamer 160 in alignment with the center of the reamed intramedullary canal 208.

With the stem trial component 150 attached to the cone reamer 160, the surgeon inserts the proximal end of the cone reamer 160 into the chuck of the manual handle or a rotary power tool. The surgeon then advances the distal end 158 of the stem trial component 150 into the intramedullary canal 208 of the patient's tibia 200 and thereafter rotates the cutting head 166 (and hence the stem trial component 150 secured thereto) manually (by use of a handle) or under the control of a rotary power tool. Such rotation of the cutting head 166 causes its cutting flutes 170 to ream or otherwise cut the bone tissue of the proximal end 202 of the tibia 200 so as to form a reamed starter cavity 220 therein. The cone reamer 160 is driven to a desired depth—typically when the proximal end of the reamer's cutting head 166 is flush with the planar surface 204 of the proximal end 202 of the tibia 200—and is thereafter removed.

Figure 29:
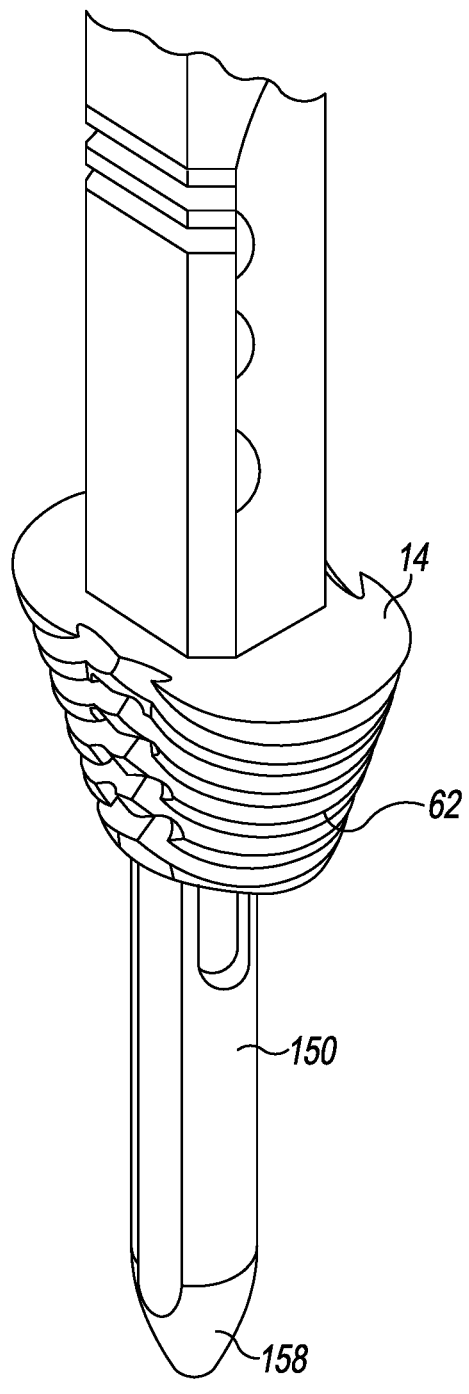
Figure 30:
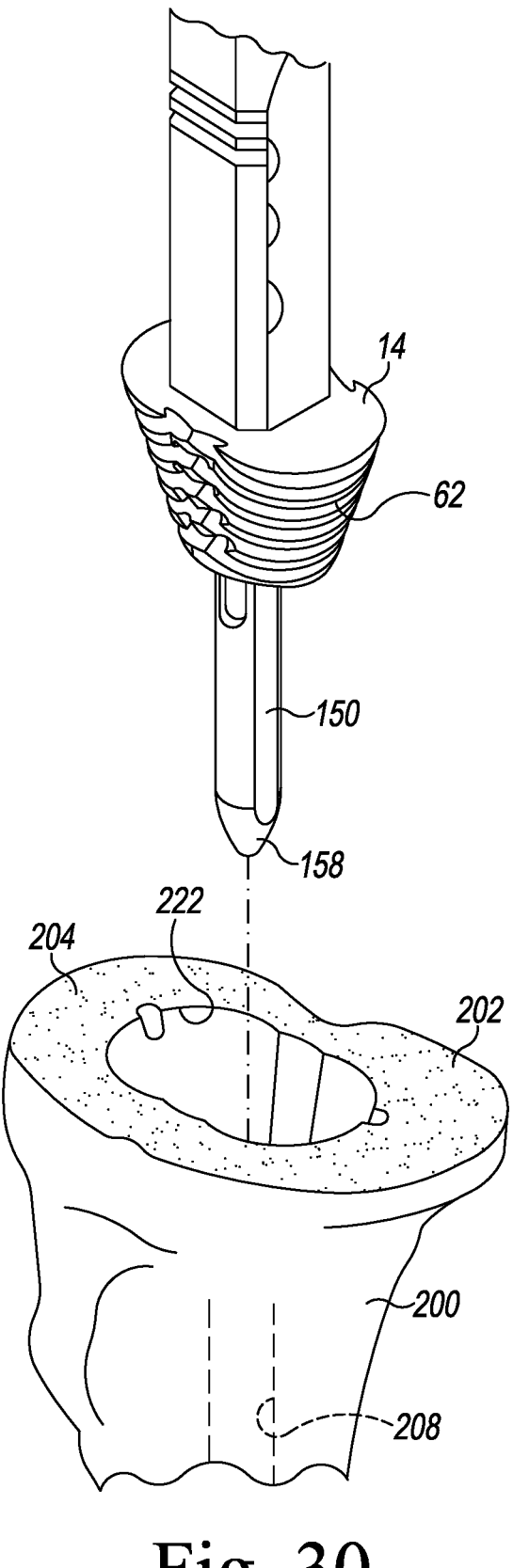

The surgeon then broaches a finished cavity 222 in the proximal end 202 of the patient's tibia 200. As shown in FIGS. 29 and 30, the surgeon installs the stem trial component 150 on the tibial surgical broach 14 by threading the stem's threaded post 154 into the threaded bore 152 formed in the distal end 154 of the tibial surgical broach 14. It should be appreciated that because the stem trial component 150 has a diameter that closely matches the diameter of the canal reamer 210, and thus is tightly captured within the reamed intramedullary canal 208, the stem trial component 150 functions a guide instrument for the tibial surgical broach 14 by maintaining the center of the broach's central lobe section 70 in alignment with the center of the reamed intramedullary canal 208.

With the stem trial component 150 attached to the tibial surgical broach 14, the surgeon then advances the distal end 158 of the stem trial component 150 into the intramedullary canal 208 of the patient's tibia 200. The surgeon continues to advance the broach 14 such that its cutting teeth 62 broach or otherwise cut the bone tissue of the proximal end 202 of the tibia 200 into a shape that corresponds to the shape of the tibial cone augment 12 so as to form the broached finished cavity 222 therein. Thereafter, the broach 14 and stem trial component 150 are removed.

Figure 31:
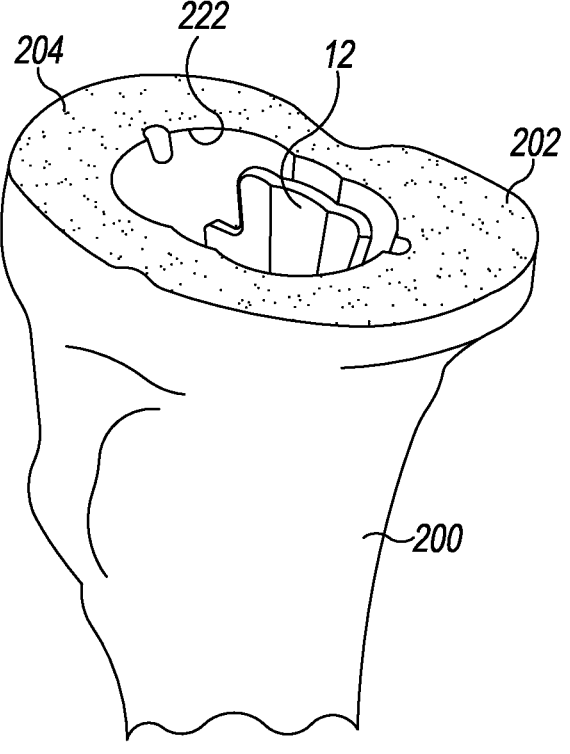

Once the finished cavity 222 has been broached, the tibial cone augment 12 is implanted, as shown in FIG. 31. As discussed above, if the surgeon determines that the patient's bone was over prepped (i.e., a larger finished cavity 222 was created than needed), the surgeon can simply substitute a larger tibial cone augment 12 than originally planned since the augments all "grow" along the same taper angles throughout the range of sizes. Similarly, in the case of when the surgeon determines that the patient's bone was under prepped (i.e., a smaller finished cavity 222 was created than needed), the surgeon can simply broach the cavity with the next size up broach 14. Alternatively, the surgeon can also substitute a smaller tibial cone augment 12 than originally planned and simply allow the smaller cone augment to sit a bit deeper in the prepared finished cavity 222 since the cavity 222 has been broached to common taper angles relative to the entire range of tibial cone augment sizes. Use of a smaller tibial cone augment 12 sitting deeper in the cavity 222 may be preferred over re-broaching the cavity to a larger size in the case of when the larger broach might be less than ideal due to the anatomy of the patient's tibia 200 or the magnitude of bone available in one direction or the other (e.g., the amount of bone available in the anterior/posterior direction may be limited even though ample bone exists for the larger broach in the medial/lateral direction).

Once the surgeon has implanted the desired size of the tibial cone augment 12, the surgeon may then implant a revision tibial prosthesis by installing its stem component through the tibial cone augment and thereafter cementing it in place within the bone.

Figure 32:
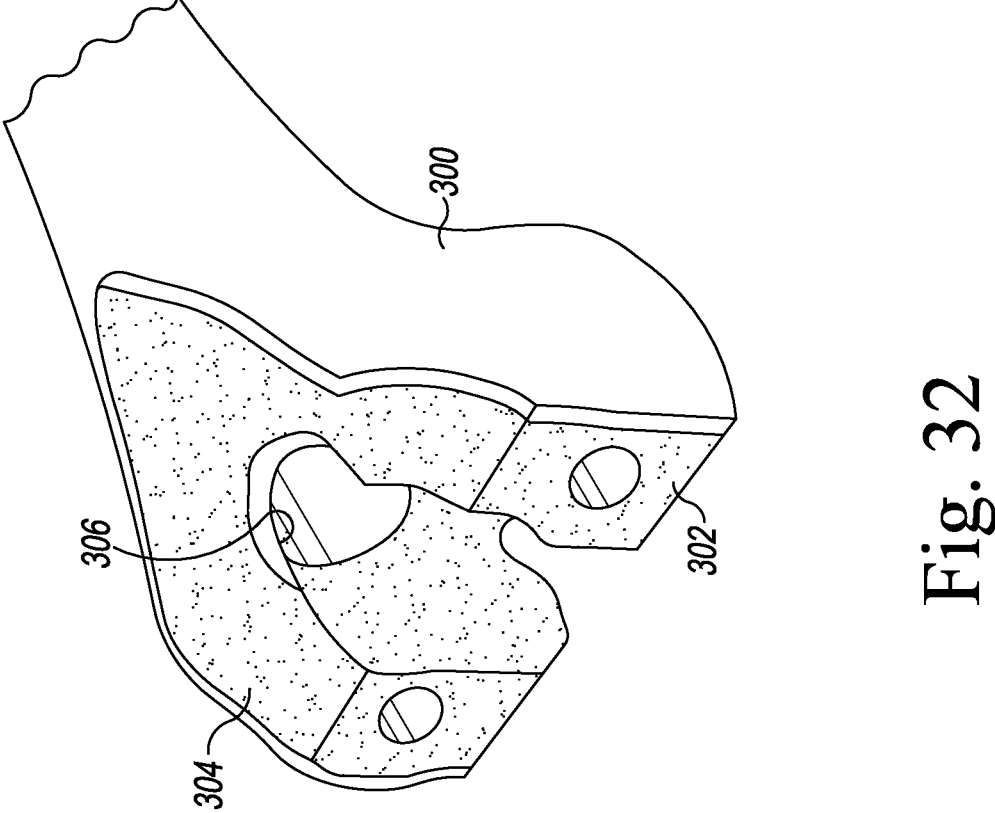
FIGS. 32-36 illustrate a number of steps of a surgical procedure to implant the femoral cone augment of FIGS. 12-14.

As illustrated in FIGS. 32-36, the orthopaedic system 10 may also be used to surgically prepare a patient's femur 300 to receive a revision femoral prosthesis. As shown in FIG. 32, the orthopaedic system 10 is used in a revision procedure in which a primary femoral implant has been removed from the distal end 302 of the patient's femur 300. In a femoral revision procedure, the distal end 302 of the patient's femur 300 includes a plurality of surfaces that had been previously surgically-shaped to receive the primary implant. During a revision procedure, the distal end 302 of the patient's femur 300 is further surgically-resected to prepare the bone to receive a revision femoral prosthesis. FIGS. 32-36 illustrate a number of exemplary steps of a procedure for surgically-preparing the distal end 302 of the patient's femur 300 during a revision procedure. It should be appreciated that any surgical procedure may include additional or fewer steps depending on the state of the patient's bony anatomy and the preferences of the surgeon.

Figure 33:
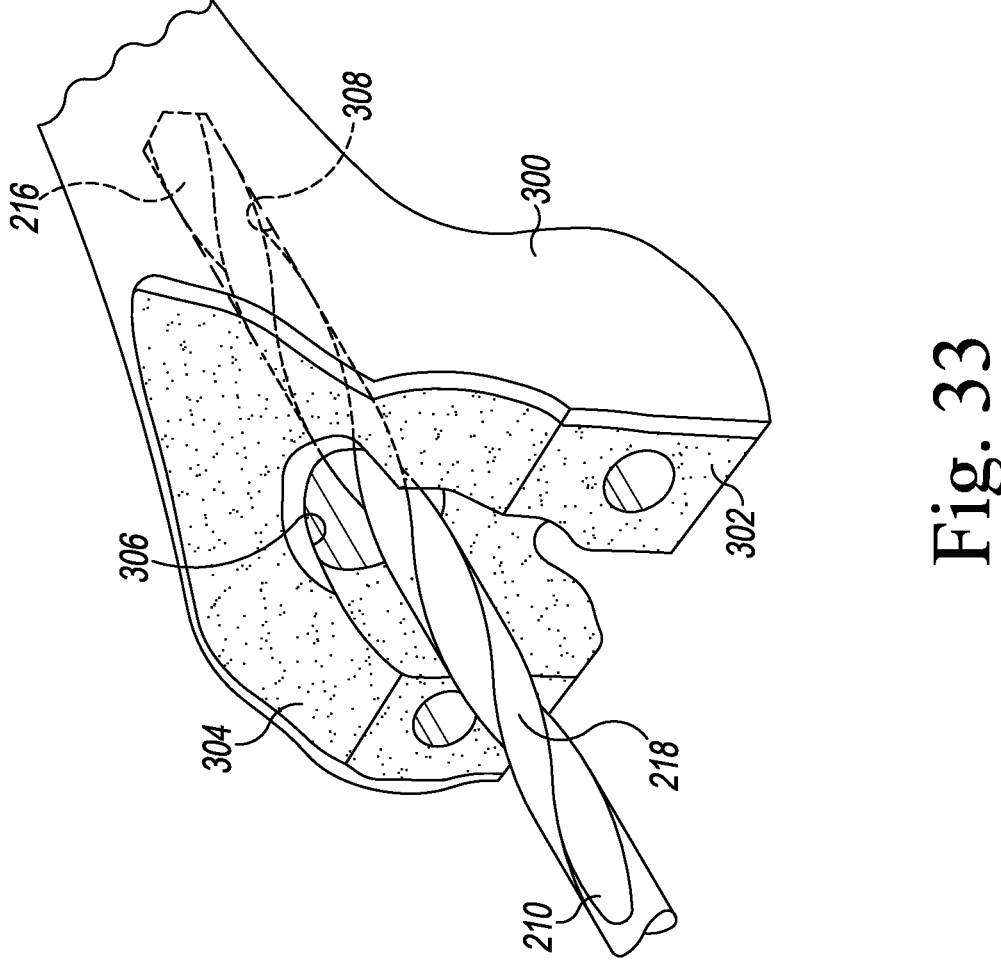

Referring now to FIG. 32, the distal end 302 of the patient's femur 300 includes an opening 306 defined in the resected surfaces 304. The opening 306 was formed during the previous procedure to implant the primary implant and now permits the surgeon to access the intramedullary canal 308 of the patient's femur subsequent to removal of the primary implant. With access to the intramedullary canal 308 achieved, the surgeon then prepares the intramedullary canal 308 of the patient's femur 300 to receive the stem of a revision femoral prosthesis. To do so, as shown in FIG. 33, the surgeon uses the canal reamer 210 to ream the portion of the patient's intramedullary canal 308 into which the stem component of the femoral revision prosthesis is implanted. It should be appreciated that the canal reamer 210 used by the surgeon to ream the femur 300 may, in practice, be embodied differently than the canal reamer 210 used to ream the patient's tibia 200. In any event, the surgeon inserts the proximal end of the canal reamer 210 into the chuck of the manual handle or a rotary power tool. The surgeon then positions the cutting head 216 of the canal reamer 210 in the intramedullary canal 308 of the patient's femur 300 and thereafter rotates the cutting head 216 manually (by use of a handle) or under the control of a rotary power tool. Such rotation of the cutting head 216 causes its cutting flutes 218 to ream or otherwise cut the bone tissue of the femur 300. The canal reamer 210 is driven to a desired depth and then removed.

Figure 34:
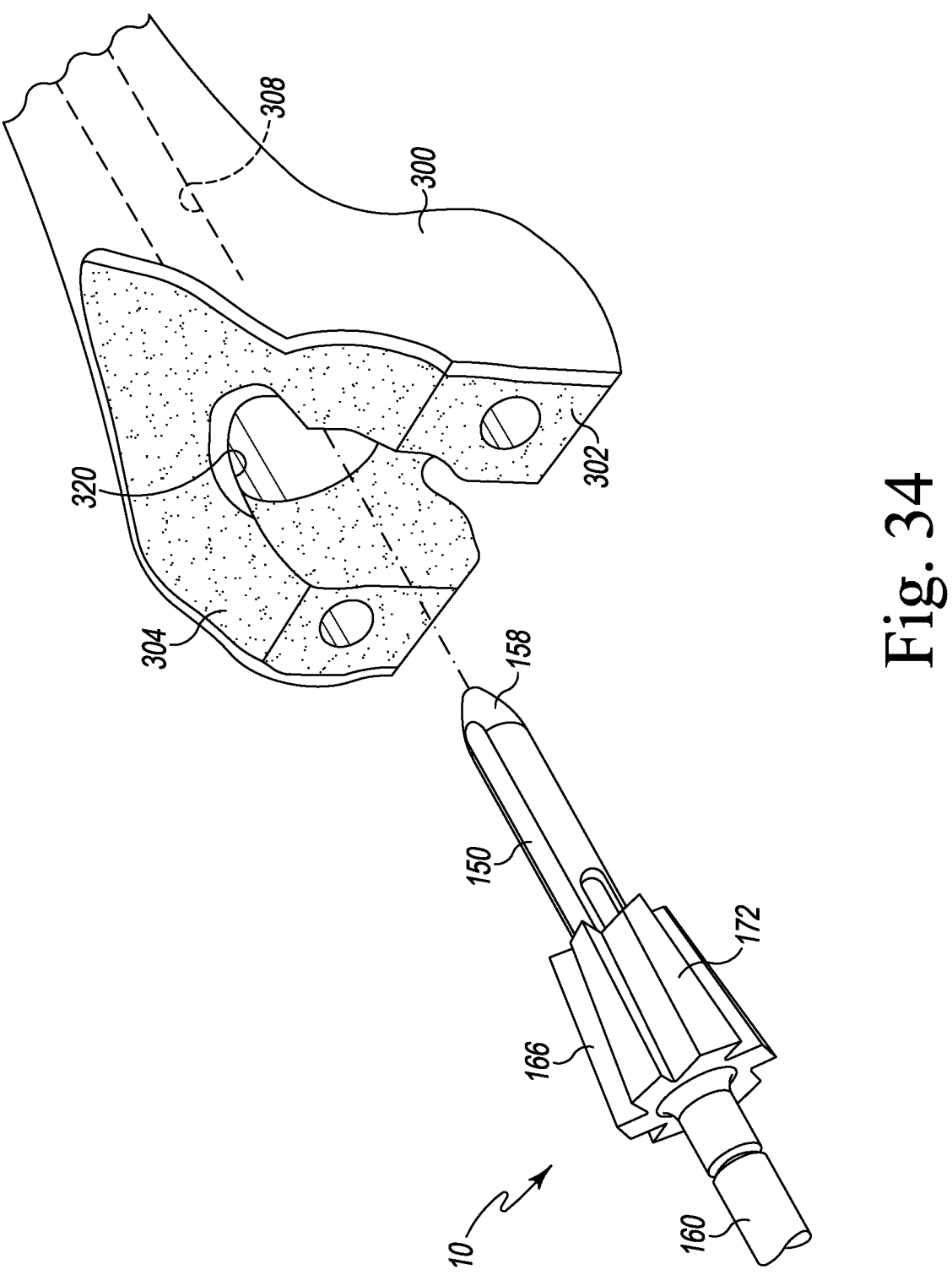

The surgeon then prepares the distal end 302 of the patient's femur 300 to receive one of the femoral cone augments 112. To do so, the surgeon first reams a starter cavity 320 in the distal end 302 of the patient's femur 300. As shown in FIG. 34, the surgeon installs the stem trial component 150 on the cone reamer 160 by threading the stem's threaded post 154 into the threaded bore 172 formed in the distal end 168 of the reamer 160. It should be appreciated that the surgeon selects a stem trial component 150 that has a diameter that closely matches the diameter of the canal reamer 210 previously used to ream the patient's intramedullary canal 308 such that the stem trial component 150 forms a substantially tight fit within the reamed canal 308. In such a way, the stem trial component 150 is tightly captured within the reamed intramedullary canal 308 and, as a result, functions as a guide instrument for the cone reamer 160 so as to maintain the rotary axis of the reamer 160 in alignment with the center of the reamed intramedullary canal 308.

With the stem trial component 150 attached to the cone reamer 160, the surgeon inserts the proximal end of the cone reamer 160 into the chuck of the manual handle or a rotary power tool. The surgeon then advances the distal end 158 of the stem trial component 150 into the intramedullary canal 308 of the patient's femur 300 and thereafter rotates the cutting head 166 (and hence the stem trial component 150 secured thereto) manually (by use of a handle) or under the control of a rotary power tool. Such rotation of the cutting head 166 causes its cutting flutes 170 to ream or otherwise cut the bone tissue of the distal end 302 of the femur 300 so as to form a reamed starter cavity 320 therein. The cone reamer 160 is driven to a desired depth and is thereafter removed.

Figure 35:

The surgeon then broaches a finished cavity 322 in the distal end 302 of the patient's femur 300. As shown in FIGS. 35, the surgeon installs the stem trial component 150 on the femoral surgical broach 114 by threading the stem's threaded post 154 into the threaded bore 152 formed in the distal end 154 of the femoral surgical broach 114. It should be appreciated that because the stem trial component 150 has a diameter that closely matches the diameter of the canal reamer 210, and thus is tightly captured within the reamed intramedullary canal 308, the stem trial component 150 functions a guide instrument for the femoral surgical broach 114 by maintaining the broach in a desired alignment relative to the center of the reamed intramedullary canal 308.

With the stem trial component 150 attached to the femoral surgical broach 114, the surgeon then advances the distal end 158 of the stem trial component 150 into the intramedullary canal 308 of the patient's femur 300. The surgeon continues to advance the broach 114 such that its cutting teeth 62 broach or otherwise cut the bone tissue of the distal end 302 of the femur 300 into a shape that corresponds to the shape of the femoral cone augment 112 thereby forming the broached finished cavity 322. Thereafter, the broach 114 and stem trial component 150 are removed.

Figure 36:
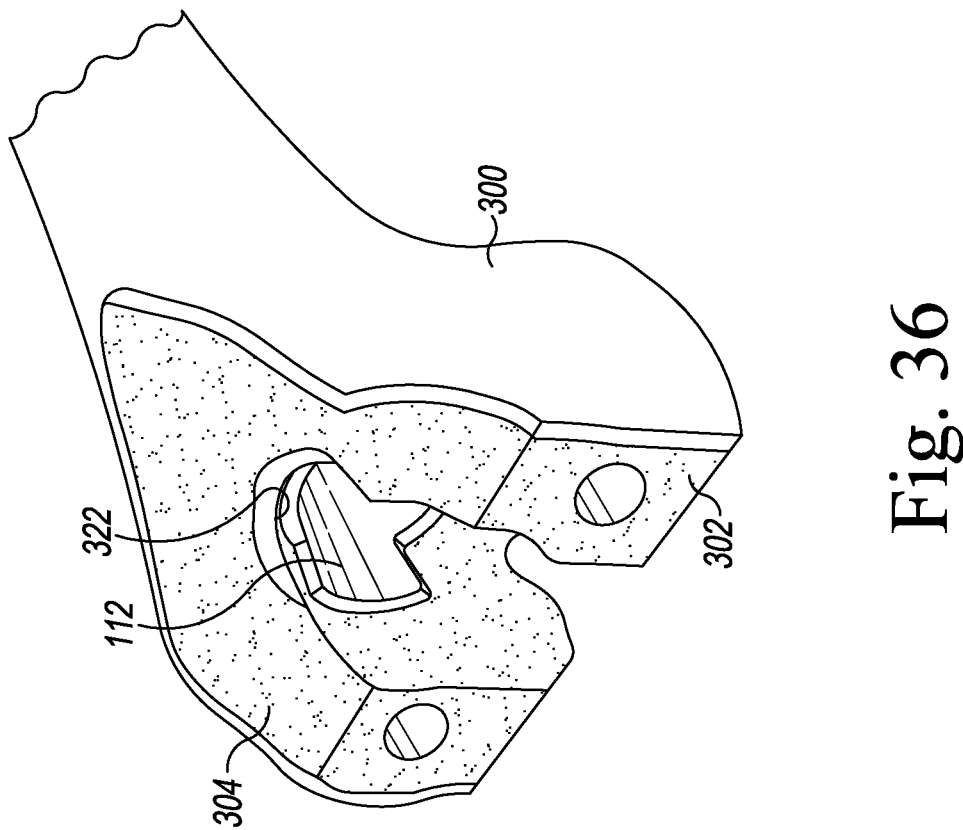

Once the finished cavity 322 has been broached, the femoral cone augment 112 is implanted, as shown in FIG. 36. As discussed above, if the surgeon determines that the patient's bone was over prepped (i.e., a larger finished cavity 322 was created than needed), the surgeon can simply substitute a larger femoral cone augment 112 than originally planned since the augments all "grow" along the same taper angles throughout the range of sizes. Similarly, in the case of when the surgeon determines that the patient's bone was under prepped (i.e., a smaller finished cavity 322 was created than needed), the surgeon can simply broach the cavity with the next size up broach 114. Alternatively, the surgeon can also substitute a smaller femoral cone augment 112 than originally planned and simply allow the smaller cone augment to sit a bit deeper in the prepared finished cavity 322 since the cavity 322 has been broached to common taper angles relative to the entire range of femoral cone augment sizes. Use of a smaller femoral cone augment 112 sitting deeper in the cavity 322 may be preferred over re-broaching the cavity to a larger size in the case of when the larger broach might be less than ideal due to the anatomy of the patient's femur 300 or the magnitude of bone available in one direction or the other (e.g., the amount of bone available in the anterior/posterior direction may be limited even though ample bone exists for the larger broach in the medial/lateral direction).

Once the surgeon has implanted the desired size of the femoral cone augment 112, the surgeon may then implant a revision femoral prosthesis by installing its stem component through the femoral cone augment and thereafter cementing it in place within the bone.

Referring now to FIGS. 37-41, there is shown another embodiment of a tibial cone augment. In particular, there is shown a modular tibial cone augment 400. Like the other tibial cone augments 12 described herein, the modular tibial cone augment 400 is configured to be implanted into a surgically-prepared cavity in the proximal end of the tibia of a patient so as to facilitate implantation of a revision tibial prosthesis.

The modular tibial cone augment 400 includes separate components which may be assembled to one another in various arrangements to create an implant of a desired configuration. In particular, the modular tibial cone augment 400 includes a central lobe component 402, a medial lobe component 404, and a lateral lobe component 406. In such a way, the modular tibial cone augment 400 may be assembled as a tri-lobe tibial augment (i.e., it has all three lobe components 402, 404, 406), a bi-lobe tibial augment (i.e., it has a central lobe component 402 and only one of the medial lobe component 404 or the lateral lobe component 406, but not both) or a concentric tibial augment (i.e., it has a central lobe component 402, but neither the medial lobe component 404 nor the lateral lobe component 406).

Figure 37:
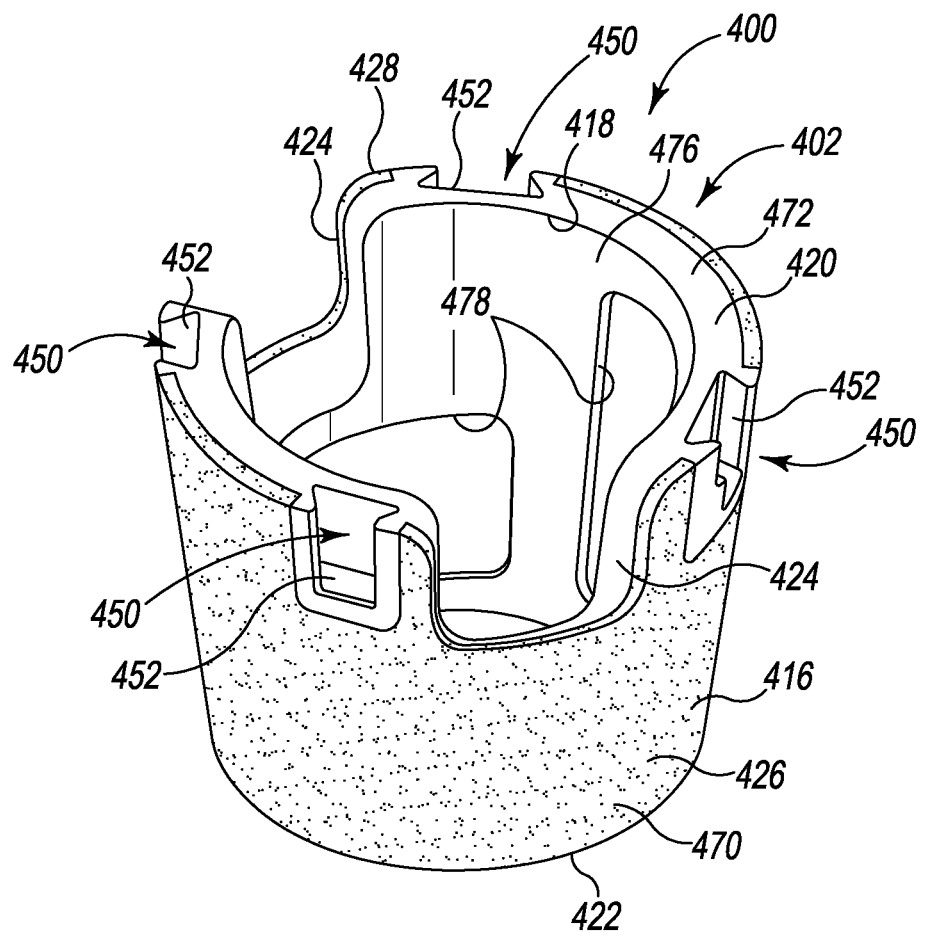
FIG. 37 is a perspective view of a central lobe component of a modular tibial cone augment.

As shown in FIG. 37, the central lobe component 402 includes a round, concentrically-shaped elongated hollow body 416 that is tapered downwardly from its superior end 420 to its inferior end 422. The central lobe component 402 also includes a bore 418 extending therethrough in the superior/inferior direction. The bore 418 is sized and shaped to receive a tibial stem component of a tibial revision prosthesis. As can be seen in FIG. 37, the body 416 of the central lobe component 402 has a cutout 424 formed on both its medial side 426 and its lateral side 428. The cutouts 424 allow for receipt of structures on the inferior side of a revision tibial tray such as one or more keels.

Figure 38:
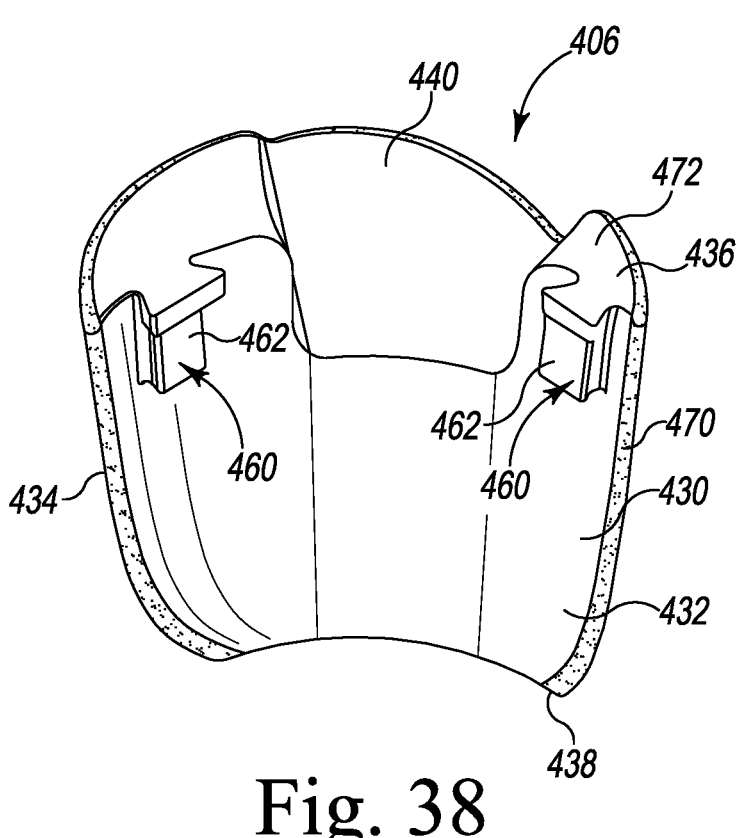
FIG. 38 is a perspective view of a lateral lobe component of a modular tibial cone augment.
Figure 39:
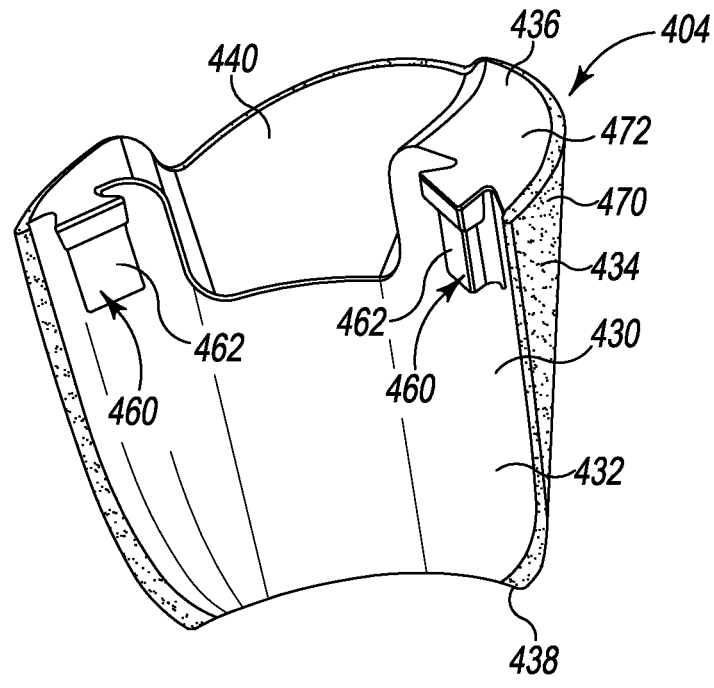
FIG. 39 is a perspective view of a medial lobe component of a modular tibial cone augment.
Figure 40:
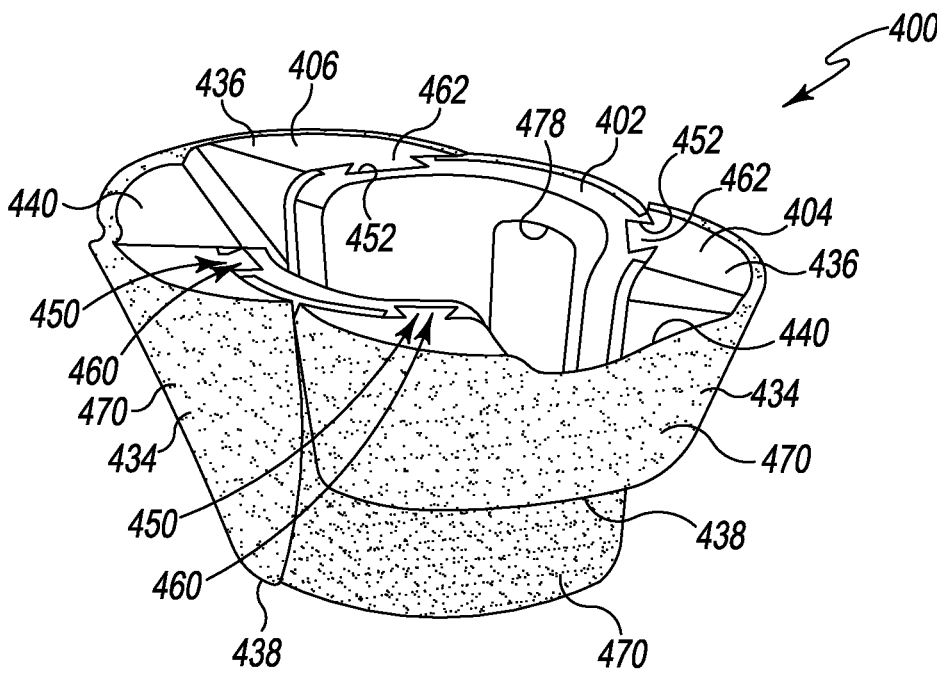
FIG. 40 is a perspective view showing the lobe components of FIGS. 37-39 assembled as a modular tri-lobe tibial cone augment.

As shown in FIGS. 38 and 39, both of the medial lobe component 404 and the lateral lobe component 406 have a body 430 that includes a curved inner sidewall 432 that corresponds in shape to the outer surface of the central lobe component 402. As such, when it is secured to the central lobe component 402, the inner sidewall 432 of the medial lobe component 404 corresponds in shape with the medial side 426 of the central lobe component's body 416. Similarly, when it is secured to the central lobe component 402, the inner sidewall 432 of the lateral lobe component 406 corresponds in shape with the lateral side 428 of the central lobe component's body 416. As can be seen in FIGS. 38-40, the medial lobe component 404 and the lateral lobe component 406 include a curved outer surface 434 that tapers downwardly from the component's superior end 436 to its inferior end 438. In such a way, the inferior end 438 of the side components 404, 406 blends into the outer surface of the central lobe component 402 when secured thereto.

Figure 41:
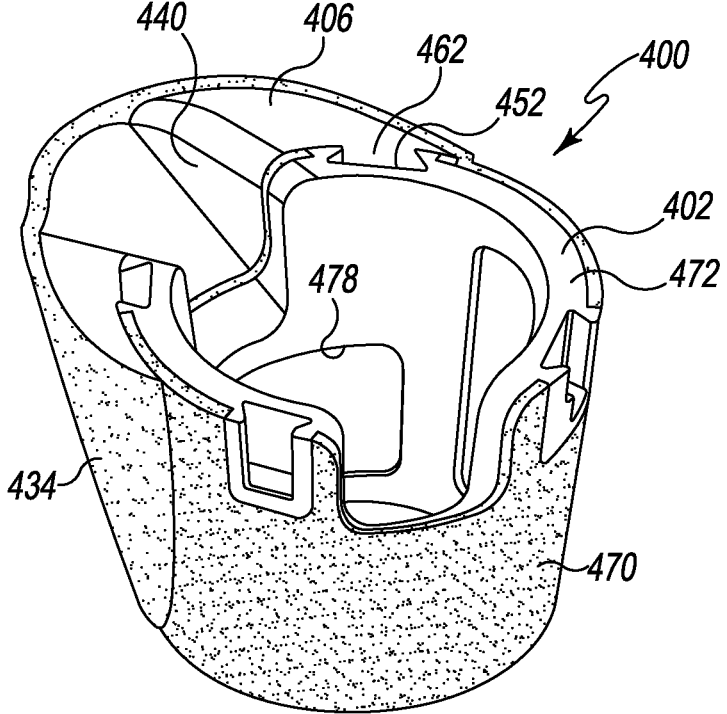
FIG. 41 is a perspective view showing the lobe components of FIGS. 37 and 38 assembled as a modular bi-lobe tibial cone augment.

It should be appreciated that the side lobe components 404, 406 may be provided in a wide variety of geometries. In particular, the side lobe components 404, 406 may be provided in a wide range of widths, lengths, curvatures, etcetera to produce a wide range of options for a surgeon to customize the geometry of an assembled modular tibial cone augment 400. In such a way, the surgeon can use the modular tibial cone augment 400 to accommodate varying degrees of bone loss and/or varying patient anatomies The surface defining the superior end 436 of both the medial lobe component 404 and the lateral lobe component 406 has a recess 440 formed therein. As can be seen in FIGS. 40 and 41, the recesses 440 align with the cutouts 424 formed in the central lobe component 402 when either or both of the medial lobe component 404 and the lateral lobe component 406 are secured to the central lobe component 402. The recesses 440 cooperate with the cutouts 424 to allow for receipt of structures on the inferior side of a revision tibial tray such as one or more keels.

As can be seen in FIG. 37, the central lobe component 402 has a connector 450 formed on both its medial side 426 and its lateral side 428. The connectors 450 mate with connectors 460 formed in the medial lobe component 404 and the lateral lobe component 406 to allow one or both of the components 404, 406 to be secured to the central lobe component 402 during assembly of the modular tibial cone augment 400. In the illustrative embodiment described herein, the connectors 450, 460 define a dovetail joint. In such a way, the connectors 460 are embodied as a pair of dovetail-type tabs 462 that are received into a corresponding pair of dovetail-type slots 452 that embody the connectors 450 of the central lobe component 402. The tabs 462 and the slots 452 taper downwardly from their superior ends to their inferior ends. As such, a taper lock is created as the tabs 462 are advanced into the slots 452 thereby locking the components 404, 406 to the central lobe component 402. The radial distance between each of the pair of tabs 462 on the medial lobe component 404 is the same as the radial distance between each of the pair of tabs 462 on the lateral lobe component 406. As such, the side lobe components 404, 406 may, in practice, be installed on either side of the central lobe component 402. This enhances the flexibility of the modular tibial cone augment 400 since its side lobe components are interchangeable with one another and thus any of its side lobe components may be secured to either side of its central lobe component 402.

Like the body 16 of the tibial cone component 12 and the body 116 of the femoral cone augment 112 discussed above, the bodies 416, 430 of the lobe components 402, 404, 406 of the modular tibial cone augment 400 are illustratively embodied as a solid-metal base 472 having a porous-metal coating 470 disposed thereon. The solid-metal base 472 and the porous-metal coating 470 may be embodied and manufactured in a similar manner as the solid-metal base 32 and the porous metal coating 30 discussed above in regard to the tibial cone component 12, with all such features, methods, starting materials, and alternatives not being repeated herein for purposes of brevity. In the illustrative embodiment described herein, like as was described above in regard to the tibial cone augment 12, the porous-metal coating 470 is disposed on the solid-metal base 472 of the lobe components 402, 404, 406 by virtue of being additively manufactured contemporaneously with the solid-metal base 472 so as to create a common, monolithic component of the two metal structures.

As can be seen in FIGS. 37, 40, and 41, the inner sidewall 476 that defines the bore 418 of the hollow body 416 has a number of cement pockets 478 formed therein. Bone cement is received into the cement pockets 478 to increase adhesion of the cement to the modular tibial cone augment 400 during implantation of the tibial revision prosthesis.

In use, the modular tibial cone augment 400 may be used by a surgeon during a surgical procedure to implant a tibial revision prosthesis. During such a procedure, the surgeon will assess the patient's bone. Specifically, the surgeon will determine the condition of bone tissue of the proximal end of the patient's tibia. From there, the surgeon can determine the size and type of cone augment that is needed—e.g., a concentric, bi-lobe, or tri-lobe cone augment. The surgeon then forms a surgically-prepared cavity in the proximal end of the tibia of the patient that corresponds to the size and type of tibial cone augment to be implanted.

The surgeon may then assemble a modular tibial cone augment 400 that corresponds to the shape of the surgically-prepared cavity by locking a selected medial lobe component 404 or a selected lateral lobe component 406—or both—to a selected central lobe component 402 so as to assemble a desired size and configuration of the tibial cone augment to be implanted. As discussed above, to fit the needs of a given surgical application, the modular tibial cone augment 400 may be assembled as a tri-lobe tibial augment (i.e., it has all three lobe components 402, 404, 406), a bi-lobe tibial augment (i.e., it has a central lobe component 402 and only one of the medial lobe component 404 or the lateral lobe component 406, but not both) or a concentric tibial augment (i.e., it has a central lobe component 402, but neither the medial lobe component 404 nor the lateral lobe component 406). Moreover, each of the components 402, 404, 406 may be provided in a range of shapes and sizes to increase the surgeon's options.

Once the desired arrangement of the modular tibial cone augment 400 has been assembled, the surgeon may then install the assembled construct in the surgically-prepared cavity formed in the proximal end of the tibia.

As can be seen in FIGS. 42-45, the femoral cone augment 112 has a pair of impact lugs 122, 124 secured to the inner sidewall 136 that defines the bore 118 of the augment's hollow body 116. The impact lugs 122, 124 are secured to opposite sides of the inner sidewall 136. Specifically, in the illustrative embodiment described herein, the medial impact lug 122 is secured to a medial side of the inner sidewall 136 and the lateral impact lug 124 is secured to the lateral side of the inner sidewall 136.

Figure 42:
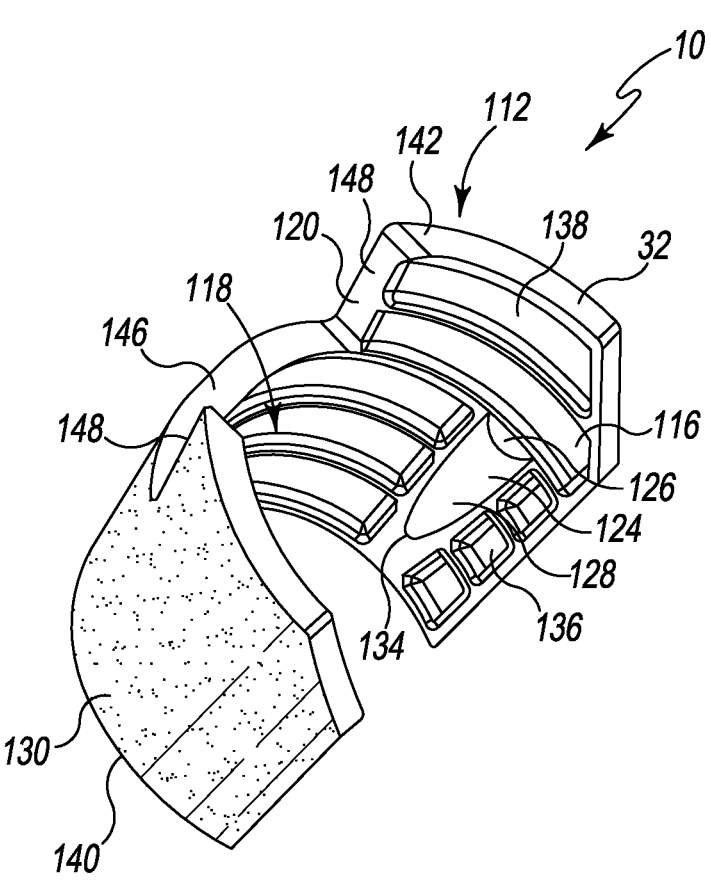
FIG. 42 is another perspective view of the femoral cone augment of FIG. 12.
Figure 43:
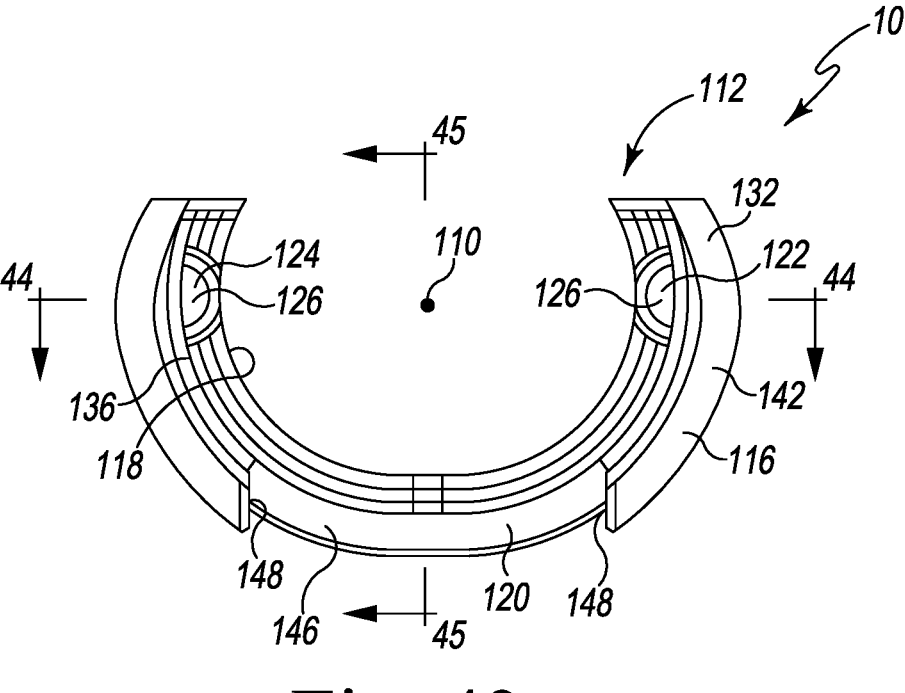
FIG. 43 is an inferior view of the femoral cone augment of FIG. 12.
Figure 44:
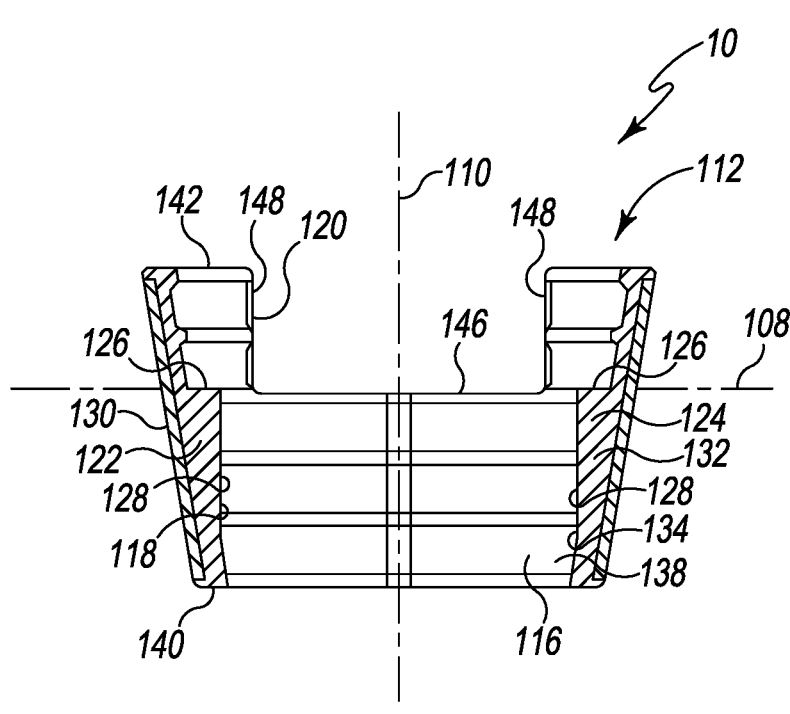
FIG. 44 is a cross sectional view of the femoral cone augment taken along the line 44-44 of FIG. 43, as viewed in the direction of the arrows.

As can be seen in FIGS. 43 and 44, the impact lugs 122, 124 extend inwardly from the inner sidewall 136 toward a central axis 110 of the augment's bore 118. Moreover, each of the impact lugs 122, 124 has a flat, inferior-most impact surface 126. As will be discussed below in more detail, the impact surfaces 126 of the impact lugs 122, 124 are used during installation of the femoral cone augment 112 into the patient's knee. As can be seen best in FIGS. 42 and 45, the impact lugs 122, 124 include a curved outer body 128 that extends superiorly from the lug's impact surface 126. The curved outer body 128 of the impact lugs 122, 124 is tapered along its length in the superior/inferior direction such that its superior end 134 blends into the augment's inner sidewall 136, as shown in FIGS. 42 and 45.

Figure 45:
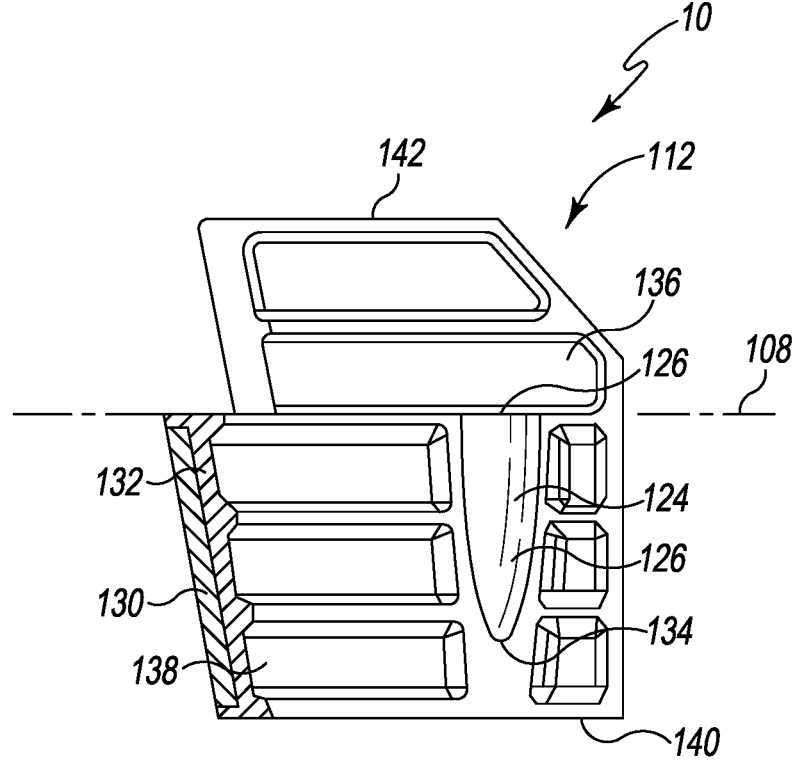
FIG. 45 is a cross sectional view of the femoral cone augment taken along the line 45-45 of FIG. 43, as viewed in the direction of the arrows.

As can be seen best in FIGS. 42, 44, and 45, the impact lugs 122, 124 are positioned within the bore 118 of the femoral cone augment's hollow body 116. In particular, the impact lugs 122, 124 are positioned at location between the superior end 140 and the inferior end 142 of the augment's hollow body 116. In such a way, the impact surfaces 126 of the impact lugs 122, 124 are spaced apart inferiorly from the body's superior end 140 and superiorly from the body's inferior end 142. In the illustrative embodiment described herein, the superior end 134 of each of the impact lugs 122, 124 is spaced apart inferiorly from the superior end 140 of the hollow body 116.

As can be seen best in FIGS. 42-44, the box cutout 120 formed in the posterior side of the femoral cone augment 112 is defined by a flat, inferior-facing surface 146 and a pair of opposed side surfaces 148. As will be discussed below in greater detail, the flat, inferior-facing surface 146 of the box cutout 120 defines an impact surface that, along with the impact surfaces 126 of the impact lugs 122, 124, is contacted by an impactor head to install the femoral cone augment 112.

In the illustrative embodiment described herein, the impact surfaces 126 of the impact lugs 122, 124 are coplanar. In particular, as can be seen in FIG. 44, the impact surfaces 126 of the impact lugs 122, 124 lie on a common plane 108 extending in the medial/lateral direction. As can be seen in FIGS. 44 and 45, in the illustrative embodiment described herein, the inferior-facing impact surface 146 of the box cutout 120 is coplanar with the impact surfaces 126 of the impact lugs 122, 124. As such, the inferior-facing impact surface 146 of the box cutout 120 also lies on the plane 108.

Referring now to FIGS. 46-49, there is shown a knee cone trial component 500, specifically a femoral cone trial component 512. As used herein, the term "knee cone trial component" refers to is an orthopaedic surgical instrument for use by a surgeon in trialing or otherwise assessing the fit of a knee cone augment during performance an orthopaedic surgical procedure. As such, it should be appreciated that, as used herein, the term "knee cone trial component" is distinct from orthopaedic implants or prostheses that are surgically implanted in the body of the patient or other orthopaedic surgical instruments (such as canal reamers, intramedullary rods, etcetera) that are used to perform other functions during an orthopaedic surgical procedure. The term "femoral cone trial component" refers to a knee cone trial component that is sized and shaped to mimic a femoral cone augment such as the femoral cone augment 112.

Because the femoral cone trial component 512 is designed to mimic the femoral cone augment 112, it possesses a similar structure as the augment 112. Specifically, as can be seen in FIGS. 46-49, the femoral cone trial component 512 includes an elongated hollow body 516 that is open on its anterior side. The bore 518 defined by the hollow body 516 is sized and shaped to receive a femoral trial stem component of a femoral revision trial prosthesis (not shown). Moreover, the size and shape of the bore 518 allow the position of the femoral stem trial component of the femoral revision trial prosthesis to be offset in the medial/lateral direction from the center of the femoral cone trial component 512 as needed to fit the needs of a given surgical installation. Moreover, the body 516 has a cutout 520 formed in the posterior side of the femoral cone trial component 512. The cutout 520 provides clearance for the box of the revision femoral trial component.

Like the femoral cone augment 112, the femoral cone trial component 512 has a pair of impact lugs 522, 524 secured to the inner sidewall 536 that defines the bore 518 of the trial component's hollow body 516. The impact lugs 522, 524 are secured to opposite sides of the inner sidewall 536. Specifically, in the illustrative embodiment described herein, the medial impact lug 522 is secured to a medial side of the inner sidewall 536 and the lateral impact lug 524 is secured to the lateral side of the inner sidewall 536.

Figure 46:
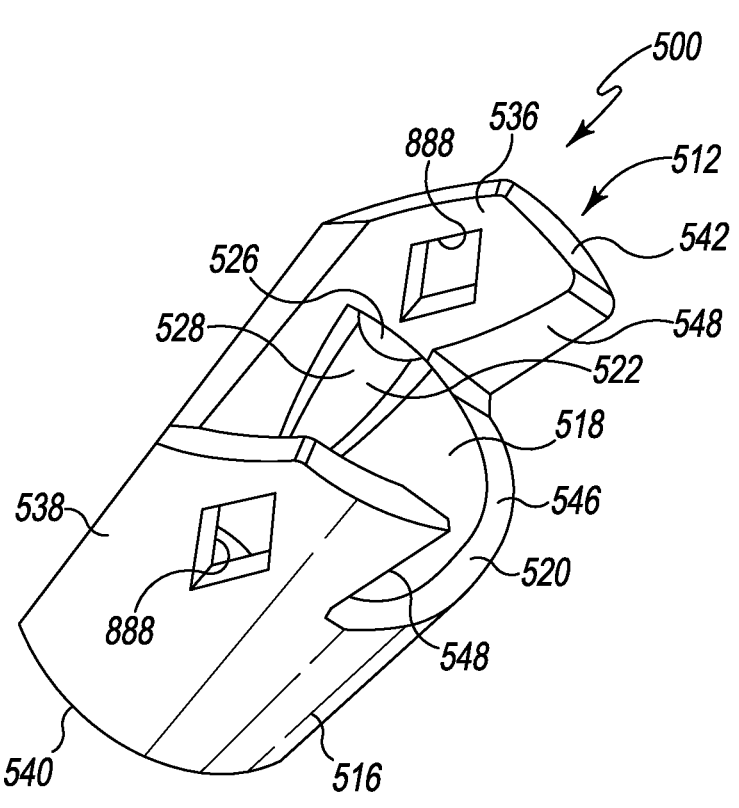
FIG. 46 is a perspective view of a femoral cone trial component.
Figure 47:
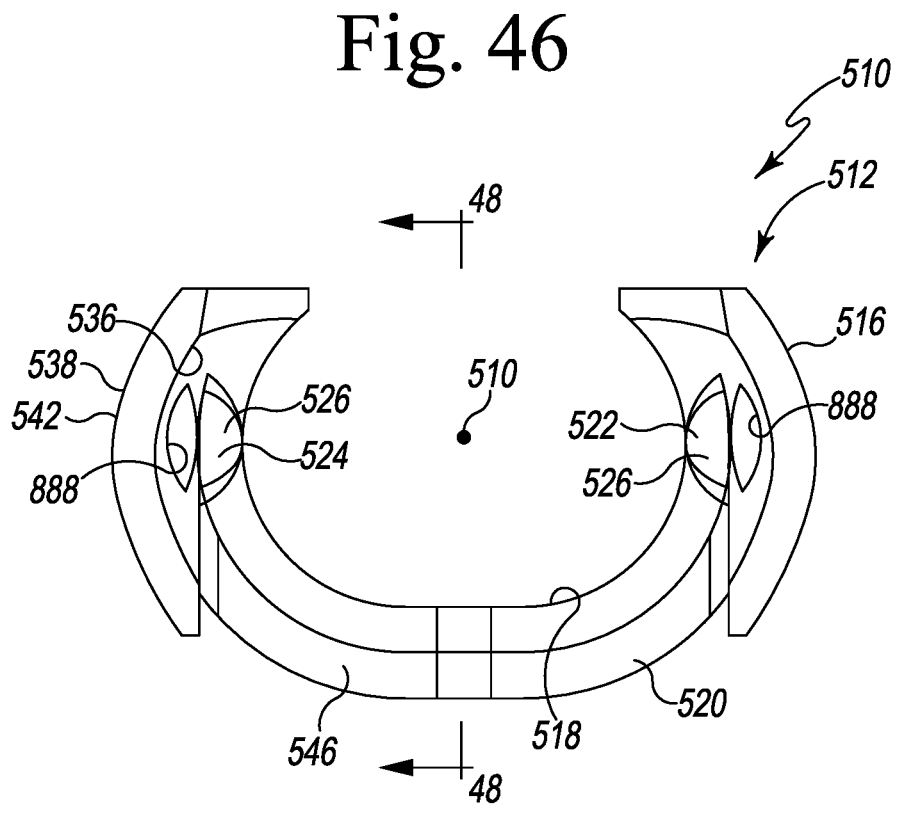
FIG. 47 is an inferior view of the femoral cone trial component of FIG. 46.

As can be seen in FIG. 47, the impact lugs 522, 524 extend inwardly from the inner sidewall 536 toward a central axis 510 of the trial component's bore 518. Moreover, each of the impact lugs 522, 524 has a flat, inferior-most impact surface 526. As will be discussed below in more detail, the impact surfaces 526 of the impact lugs 522, 524 are used during installation of the femoral cone trial component 512 into the patient's knee. As can be seen best in FIGS. 46 and 48, the impact lugs 522, 524 include a curved outer body 528 that extends superiorly from the lug's impact surface 526. The curved outer body 528 of the impact lugs 522, 524 is tapered along its length in the superior/inferior direction such that its superior end 534 blends into the trial component's inner sidewall 536, as shown in FIG. 48.

Figure 48:
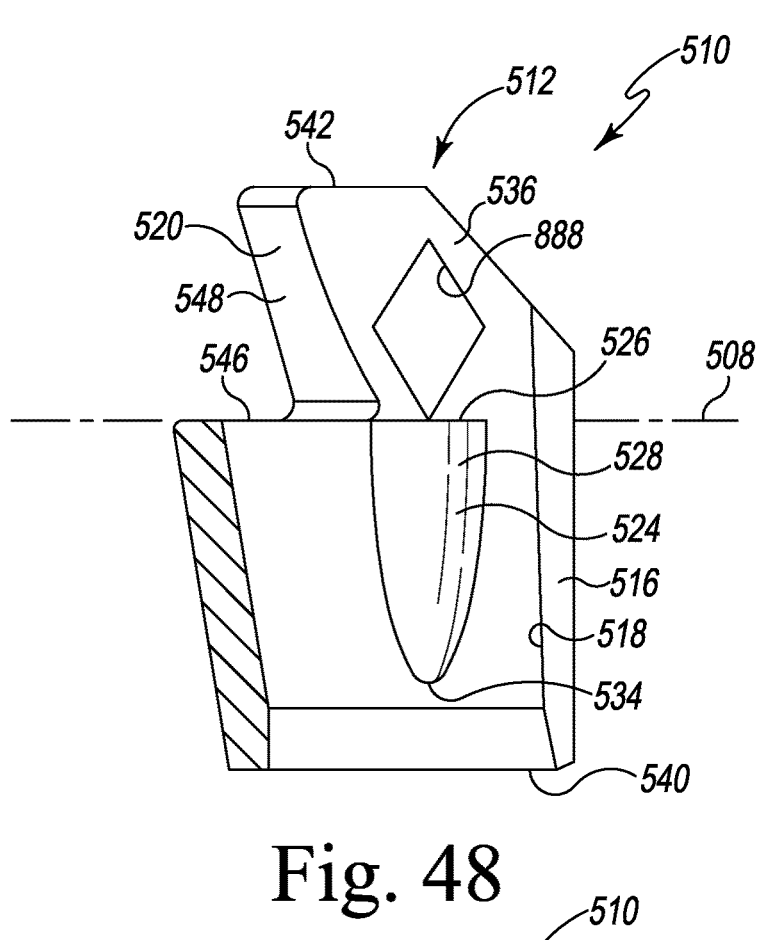
FIG. 48 is a cross sectional view of the femoral cone trial component taken along the line 48-48 of FIG. 47, as viewed in the direction of the arrows.
Figure 49:
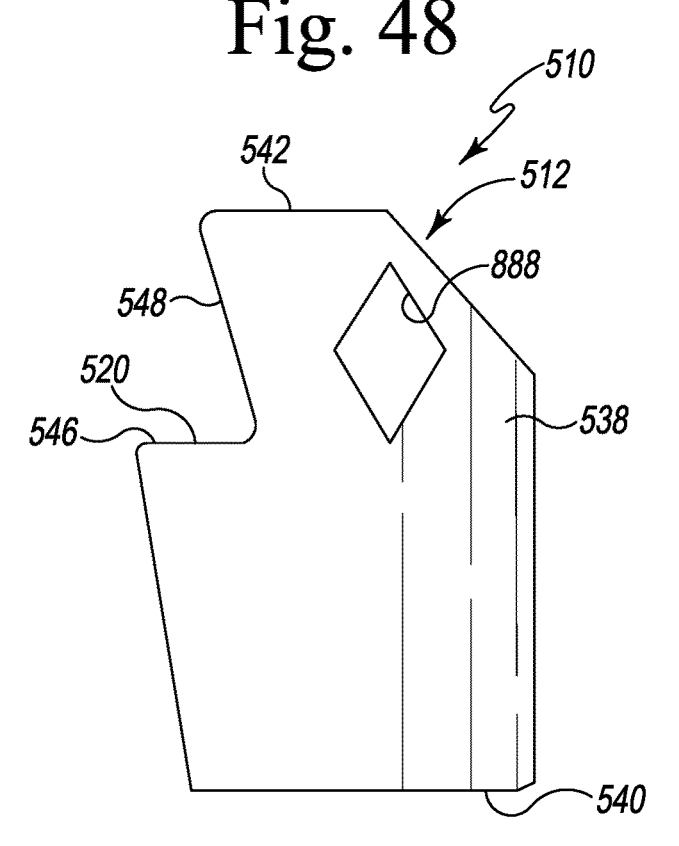
FIG. 49 is a side elevation view of the femoral cone trial component of FIG. 46.

As can be seen best in FIGS. 46-48, the impact lugs 522, 524 are positioned within the bore 518 of the femoral cone trial component's hollow body 516. In particular, the impact lugs 522, 524 are positioned at location between the superior end 540 and the inferior end 542 of the augment's hollow body 516. In such a way, the impact surfaces 526 of the impact lugs 522, 524 are spaced apart inferiorly from the body's superior end 540 and superiorly from the body's inferior end 542. In the illustrative embodiment described herein, the superior end 534 of each of the impact lugs 522, 524 is spaced apart inferiorly from the superior end 540 of the hollow body 516.

As can be seen best in FIGS. 46 and 47, the box cutout 520 formed in the posterior side of the femoral cone trial component 512 is defined by a flat, inferior-facing surface 546 and a pair of opposed side surfaces 548. As will be discussed below in greater detail, the flat, inferior-facing surface 546 of the box cutout 520 defines an impact surface that, along with the impact surfaces 526 of the impact lugs 522, 524, is contacted by an impactor head to install the femoral cone trial component 512.

In the illustrative embodiment described herein, the impact surfaces 526 of the impact lugs 522, 524 are coplanar. In particular, the impact surfaces 526 of the impact lugs 522, 524 lie on a common plane 508 extending in the medial/lateral direction. As can be seen in FIG. 48, in the illustrative embodiment described herein, the inferior-facing impact surface 546 of the box cutout 520 is coplanar with the impact surfaces 526 of the impact lugs 522, 524. As such, the inferior-facing impact surface 546 of the box cutout 520 also lies on the plane 508.

Like the other orthopaedic surgical instruments discussed above, in the illustrative embodiment described herein, the femoral cone trial component 512 is constructed with stainless steel. Other suitable materials may be used to fit the needs of a given design of the femoral cone trial component 512.

Figures 50, 51, 52:
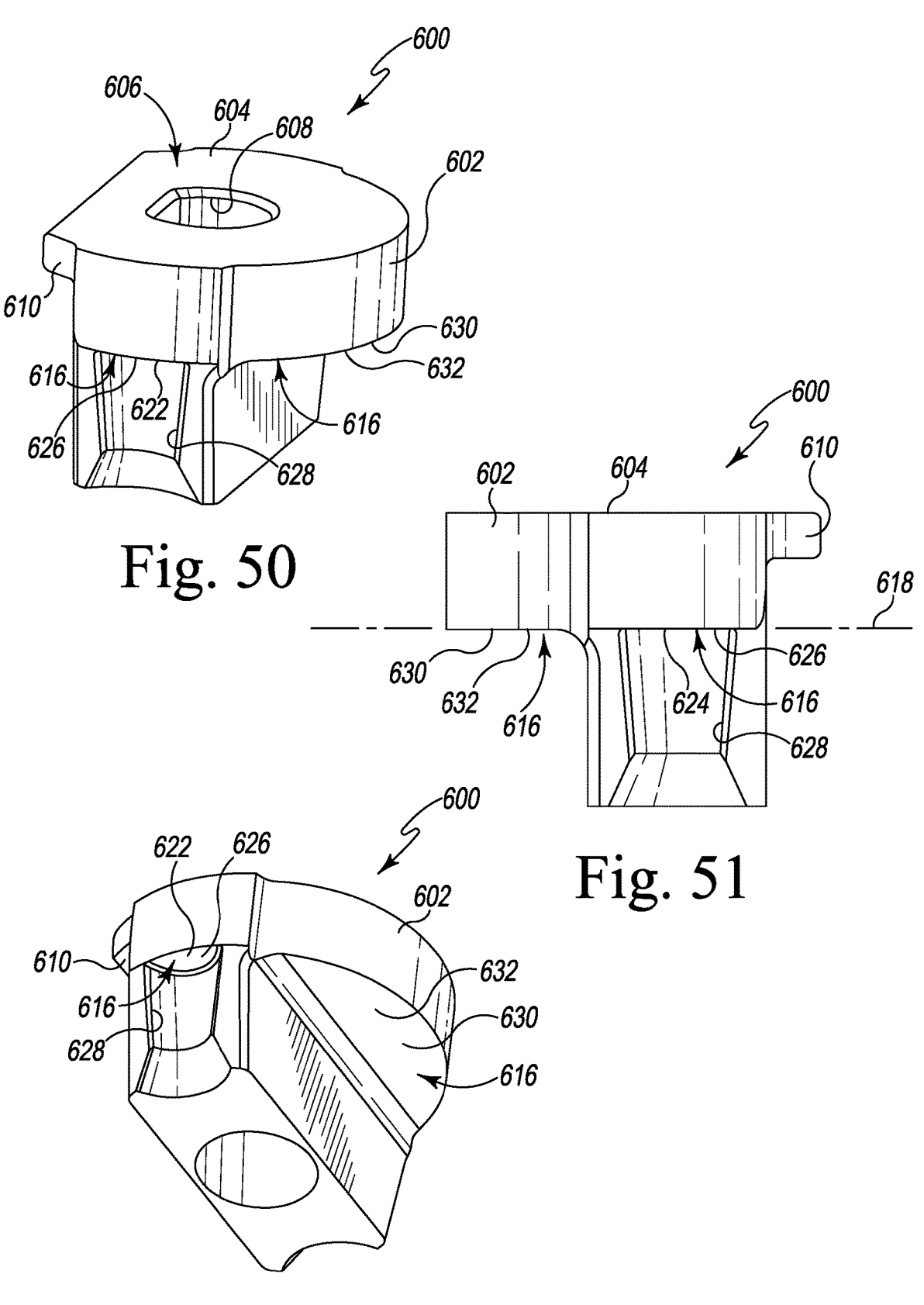
FIG. 50 is a perspective view of an impactor head for use in installing the femoral cone augment of FIGS. 12-14 and 42-49, along with the femoral cone trial component of FIGS. 46-49.
FIG. 51 is a side elevation view of the impactor head of FIG. 50.
FIG. 52 is a perspective view showing the distal end of the impactor head of FIG. 50.
Figure 83:
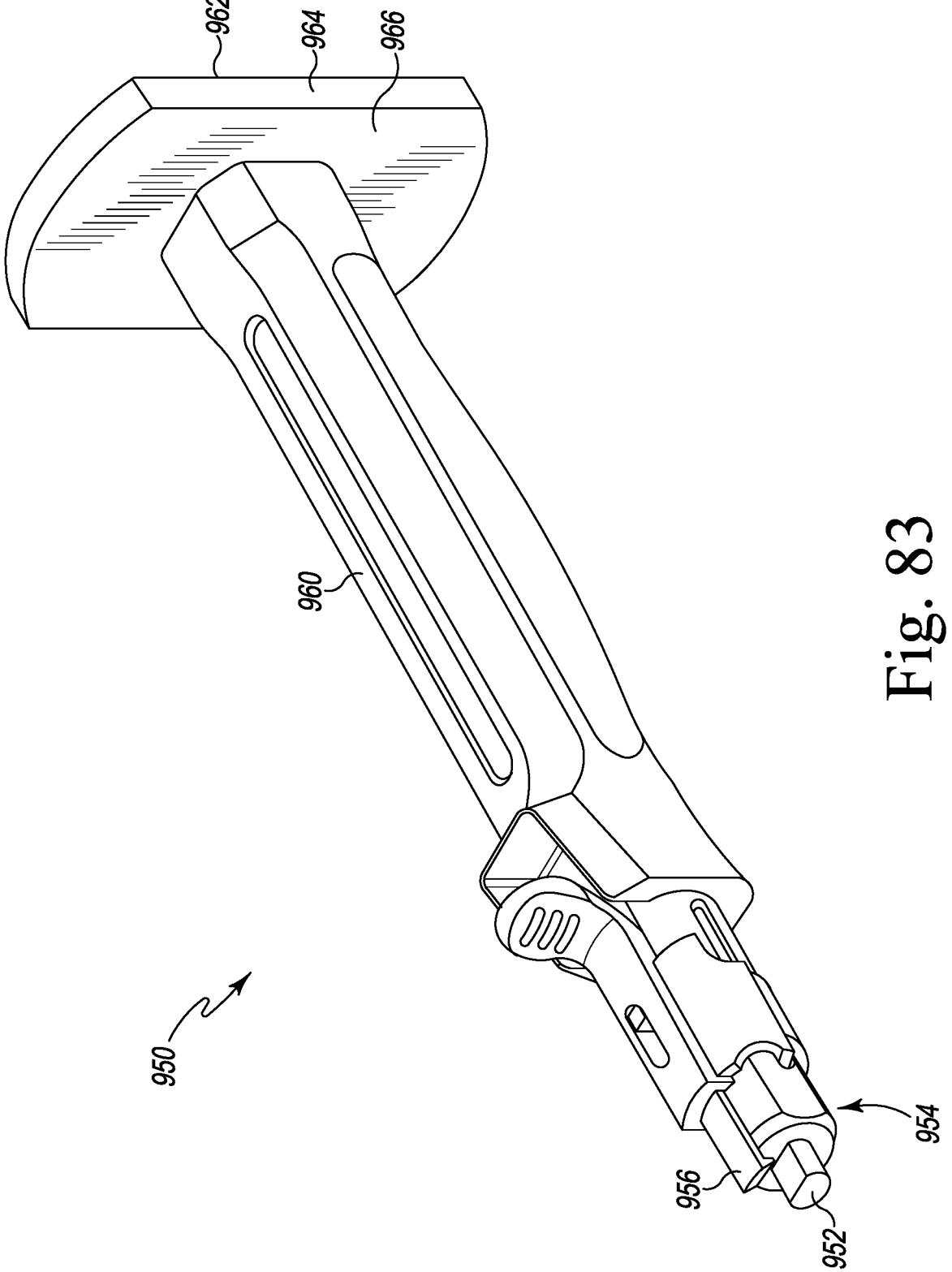
FIG. 83 is a perspective view of an impaction handle.

Referring now to FIGS. 50-52, there is shown an impactor head 600 that is configured to impact the femoral cone augment 112 and the femoral cone trial component 512 during installation of the augment 112 and the trial component 512 into the patient's knee. A proximal surface 604 of the body 602 of the impactor head 600 is configured to be secured to an impaction handle. In the illustrative embodiment described herein, the proximal surface 604 includes a connector 606 for connecting the impactor head 600 to a removable impaction handle 950 (see FIG. 83). It should be appreciated; however, that in other embodiments the proximal surface 604 may also be secured to an integrated, non-removable impaction handle. The connector 606 includes a D-shaped socket 608 formed in the proximal surface 604 of the impactor head 600. The D-shaped socket 608 is sized, shaped, and positioned to receive a D-shaped connecting pin 952 of the connector 954 of the impaction handle 950 (see FIG. 83). The connector 606 of the impactor head 600 also includes a connector lip 610. When the impaction handle's connecting pin 952 is inserted in the D-shaped socket 608 of the impactor head 600 and thereafter advanced downwardly, the connector lip 610 is engaged by a locking pawl 956 of the impaction handle's connector 954 (see FIG. 53) to secure the impactor head 600 to the impaction handle 950.

Figures 57, 58, 59:
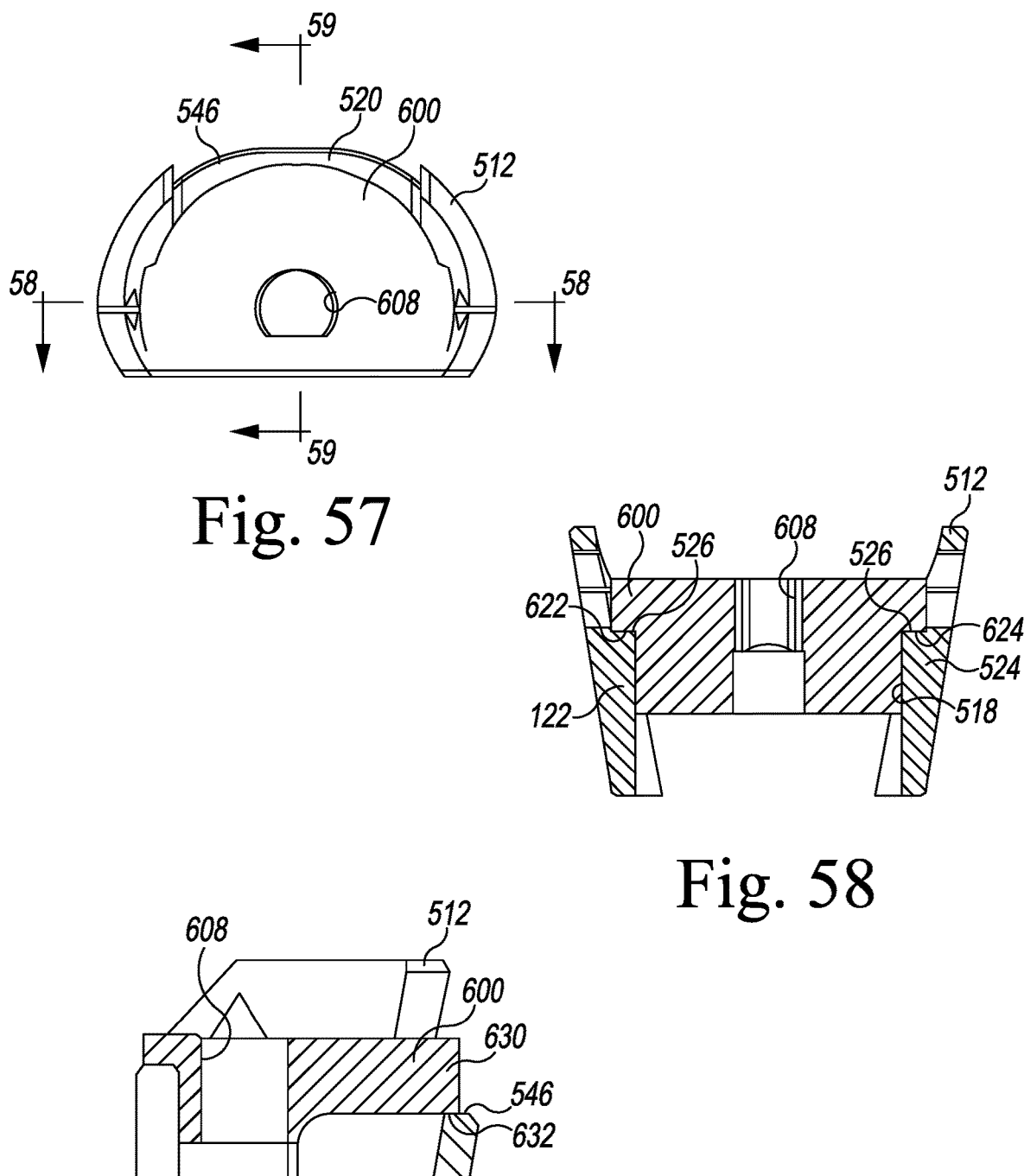
FIG. 57 illustrates the impactor head of FIG. 50 positioned in contact with the femoral cone trial component of FIGS. 46-49.
FIG. 58 is a cross sectional view taken along the line 58-58 of FIG. 57, as viewed in the direction of the arrows.
FIG. 59 is a cross sectional view taken along the line 59-59 of FIG. 57, as viewed in the direction of the arrows.

Opposite the proximal surface 604, the body 602 of the impactor head 600 includes an impact surface 616. The impact surface 616 has a pair of impact shoulders 622, 624 formed therein. The impact shoulders 622, 624 are formed in opposite sides of the body 602 of the impactor head 600. Specifically, in the illustrative embodiment described herein, the medial impact shoulder 622 is formed in a medial side of the body 602 of the impactor head 600 and the lateral impact shoulder 624 is formed in the lateral side of the body 602 of the impactor head 600. Each of the impact shoulders 622, 624 has a flat impact surface 626 that defines the blind proximal end of a guide slot 628. As shown in FIGS. 54-56, the impact surfaces 626 are sized and shaped to be positioned on the impact surfaces 126 of the impact lugs 122, 124 when the impactor head 600 is used during installation of the femoral cone augment 112 into the patient's knee. Similarly, as shown in FIGS. 57-59, the impact surfaces 626 are also sized and shaped to be positioned on the impact surfaces 526 of the impact lugs 522, 524 when the impactor head 600 is used during installation of the femoral cone trial component 512 into the patient's knee.

The impact surface 616 also has an impact lip 630 formed therein. The impact lip 630 has a flat impact surface 632 facing the same direction as the impact surfaces 626 of the impactor head's impact shoulders 622, 624. As shown in FIGS. 54-56, the impact surface 632 of the impact lip 630 is sized and shaped to be positioned on the flat, inferior-facing surface 146 of the box cutout 120 of the femoral cone augment 112 when the impactor head 600 is used during installation of the femoral cone augment 112 into the patient's knee. Similarly, as shown in FIGS. 57-59, the impact surface 632 of the impact lip 630 is also sized and shaped to be positioned on the flat, inferior-facing surface 546 of the box cutout 520 of the femoral cone trial component 512 when the impactor head 600 is used during installation of the femoral cone trial component 512 into the patient's knee.

In the illustrative embodiment described herein, the impact surfaces 626 of the impact shoulders 622, 624 are coplanar. In particular, the impact surfaces 626 of the impact shoulders 622, 624 lie on a common plane 618 extending in the medial/lateral direction. As can be seen in FIG. 51, in the illustrative embodiment described herein, the flat impact surface 632 of the impact lip 630 is coplanar with the impact surfaces 626 of the impact shoulders 622, 624. As such, the impact surface 632 of the impact lip 630 also lies on the plane 618.

Like the surgical broaches 14, 114, in the illustrative embodiment described herein, the impactor head 600 is constructed with stainless steel. Other suitable materials may be used to fit the needs of a given design of the impactor head 600.

Moreover, the impactor head 600 may be provided in a number of different configurations to correspond to the different configurations of the femoral cone augment 112 and the femoral cone trial component 512. In particular, the impactor head 600 may be configured in various different sizes to conform to the sizes of the femoral cone augment 112 and the femoral cone trial component 512. As such, in one illustrative embodiment, the impactor head 600 may be provided in four different sizes (e.g., Sizes Small (S), Medium (M), Large (L), Extra Large (XL)), although additional sizes of the impactor head 600 (e.g., Size Double Extra Large (XXL)) could also be provided if the femoral cone augment 112 and the femoral cone trial component 512 are provided in such additional sizes.

Figure 53:
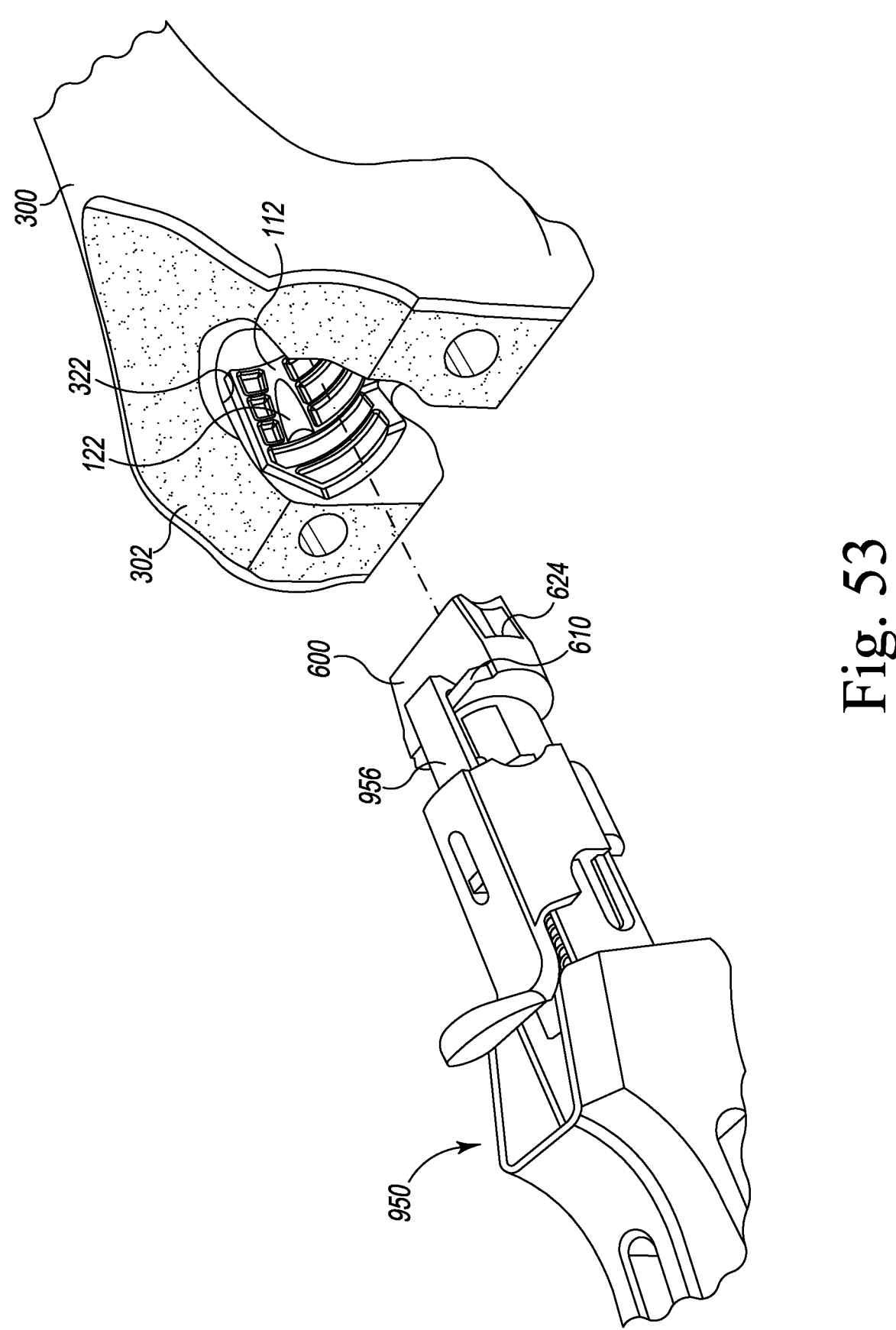

As can be seen in FIG. 53, the impactor head 600 may be used during installation of the femoral cone augment 112 in a revision procedure in which a primary femoral implant has been removed from the distal end 302 of the patient's femur 300. The impactor head 600 may also be used to install the femoral cone trial component 512 during such a revision procedure. Prior to installation of either femoral cone augment 112 or the femoral cone trial component 512, the cavity 322 to receive the femoral cone augment 112 (or trial component 512) is first surgically-prepared in the distal end 302 of the patient's femur 300. The method described above in regard to FIGS. 32-36 may be used as a procedure for surgically-preparing the distal end 302 of the patient's femur 300 in such a manner. However, it should be appreciated that such a surgical procedure may include additional, fewer, or alternate steps depending on the state of the patient's bony anatomy and the preferences of the surgeon.

Once the surgically-prepared cavity 322 has been formed in the distal end 302 of the patient's femur 300, the surgeon positions a femoral cone augment 112 of the appropriate size in the cavity 322. Thereafter, the surgeon utilizes the impactor head 600 to impact the femoral cone augment 112. To do so, the surgeon first connects an impactor head 600 corresponding in size to femoral cone augment 112 being installed to the impaction handle 950. Specifically, the impaction handle's connecting pin 952 (see FIG. 83) is inserted in the D-shaped socket 608 of the impactor head 600 and thereafter advanced downwardly such that the connector lip 610 of the impactor head 600 is then engaged by the locking pawl 956 of the impaction handle's connector 954 to secure the impactor head 600 to the impaction handle 950.

The surgeon then utilizes the impaction handle 950 to advance the distal end of the impactor head 600 into the bore 118 of the femoral cone augment 112 positioned in the distal end 302 of the patient's femur 300. As the impactor head 600 is advanced into the femoral cone augment's bore 118, the augment's impact lugs 122, 124 are captured in the impactor head's guide slots 628. Specifically, the medial impact lug 122 is captured in the guide slot 628 on the medial side of the impactor head 600 and the lateral impact lug 124 is captured in the guide slot 628 on the lateral side of the impactor head 600. The surgeon advances the impactor head 600 to a seated position in which the impact surfaces 626 of the impact shoulders 622, 624 are positioned in contact with the impact surfaces 126 of the augment's impact lugs 122, 124, respectively, as shown in FIG. 55. Doing so also positions the impact surface 632 of the impact lip 630 into contact with the flat, inferior-facing surface 146 of the box cutout 120 of the femoral cone augment 112 being installed, as shown in FIG. 56.

The surgeon then holds the impaction handle 950 via the grip 960 defined in its elongated body (see FIG. 83) and strikes the upper surface 962 of handle's metal strike plate 964 (see FIG. 83) with a surgical mallet, sledge, or other impaction tool. In doing so, impaction forces are transferred from the impact surfaces 626 of the impact shoulders 622, 624 to the impact surfaces 126 of the augment's impact lugs 122, 124, respectively, and also from the impact surface 632 of the impact lip 630 to the flat, inferior-facing surface 146 of the augment's box cutout 120 thereby driving the femoral cone augment 112 into the bone tissue of the surgically-prepared cavity 322 formed in the distal end 302 of the patient's femur 300.

Once the surgeon has implanted the femoral cone augment 112, the surgeon may then implant a revision femoral prosthesis by installing its stem component through the femoral cone augment and thereafter cementing it in place within the bone.

It should be appreciated that during such a procedure to implant the femoral cone augment 112, the surgeon may elect to use one or more of the femoral cone trial components 512 as part of an intraoperative trialing procedure. As shown in FIGS. 57-59, the impactor head 600 may also be used to install the femoral cone trial component 512. Specifically, in a similar manner to as described above in regard to implantation of the femoral cone augment 112, the surgeon may utilize the impaction handle 950 to advance the distal end of the impactor head 600 into the bore 518 of the femoral cone trial component 512 once the trial component has been positioned in surgically-prepared cavity 322 formed into the distal end 302 of the patient's femur 300. As the impactor head 600 is advanced into the trial component's bore 518, the trial component's impact lugs 522, 524 are captured in the impactor head's guide slots 628. Specifically, the medial impact lug 522 is captured in the guide slot 628 on the medial side of the impactor head 600 and the lateral impact lug 524 is captured in the guide slot 628 on the lateral side of the impactor head 600. The surgeon advances the impactor head 600 to a seated position in which the impact surfaces 626 of the impact shoulders 622, 624 are positioned in contact with the impact surfaces 526 of the trial component's impact lugs 522, 524, respectively, as shown in FIG. 58. Doing so also positions the impact surface 632 of the impact lip 630 into contact with the flat, inferior-facing surface 546 of the box cutout 520 of the femoral cone trial component 512 being installed, as shown in FIG. 59.

The surgeon then holds the impaction handle 950 via the grip 960 defined in its elongated body (see FIG. 83) and strikes the upper surface 962 of handle's metal strike plate 964 (see FIG. 83) with a surgical mallet, sledge, or other impaction tool. In doing so, impaction forces are transferred from the impact surfaces 626 of the impact shoulders 622, 624 to the impact surfaces 526 of the trial component's impact lugs 522, 524, respectively, and also from the impact surface 632 of the impact lip 630 to the flat, inferior-facing surface 546 of the trial component's box cutout 520 thereby driving the femoral cone trial component 512 into the bone tissue of the surgically-prepared cavity 322 formed in the distal end 302 of the patient's femur 300.

Once the femoral cone trial component 512 has been installed in such a manner, the surgeon may use it along with other trial components in the performance of an intraoperative trialing procedure. Once the surgeon is satisfied with the outcome of the trialing procedure, the femoral cone trial component 512 is removed from the patient's femur 300 (in a manner discussed below) and the femoral cone augment 112 is implanted in the manner described above.

It should also be appreciated that other types of augments and trial components may also be embodied with impaction lugs and used in combination with an impactor head having corresponding impaction shoulders. In particular, although the concepts of FIGS. 42-59 have herein been described in the context of a femoral cone augment 112 (and associated trial component 512), the concepts of FIGS. 42-49 could also be incorporated into a bi-lobe or tri-lobe tibial cone augment (and associated trial components) or a concentric cone augment (and associated trial component) for use on either the tibia or the femur of the patient's knee.

Figures 60, 61, 62:
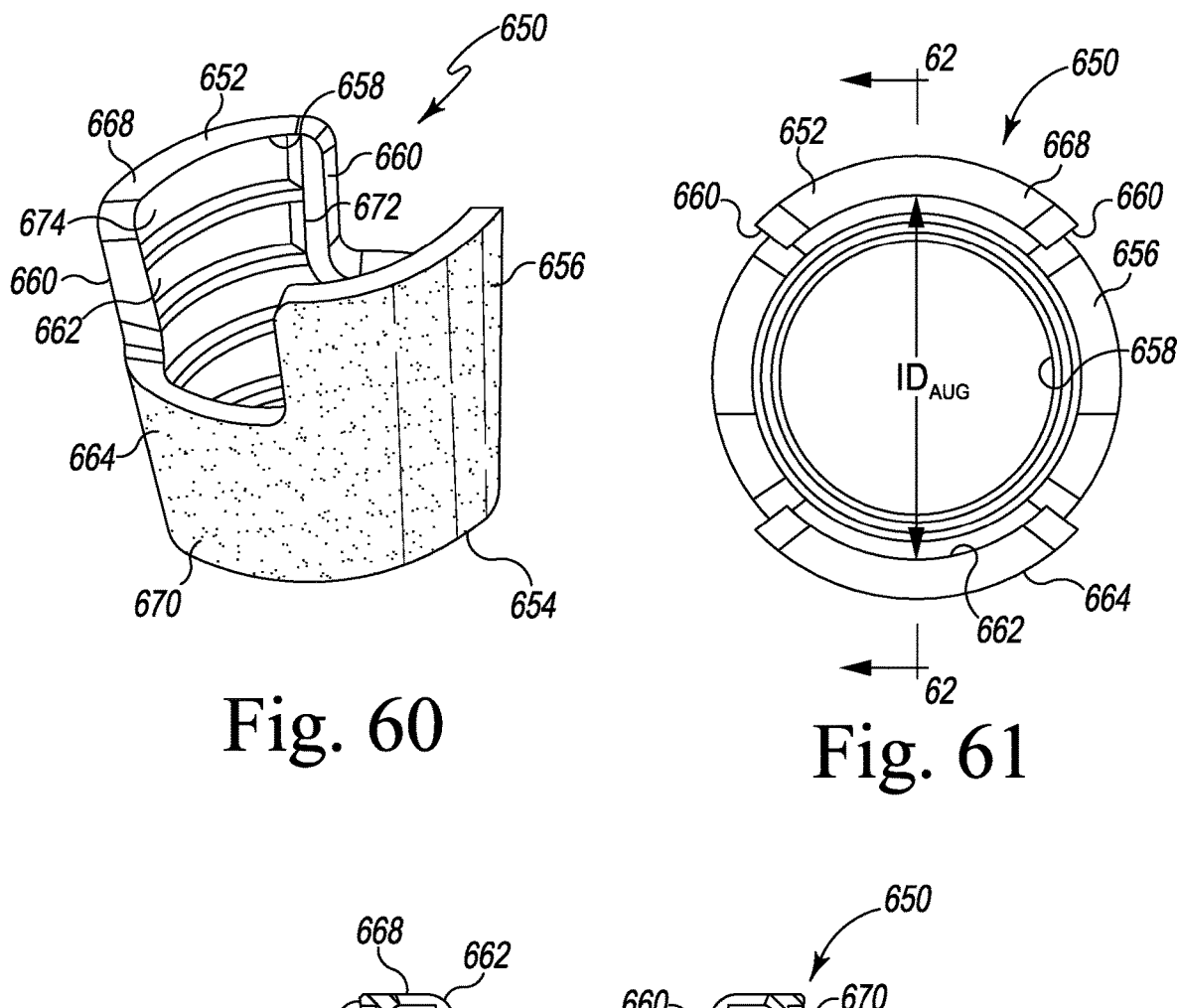
FIG. 60 is a perspective view of a concentric cone augment.
FIG. 61 is an elevation view of the proximal end of the concentric cone augment of FIG. 60.
FIG. 62 is a cross sectional view of the concentric cone augment taken along the line 62-62 of FIG. 61, as viewed in the direction of the arrows.

Referring now to FIGS. 60-62, the orthopaedic joint replacement system 10 also includes a concentric cone augment 650 configured for implantation into either the surgically-prepared cavity 222 in the proximal end 202 of the patient's tibia 200 or the surgically-prepared cavity 322 formed in the distal end 302 of the patient's femur 300. The concentric cone augment 650 includes an elongated conically-shaped hollow body 656 that tapers downwardly from its proximal end 652 to its distal end 654. The bore 658 defined by the hollow body 656 is sized and shaped to receive a tibial stem component of a tibial revision prosthesis (not shown) when the concentric cone augment is implanted in the proximal end 202 of the patient's tibia 200 or a femoral stem component of a femoral revision prosthesis (not shown) when the concentric cone augment is implanted in the distal end 302 of the patient's femur 300. Moreover, the body 656 has a pair of cutouts 660 formed in the proximal end 652 of the concentric cone augment 650. The cutouts 660 provide clearance for the keels of a revision tibial tray or the box of a revision femoral component.

As can be seen in FIGS. 60 and 61, the proximal end 652 of the concentric cone augment's hollow body 656 defines an annular rim 668 that extends radially between the body's inner sidewall 662 and its outer sidewall 664. Given the presence of the cutouts 660, the annular rim 668 has an interrupted surface.

Like the bodies of the tibial cone component 12 and the femoral cone augment 112, the body 656 of the concentric cone augment 650 is illustratively embodied as a solid-metal base 672 having a porous-metal coating 670 disposed thereon. The solid-metal base 672 and the porous-metal coating 670 may be embodied and manufactured in a similar manner as to the solid-metal base 32 and the porous metal coating 30 discussed above in regard to the tibial cone component 12, with all such features, methods, starting materials, and alternatives not being repeated herein for purposes of brevity. In the illustrative embodiment described herein, like as was described above in regard to the tibial cone augment 12, the porous-metal coating 670 is disposed on the solid-metal base 672 of the concentric cone augment 650 by virtue of being additively manufactured contemporaneously with the solid-metal base 672 so as to create a common, monolithic component of the two metal structures.

As can be seen in FIGS. 60 and 62, the inner sidewall 662 that defines the bore 658 of the hollow body 656 has a number of cement pockets 674 formed therein. Bone cement is received into the cement pockets 674 to increase adhesion of the cement to the concentric cone augment 650 during implantation of the tibial revision prosthesis or the femoral revision prosthesis.

Like the tibial cone augment 12 and femoral cone augment 112, the concentric cone augment 650 may be provided in a number of different configurations to fit the needs of a given patient's anatomy. In particular, the concentric cone augment 650 may be configured in various different sizes to conform to the patient's anatomy and/or accommodate a wide range of bone loss. In one illustrative embodiment, the concentric cone augment 650 may be provided in four different sizes (e.g., Sizes Small (S), Medium (M), Large (L), Extra Large (XL)), although other sizes (e.g., Size Double Extra Large (XXL)) could also be provided to fit the needs of a given design of the orthopaedic joint replacement system 10. The inner diameter of the annular rim 668 of the hollow body 656 changes as a function of the size of the concentric cone augment 650. Specifically, the inner diameter ($ID_{AUG}$) of the augment's annular rim 668 increases as the size of the concentric cone augment 650 increases. In other words, the annular rim 658 of a Size M concentric cone augment 650 has a larger inner diameter ($ID_{AUG}$) than the annular rim 658 of a Size S concentric cone augment 650, but a smaller inner diameter ($ID_{AUG}$) than the annular rim 658 of a Size L (or Size XL) concentric cone augment 650.

Figures 63, 64, 65:
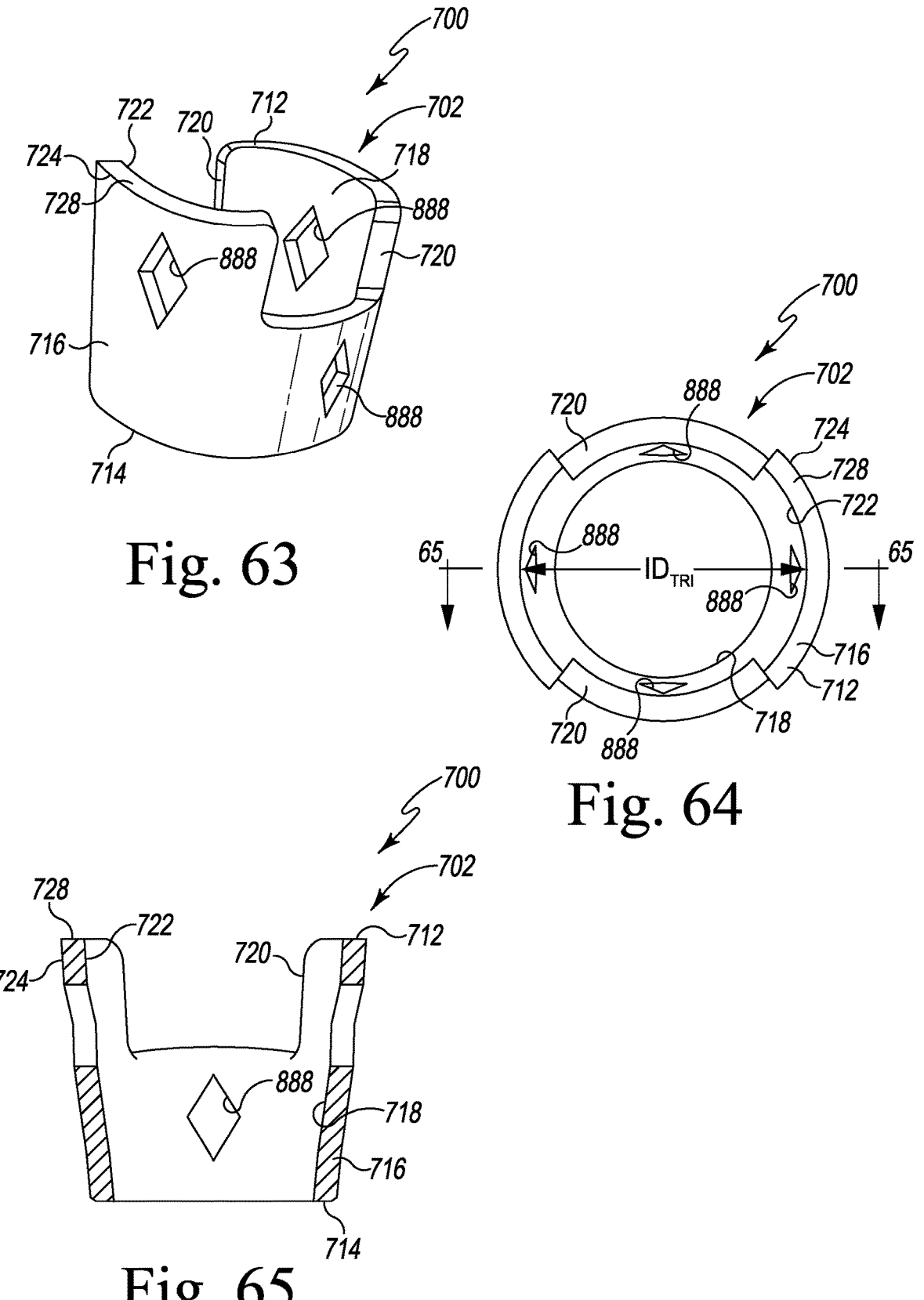
FIG. 63 is a perspective view of a concentric cone trial component.
FIG. 64 is an elevation view of the proximal end of the concentric cone trial component of FIG. 63.
FIG. 65 is a cross sectional view of the concentric cone trial component taken along the line 65-65 of FIG. 64, as viewed in the direction of the arrows.

Referring now to FIGS. 63-65, there is shown another knee cone trial component 700, specifically a concentric cone trial component 702. As used herein, the term "concentric cone trial component" refers to a knee cone trial component that is sized and shaped to mimic a concentric cone augment such as the concentric cone augment 650.

Because the concentric cone trial component 702 is designed to mimic the concentric cone augment 650, it possesses a similar structure as the augment 650. Specifically, as can be seen in FIGS. 63-65, the concentric cone trial component 702 includes an elongated conically-shaped hollow body 716 that tapers downwardly from its proximal end 712 to its distal end 714. The bore 718 defined by the hollow body 716 is sized and shaped to receive a tibial stem trial component of a tibial revision trial prosthesis (not shown) when the concentric cone trial component 702 is installed in the proximal end 202 of the patient's tibia 200 or a femoral stem trial component of a femoral revision trial prosthesis (not shown) when the concentric cone trial component 702 is installed in the distal end 302 of the patient's femur 300. Moreover, the trial component's body 716 has a pair of cutouts 720 formed in the proximal end 712 of the concentric cone trial component 702. The cutouts 720 provide clearance for the keels of a revision tibial tray trial component or the box of a revision femoral trial component.

As can be seen in FIGS. 63 and 64, the proximal end 712 of the trial component's hollow body 716 defines an annular rim 728 that extends radially between the body's inner sidewall 722 and its outer sidewall 724. Given the presence of the cutouts 720, the annular rim 668 has an interrupted surface.

The concentric cone trial component 700 may be provided in a number of different configurations to correspond to the different configurations of the concentric cone augment 650. In particular, the concentric cone trial component 700 may be configured in various different sizes to conform to the range of sizes of the concentric cone augments 650. In one illustrative embodiment, the concentric cone trial component 700 may be provided in four different sizes (e.g., Sizes Small (S), Medium (M), Large (L), Extra Large (XL)), although other sizes (e.g., Size Double Extra Large (XXL)) could also be provided if such additional sizes of the concentric cone augment 650 is also provided. Like the augment it mimics, the inner diameter of the annular rim 728 of the hollow body 716 changes as a function of the size of the concentric cone trial component 700. Specifically, the inner diameter ($IDT_{TRI}$) of the trial component's annular rim 728 increases as the size of the concentric cone trial component 700 increases. In other words, the annular rim 728 of a Size M concentric cone trial component 700 has a larger inner diameter ($ID_{TRI}$) than the annular rim 728 of a Size S concentric cone trial component 700, but a smaller inner diameter ($ID_{TRI}$) than the annular rim 728 of a Size L (or Size XL) concentric cone trial component 700.

Referring now to FIGS. 66-69, there is shown an impactor head 800 that is configured to impact the concentric cone augment 650 and the concentric cone trial component 700 during installation of the augment 650 and the trial component 700 into the patient's knee. Similarly to the impactor head 600 described above, a proximal surface 804 of the body 802 of the impactor head 800 is configured to be secured to a removable impaction handle. In the illustrative embodiment described herein, the proximal surface 804 includes a connector 806 for connecting the impactor head 800 to the impaction handle 950 (see FIG. 83). It should be appreciated; however, that in other embodiments the proximal surface 804 may also be secured to an integrated, non-removable impaction handle. The connector 806 includes a D-shaped socket 808 formed in the proximal surface 804 of the impactor head 800. The D-shaped socket 808 is sized, shaped, and positioned to receive the D-shaped connecting pin 952 of the connector 954 of the impaction handle 950 (see FIG. 83). The connector 806 of the impactor head 800 also includes a connector lip 810. When the impaction handle's connecting pin 952 is inserted in the D-shaped socket 808 of the impactor head 800 and thereafter advanced downwardly, the connector lip 810 is engaged by a locking pawl 956 of the impaction handle's connector 954 (see FIGS. 70 and 71) to secure the impactor head 800 to the impaction handle 950.

Figures 66, 67, 68, 69:
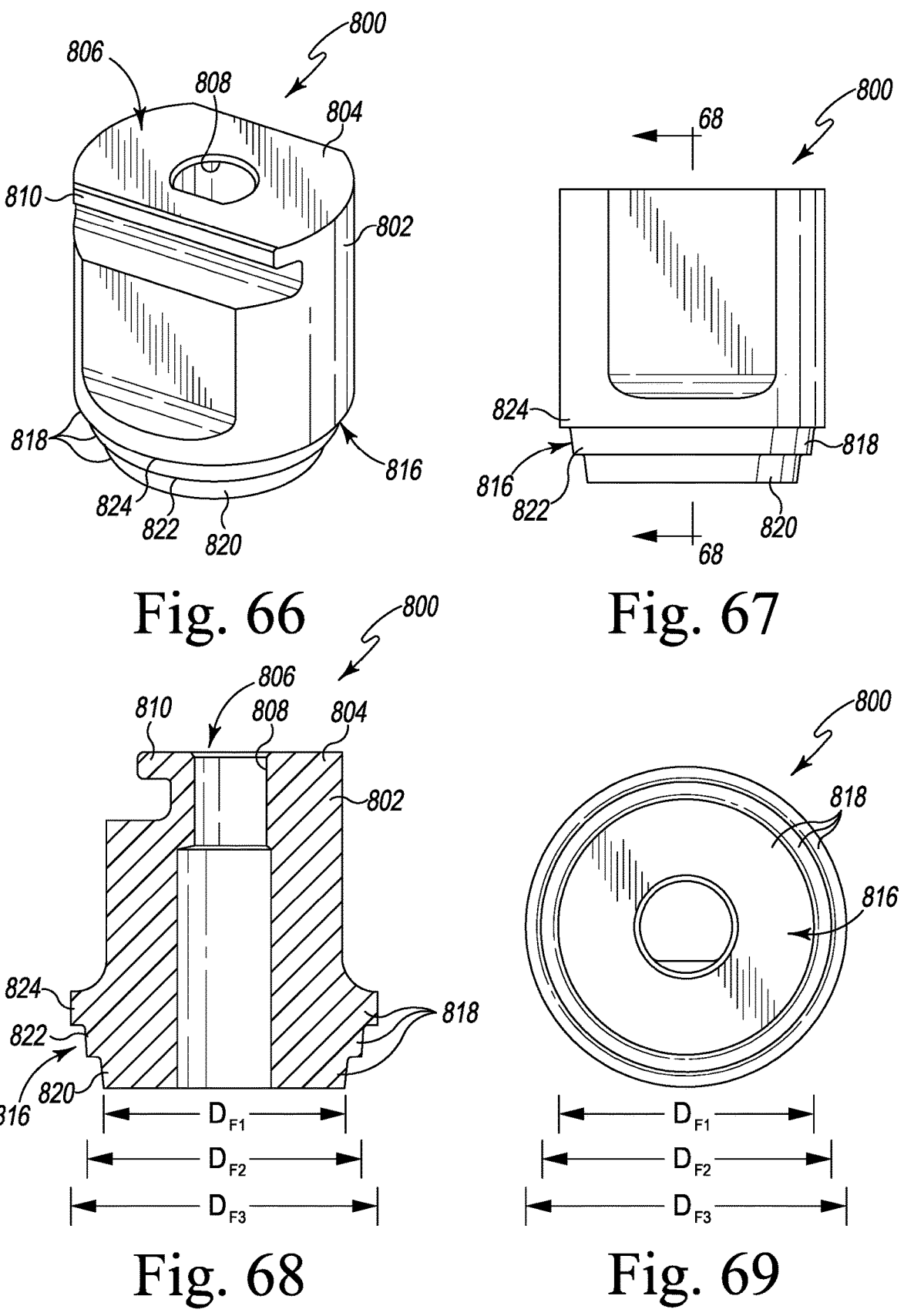
FIG. 66 is a perspective view of an impactor head for installing the concentric cone augment of FIGS. 60-62 and the concentric cone trial component of FIGS. 63-65.
FIG. 67 is an elevation view of the impactor head of FIG. 66.
FIG. 68 is a cross sectional view of the impactor head taken along the line 68-68 of FIG. 67, as viewed in the direction of the arrows.
FIG. 69 is an elevation view of the distal end of the impactor head of FIG. 66.

Opposite the proximal surface 804, the body 802 of the impactor head 800 includes an impact surface 816. The impact surface 816 has a number of annular-shaped concentric flanges 818 formed therein. In the illustrative embodiment described herein, the concentric flanges 818 include a lead-in flange 820 and a pair of impact flanges 822, 824. As can be seen in FIGS. 67-69, the diameter ($D_{F1}$) of the lead-in flange 820 is smaller than the diameter ($D_{F2}$) of the impact flange 822 and the diameter ($D_{F3}$) of the impact flange 824. In addition, the diameter ($D_{F2}$) of the impact flange 822 is smaller than the diameter ($D_{F3}$) of the impact flange 824. Such a terraced surface design allows the impactor head 800 to be used in the installation of differently sized concentric cone augments 650 and concentric cone trial components 700 thereby eliminating the need to have an impactor head for each size of augments and trial components.

Figure 72:
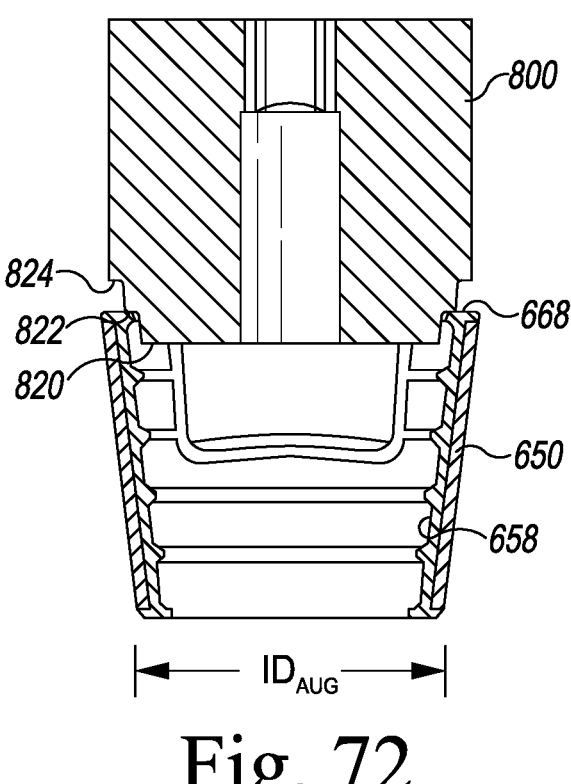
FIGS. 72 and 73 illustrate the impactor head of FIG. 60 positioned in contact with two different sizes of the concentric cone augments of FIGS. 60-62, note the concentric cone augment of FIG. 73 is larger than the concentric cone augment of FIG. 72.
Figure 73:
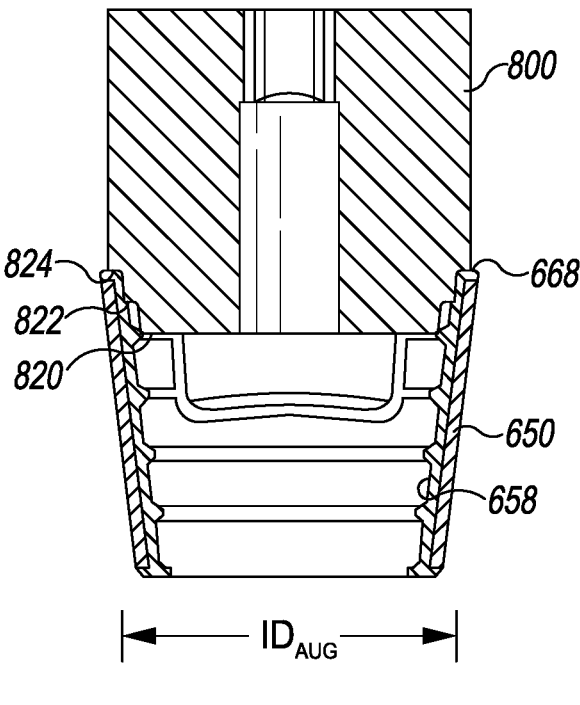

For instance, the impactor head 800 may be used to install both a Size L concentric cone augment 650 (as shown in FIG. 72) and a Size XL concentric cone augment 650 (as shown in FIG. 73). As can be seen in FIG. 72, when used to install the smaller of two sizes of the concentric cone augment 650 (for example a Size L augment versus a Size XL augment), the diameter ($D_{F1}$) of the lead-in flange 820 is smaller than the inner diameter ($ID_{AUG}$) of the augment's annular rim 668 thereby allowing the lead-in flange 820 to be advanced into the augment's bore 658. However, both the diameter ($D_{F2}$) of the impact flange 822 and the diameter ($D_{F3}$) of the impact flange 824 are larger than the inner diameter ($ID_{AUG}$) of the augment's annular rim 668. As such, the impact flange 822 rests on top of the augment's annular rim 668 when the lead-in flange 820 of the impactor head 800 is positioned in the augment's bore 658 thereby allowing impaction forces to transferred from the impact flange 822 to the augment's annular rim 668 during installation of the augment. As can be seen in FIG. 73, when used to install the larger of two sizes of the concentric cone augment 650 (for example a Size XL augment versus a Size L augment), both the diameter ($D_{F1}$) of the lead-in flange 820 and the diameter ($D_{F2}$) of the impact flange 822 are smaller than the inner diameter ($ID_{AUG}$) of the augment's annular rim 668 thereby allowing both the lead-in flange 820 and the impact flange 822 to be advanced into the augment's bore 658. However, the diameter ($D_{F3}$) of the impact flange 824 is larger than the inner diameter ($ID_{AUG}$) of the augment's annular rim 668. As such, the impact flange 824 rests on top of the augment's annular rim 668 when the lead-in flange 820 and the impact flange 822 of the impactor head 800 are positioned in the augment's bore 658 thereby allowing impaction forces to transferred from the impact flange 824 to the augment's annular rim 668 during installation of the augment.

Figure 74:
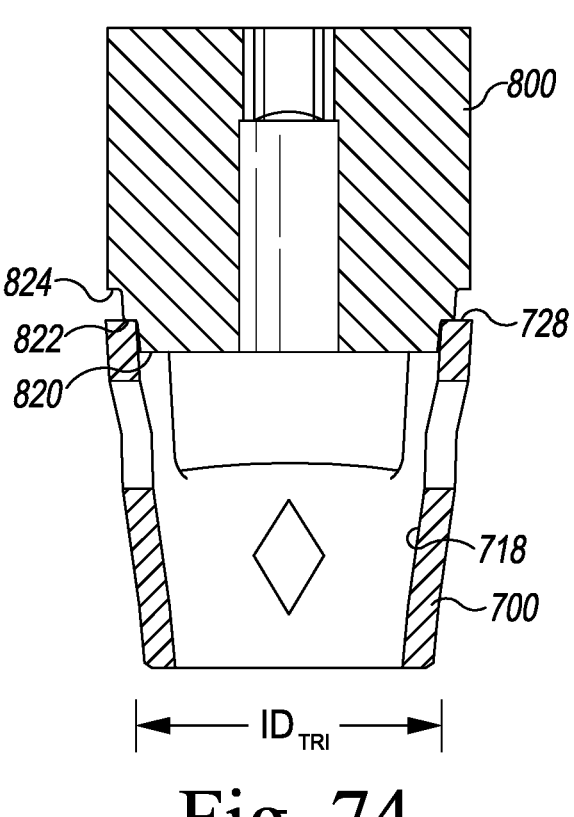
FIGS. 74 and 75 illustrate the impactor head of FIG. 60 positioned in contact with two different sizes of the concentric cone trial components of FIGS. 63-65, note the concentric cone trial component of FIG. 75 is larger than the concentric cone trial component of FIG. 74.
Figure 75:
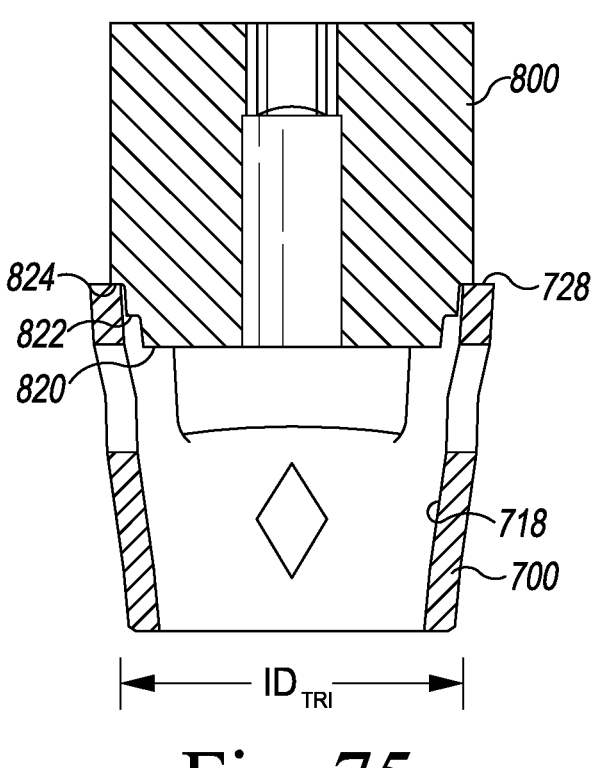

As shown in FIGS. 74 and 75, the impactor head 800 may also be used in the installation of two differently sized concentric cone trial components 700 in a similar manner. In particular, as can be seen in FIG. 74, when used to install the smaller of two sizes of the concentric cone trial component 700 (for example a Size L trial component versus a Size XL trial component), the diameter ($D_{F1}$) of the lead-in flange 820 is smaller than the inner diameter ($ID_{TRI}$) of the trial component's annular rim 728 thereby allowing the lead-in flange 820 to be advanced into the trial component's bore 718. However, both the diameter ($D_{F2}$) of the impact flange 822 and the diameter ($D_{F3}$) of the impact flange 824 are larger than the inner diameter ($ID_{TRI}$) of the trial component's annular rim 728. As such, the impact flange 822 rests on top of the trial component's annular rim 728 when the lead-in flange 820 of the impactor head 800 is positioned in the trial component's bore 718 thereby allowing impaction forces to transferred from the impact flange 822 to the trial component's annular rim 728 during installation of the trial component. As can be seen in FIG. 75, when used to install the larger of two sizes of the concentric cone trial component 700 (for example a Size XL trial component versus a Size L trial component), both the diameter ($D_{F1}$) of the lead-in flange 820 and the diameter ($D_{F2}$) of the impact flange 822 are smaller than the inner diameter ($ID_{TR}$) of the trial component's annular rim 728 thereby allowing both the lead-in flange 820 and the impact flange 822 to be advanced into the trial component's bore 718. However, the diameter ($D_{F3}$) of the impact flange 824 is larger than the inner diameter ($ID_{TRJ}$) of the trial component's annular rim 728. As such, the impact flange 824 rests on top of the trial component's annular rim 728 when the lead-in flange 820 and the impact flange 822 of the impactor head 800 are positioned in the trial component's bore 718 thereby allowing impaction forces to transferred from the impact flange 824 to the trial component's annular rim 728 during installation of the trial component.

It should be appreciated that although the relationship of the impactor head 800 and the concentric cone augment 650 and the concentric cone trial component 700 has been illustratively described in regard to Size L and Size XL augments and trial components, it should be appreciated that the impactor head 800 may be configured for use with other sizes. For example, a single impactor head 800 may be designed for use with Size S and Size M augments and trial components. Moreover, by adding additional impact flanges (beyond the impact flanges 822, 824), the impactor head 800 may be used with more than two sizes of augments and trial components. For example, the impactor head 800 may be configured with three impact flanges thereby allowing it to be used in the installation of three different sizes of the augments and trial components.

Like the other orthopaedic surgical instruments discussed above, in the illustrative embodiment described herein, the impactor head 800 is constructed with stainless steel. Other suitable materials may be used to fit the needs of a given design of the impactor head 800.

Figure 70:
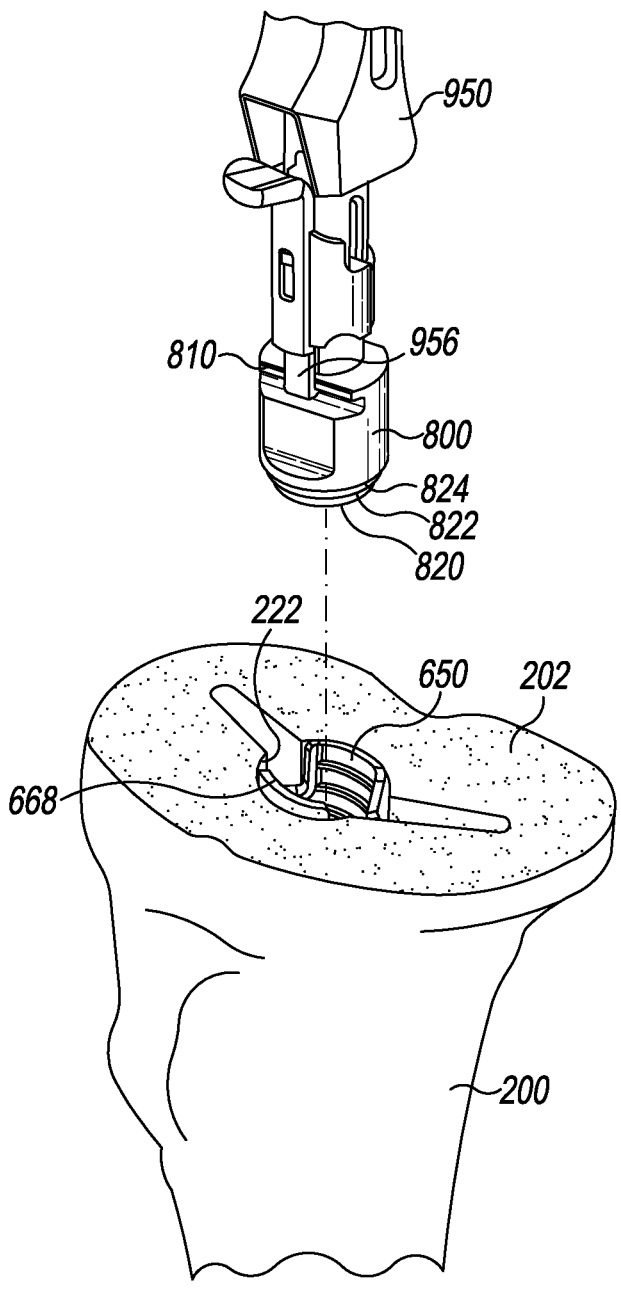
FIG. 70 illustrates the impactor head of FIG. 66 being used in a surgical procedure to implant the concentric cone augment of FIGS. 60-62 into the proximal end of the tibia of a patient.
Figure 71:
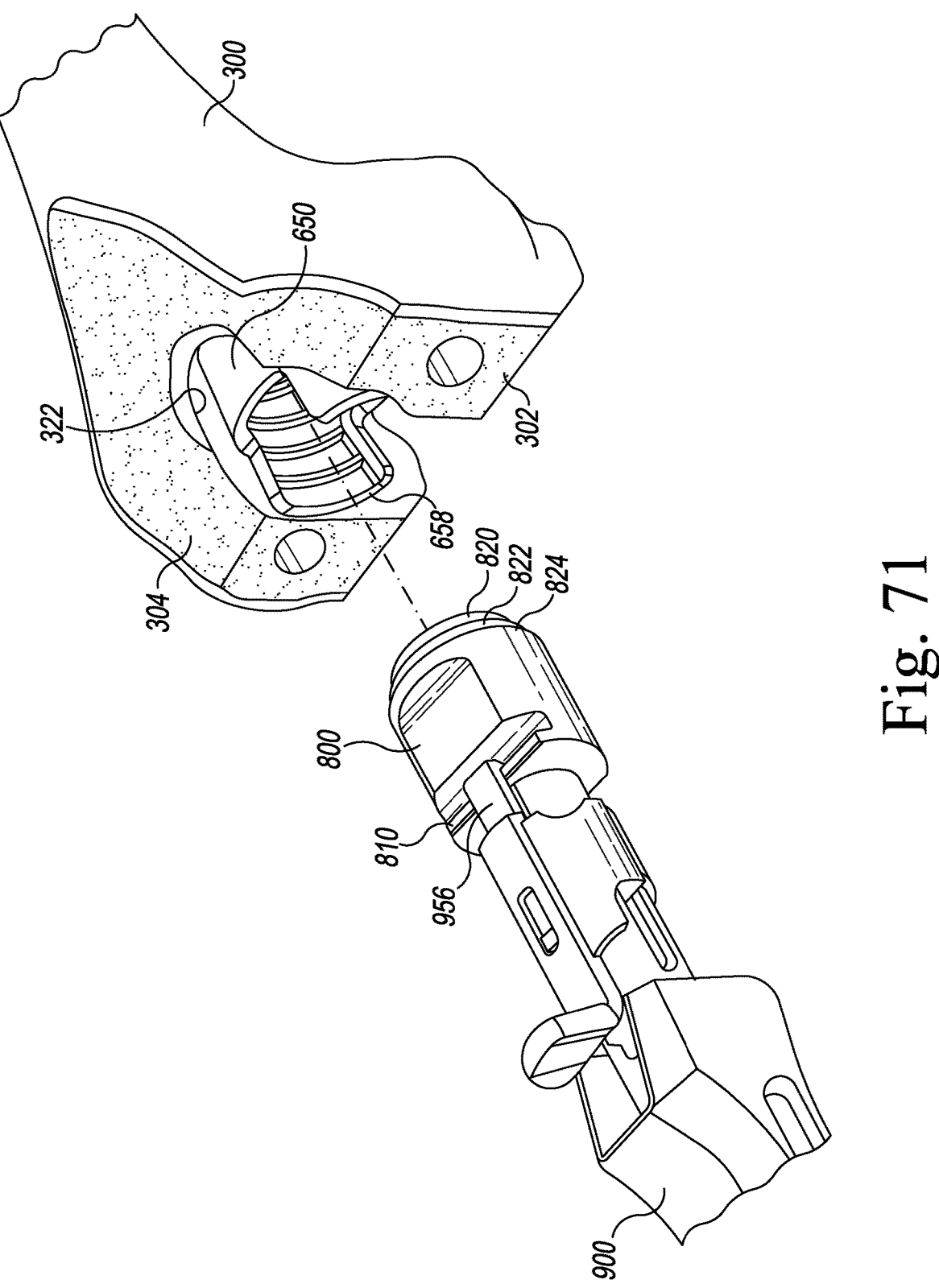
FIG. 71 illustrates the impactor head of FIG. 66 being used in a surgical procedure to implant the concentric cone augment of FIGS. 60-62 into the distal end of the femur of a patient.

As can be seen in FIGS. 70 and 71, the impactor head 800 may be used during installation of the concentric cone augment 650 in a revision procedure in which a primary tibial implant has been removed from the proximal end 202 of the patient's tibia 200 (FIG. 70) or in which a primary femoral implant has been removed from the distal end 302 of the patient's femur 300 (FIG. 71). The impactor head 800 may also be used to install the concentric cone trial component 700 during such a revision procedure. Prior to installation of either the concentric cone augment 650 or the concentric cone trial component 700, the cavity 222 to receive the concentric cone augment 650 (or trial component 700) is first surgically-prepared in the proximal end 202 of the patient's tibia 200 (FIG. 70) or the cavity 322 to receive the concentric cone augment 650 (or trial component 700) is first surgically-prepared in the distal end 302 of the patient's femur 300. The method described above in regard to FIGS. 25-31 may be used as a procedure for surgically-preparing the cavity 222 in the proximal end 202 of the patient's tibia 200 and the method described above in regard to FIGS. 32-36 may be used as a procedure for surgically-preparing the cavity 322 in the distal end 302 of the patient's femur 300. However, it should be appreciated that such surgical procedures may include additional, fewer, or alternate steps depending on the state of the patient's bony anatomy and the preferences of the surgeon.

Once the surgically-prepared cavity 222 or the surgically-prepared cavity 322 has been formed in the patient's bone, the surgeon positions a concentric cone augment 650 of the appropriate size in the cavity. Thereafter, the surgeon utilizes the impactor head 800 to impact the concentric cone augment 650. To do so, the surgeon first connects an impactor head 800 to the impaction handle 950. To do so, the impaction handle's connecting pin 952 (see FIG. 83) is inserted in the D-shaped socket 808 of the impactor head 800 and thereafter advanced downwardly. The connector lip 810 of the impactor head 800 is then engaged by the locking pawl 956 of the impaction handle's connector 954 to secure the impactor head 800 to the impaction handle 950.

The surgeon then utilizes the impaction handle 950 to advance the distal end of the impactor head 800 into the bore 658 of the concentric cone augment 650 positioned in the patient's bone. In doing so, the lead-in flange 820 of the impactor head 800 is advanced into the concentric cone augment's bore 658. Depending on the size of the concentric cone augment 650 being installed, the impact flange 822 either comes to rest on the augment's annular rim 668 or is also advanced with the lead-in flange 820 into the augment's bore 658 (in the case of a larger augment) in which case the impact flange 824 comes to rest on the augment's annular rim 668. In either case, once the impactor head 800 is seated, one of the impact flanges 822, 824 is positioned in contact with the augment's annular rim 668.

The surgeon then holds the impaction handle 950 via the grip 960 defined in its elongated body (see FIG. 83) and strikes the upper surface 962 of handle's metal strike plate 964 (see FIG. 83) with a surgical mallet, sledge, or other impaction tool. In doing so, impaction forces are transferred from the impact flange 822 or the impact flange 824 (depending which one is in contact with the augment's annular rim 668 based on the size of the augment) to the augment's annular rim 668 thereby driving the concentric cone augment 650 into the bone tissue.

Once the surgeon has implanted the concentric cone augment 650, the surgeon may then implant a revision prosthesis by installing its stem component through the concentric cone augment 650 and thereafter cementing it in place within the bone.

It should be appreciated that during such a procedure to implant the concentric cone augment 650, the surgeon may elect to use one or more of the concentric cone trial components 700 as part of an intraoperative trialing procedure. As shown in FIGS. 74 and 75 and discussed above, the impactor head 800 may also be used to install the concentric cone trial component 700. Specifically, in a similar manner to as described above in regard to implantation of the concentric cone augment 650, the surgeon may utilize the impaction handle 950 to advance the distal end of the impactor head 800 into the bore 718 of the concentric cone trial component 700 once the trial component has been positioned in the surgically-prepared cavity formed in the patient's bone. As the impactor head 800 is advanced into the trial component's bore 718, the lead-in flange 820 of the impactor head 800 is advanced into the concentric cone trial component's bore 718. Depending on the size of the concentric cone trial component 700 being installed, the impact flange 822 either comes to rest on the trial component's annular rim 728 or is also advanced with the lead-in flange 820 into the trial component's bore 718 (in the case of a larger trial component) in which case the impact flange 824 comes to rest on the trial component's annular rim 728. In either case, once the impactor head 800 is seated, one of the impact flanges 822, 824 is positioned in contact with the trial component's annular rim 728.

The surgeon then holds the impaction handle 950 via the grip 960 defined in its elongated body (see FIG. 83) and strikes the upper surface 962 of handle's metal strike plate 964 (see FIG. 83) with a surgical mallet, sledge, or other impaction tool. In doing so, impaction forces are transferred from the impact flange 822 or the impact flange 824 (depending which one is in contact with the trial component's annular rim 728 based on the size of the trial component) to the trial component's annular rim 728 thereby driving the concentric cone trial component 700 into the bone tissue.

Once the concentric cone trial component 700 has been installed in such a manner, the surgeon may use it along with other trial components in the performance of an intraoperative trialing procedure. Once the surgeon is satisfied with the outcome of the trialing procedure, the concentric cone trial component 700 is removed from the patient's knee (in a manner discussed below) and the concentric cone augment 650 implanted in the manner described above.

It should also be appreciated that other types of augments and trial components may also be embodied used in combination with an impactor head having corresponding concentric impaction flanges. In particular, although the concepts of FIGS. 60-75 have herein been described in the context of a concentric cone augment 650 (and associated trial component 700), the concepts of FIGS. 60-75 could also be incorporated into a bi-lobe or tri-lobe tibial cone augment (and associated trial components) or a femoral cone augment (and associated trial components).

Figures 76, 77, 78:
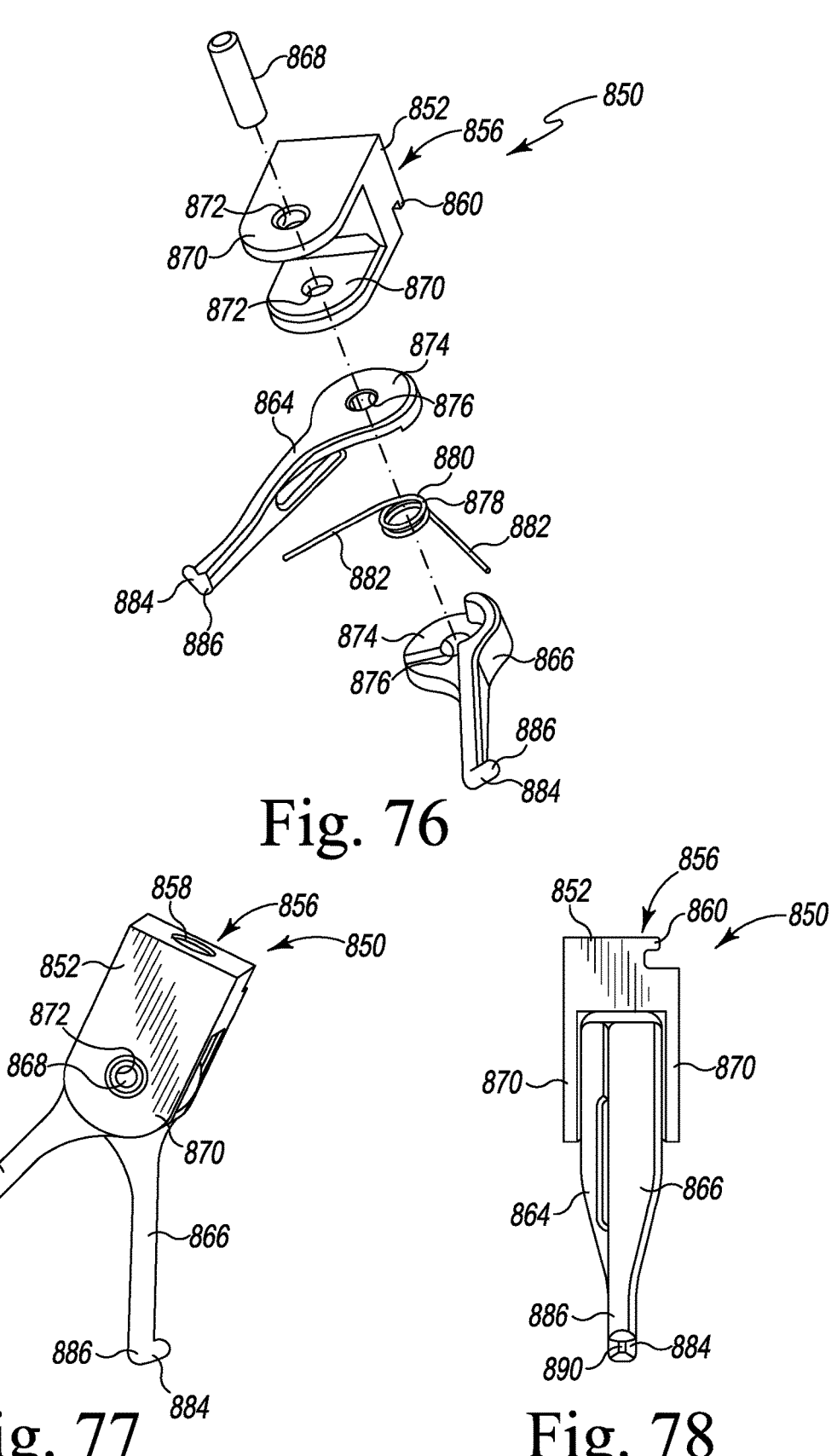
FIG. 76 is an exploded perspective view of a trial extractor.
FIG. 77 is an assembled perspective view of the trial extractor of FIG. 76.
FIG. 78 is a side elevation view of the trial extractor of FIG. 76.

Referring now to FIGS. 76-78, there is shown another orthopaedic surgical instrument of the orthopaedic joint replacement system 10. Specifically, there is shown a trial extractor 850 that is operable to extract knee cone trial components from the knee of a patient subsequent to use of the trial components in an intraoperative trialing procedure. For example, the trial extractor 850 may be used to extract the femoral cone trial component 512 (see FIGS. 46-49) from the surgically-prepared cavity 322 formed in the distal end 302 of the patient's femur 300. The trial extractor 850 may also be used to extract a tibial cone trial component 912 (see FIGS. 80-82) from the surgically-prepared cavity 222 formed in the proximal end 202 of the patient's tibia 200. Likewise, the trial extractor 850 may be used to extract the concentric cone trial component 700 (see FIGS. 63-65) from either surgically-prepared cavity 222, 322.

The trial extractor 850 includes a connector body 852 that is configured to be secured to a removable impaction handle. In the illustrative embodiment described herein, the connector body 852 includes a connector 856 for connecting the trial extractor 850 to the impaction handle 950 (see FIG. 83). It should be appreciated; however, that in other embodiments the connector body 852 may also be secured to an integrated, non-removable impaction handle. The connector 856 includes a D-shaped socket 858 formed in the proximal surface 854 of the trial extractor 850. The D-shaped socket 858 is sized, shaped, and positioned to receive the D-shaped connecting pin 952 of the connector 954 of the impaction handle 950 (see FIG. 83). The connector 856 of the trial extractor 850 also includes a connector lip 860. When the impaction handle's connecting pin 952 is inserted in the D-shaped socket 858 of the trial extractor 850 and thereafter advanced downwardly, the connector lip 860 is engaged by a locking pawl 956 of the impaction handle's connector 954 (see FIG. 79) to secure the trial extractor 850 to the impaction handle 950.

The trial extractor 850 also includes a pair of extractor arms 864, 866. The extractor arms 864, 866 are pivotally coupled to the connector body 852 by a pivot pin 868. Specifically, as can be seen in FIG. 76, the connector body 852 is a generally U-shaped structure defined in part by pair of mounting flanges 870 that are spaced apart from one another. Each of the mounting flanges 870 has an aperture 872 defined therein. Likewise, the proximal end 874 of each of the extractor arms 864, 866 has an aperture 876 defined therein. The pivot pin 868 is positioned in the apertures 872 of the connector body's mounting flanges 870 and the apertures 876 of the extractor arms 864, 866 so as to pivotally couple the arms 864, 866 to the mounting flanges 870.

As can be seen in FIG. 76, the trial extractor 850 also includes a spring 878 that asserts a spring bias on the extractor arms 864, 866 so as to urge the arms 864, 866 away from one another. In the illustrative embodiment described herein, the spring 878 is embodied as a torsion spring having a loop 880 with a pair of spring arms 882 extending away from the loop 880. As can be seen in FIG. 76, the pivot pin 868 extends through the loop 880 of the torsion spring 878 so as to capture the spring. One of the spring's arms 882 is biased against the extractor arm 864, with the other spring arm 882 being biased the extractor arm 866. In such a way, the spring arms 882 urge the extractor arms 864, 866 away from one another.

Each of the extractor arms 864, 866 has a prong 884 formed in its distal end 886. The prongs 884 are sized and shaped to be received into an extraction opening 888 formed in a knee cone trial component such as the femoral cone trial component 512 (see FIGS. 46-49), the tibial cone trial component 912 (see FIGS. 80-82), and the concentric cone trial component 700 (see FIGS. 63-65). In the illustrative embodiment described herein, each of the extraction openings 888 is diamond shaped, with each of the prongs 884 defining a pointed tip 890 (see FIG. 78) which is received into the diamond shaped extraction openings 888 of the trial components. However, it should be appreciated that the extraction openings 888 and the corresponding pointed tips 890 of the prongs 884 may have other shapes to fit the needs of a given instrument design.

Each of the trial components includes at least one pair of the extraction openings 888 positioned on opposite sides of the trial component from one another so as to accommodate the prongs 884 formed on the extractor arms 864, 866. For example, as shown in FIGS. 46-49, the femoral cone trial component 512 includes a pair of extraction openings 888 that extend between the inner sidewall 536 of the trial component and its outer sidewall 538, with one of such extraction openings 888 being positioned on the medial side of the trial component's hollow body 516 and the other extraction opening 888 being positioned on its opposite, lateral side. Further, as shown in 80-82, the tibial cone trial component 912 includes two pairs of extraction openings 888. As can be seen best in FIGS. 80 and 81, each of the extraction openings 888 extends between the inner sidewall 936 of the trial component and its outer sidewall 938. As can be seen best in FIG. 81, one pair of the extraction openings 888 is positioned on the medial and lateral sides of the tibial cone trial component 912, with the other pair being positioned on the anterior and posterior sides of the trial component. As shown in FIGS. 63-65, the concentric cone trial component 700 has multiple pairs of extraction openings 888 formed therein, with each of such extraction openings extending between the inner sidewall 722 and the outer sidewall 724 of the trial component's hollow body 716. As can be seen best in FIG. 64, one pair of the extraction openings 888 is positioned on the medial and lateral sides of the trial component 700, with the other pair being positioned on the anterior and posterior sides of the trial component.

Figure 79:
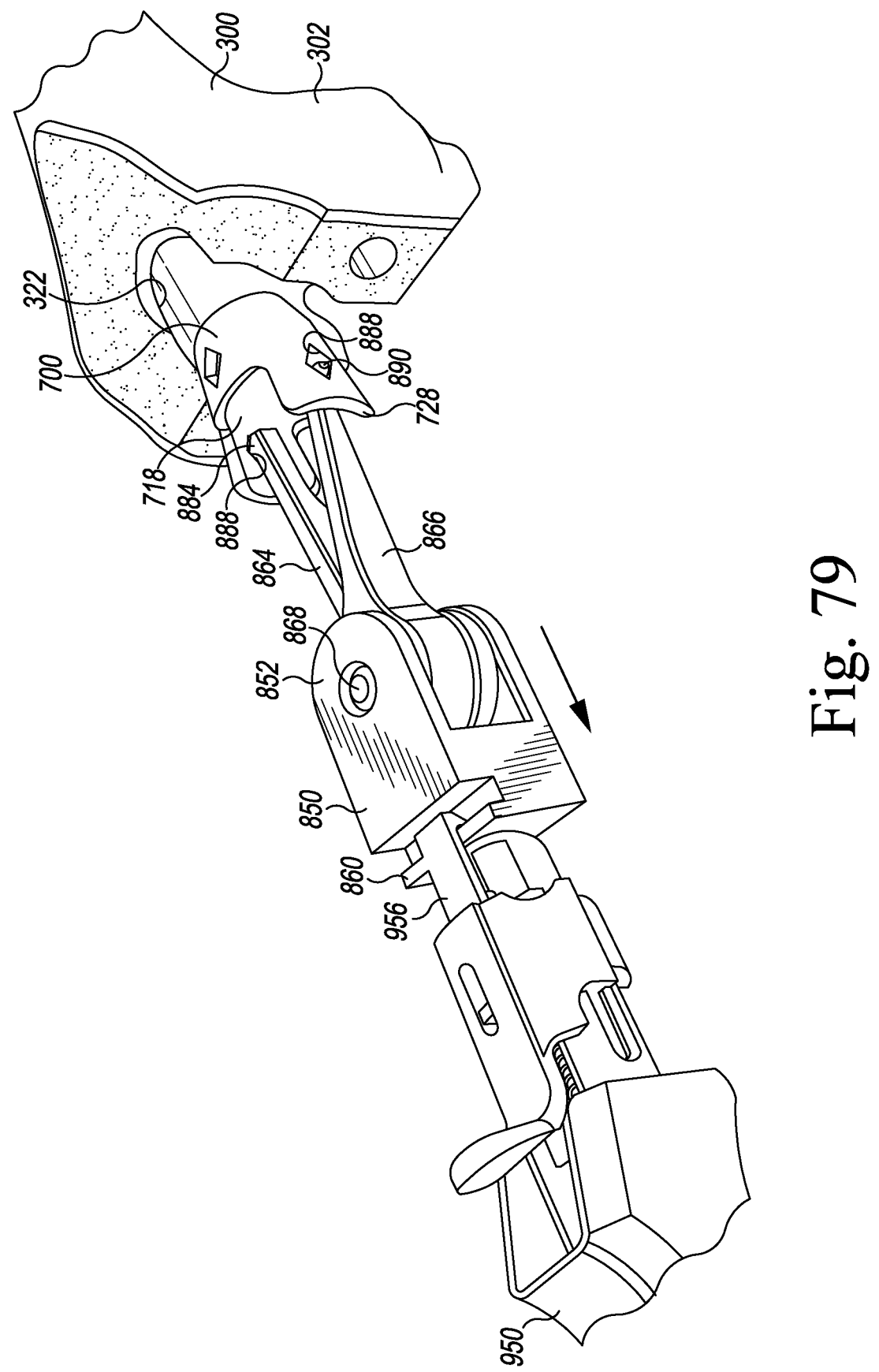
FIG. 79 illustrates the trial extractor of FIG. 76 being used in a surgical procedure to extract the concentric cone trial component of FIGS. 63-65 from the distal end of the femur of a patient.

Referring now to FIG. 79, use of the trial extractor 850 will be illustratively described in the context of the removal of the concentric cone trial component 700 from the distal end 302 of the patient's femur 300 in a revision procedure in which a primary femoral implant has been previously removed from the patient's femur 300. However, it should be appreciated that the trial extractor 850 may be used in a similar manner to as described in regard to FIG. 79 to remove the concentric cone trial component 700 from the proximal end 202 of the patient's tibia 200. The trial extractor 850 may also be used in a similar manner to as described in regard to FIG. 79 to remove the femoral trial component 512 from the distal end 302 of the patient's femur 300 or the tibial cone trial component 912 from the proximal end 202 of the patient's tibia 200.

The cavity 322 to receive the concentric cone trial component 700 is first surgically-prepared in the distal end 302 of the patient's femur 300. The method described above in regard to FIGS. 32-36 may be used as a procedure for surgically-preparing the distal end 302 of the patient's femur 300 in such a manner. However, it should be appreciated that such a surgical procedure may include additional, fewer, or alternate steps depending on the state of the patient's bony anatomy and the preferences of the surgeon.

Once the surgically-prepared cavity 322 has been formed in the distal end 302 of the patient's femur 300, the surgeon positions and installs a concentric cone trial component 700 of the appropriate size in the cavity 322. The surgeon may utilize the impactor head 800 to impact the concentric cone trial component 700 during such installation or may opt for additional, fewer, or alternate steps in installing the trial component 700 depending on the state of the patient's bony anatomy and the preferences of the surgeon.

Once the concentric cone trial component 700 has been installed in the patient's femur 300, the surgeon may use it along with other trial components in the performance of an intraoperative trialing procedure. In doing so, the surgeon moves the patient's knee through a trial range of motion to assess the fit and alignment of the installed trial components.

Once the surgeon is satisfied with the outcome of the trialing procedure, the concentric cone trial component 700 is removed from the patient's femur 300 by use of the trial extractor 850. To do so, the surgeon first connects the trial extractor 850 to the impaction handle 950. Specifically, the impaction handle's connecting pin 952 (see FIG. 83) is inserted in the D-shaped socket 858 of the trial extractor 850 and thereafter advanced downwardly such that the connector lip 860 of the trial extractor 850 is engaged by the locking pawl 956 of the impaction handle's connector 954 to secure the trial extractor 850 to the impaction handle 950.

The surgeon then utilizes the impaction handle 950 to advance the distal ends 886 of the instrument's extractor arms 864, 866 into the bore 718 of the concentric cone trial component 700 installed in the distal end 302 of the patient's femur 300. During such advancement, the surgeon squeezes the extractor arms 864, 866 to overcome the spring bias of the torsion spring 878 thereby urging the prongs 884 toward one another so as to allow the prongs 884 to clear the trial component's annular rim 728 and enter its bore 718. Once the prongs 884 are positioned in the trial component's bore 718, the surgeon aligns them with one of the pairs of extraction openings 888. In the illustrative embodiment of FIG. 79, the surgeon has aligned the prongs 884 with the extraction openings 888 on the medial and lateral sides of the trial component 700, although the pair of extraction openings 888 positioned on the anterior and posterior sides of the trial component 700 may also be used in lieu thereof.

Once the prongs 884 have been aligned with the desired pair of extraction openings 888, the surgeon gently releases the extractor arms 864, 866 thereby allowing the spring bias of the torsion spring 878 to urge the prongs 884 away from one another and into the extraction openings 888. Specifically, in the illustrative example of FIG. 79, one of the prongs 884 is captured in the extraction opening 888 on the medial side of the concentric cone trial component 700 and the other prong 884 is captured in the extraction opening 888 on the lateral side of the trial component 700.

The surgeon then holds the impaction handle 950 via the grip 960 defined in its elongated body (see FIG. 83) and strikes the lower surface 966 of handle's metal strike plate 964 (see FIG. 83) with a surgical mallet, sledge, or other impaction tool. In doing so, extraction forces are transferred from the extractor arms 864, 866 of the trial extractor 850 to the concentric cone trial component 700 thereby urging the trial component 700 out of the bone tissue of the surgically-prepared cavity 322 formed in the distal end 302 of the patient's femur 300.

Once the concentric cone trial component 700 is removed from the patient's femur 300, the surgeon may then install the concentric cone augment 650 in its place in the manner described above and thereafter implant a revision femoral prosthesis by installing its stem component through the concentric cone augment 650 and thereafter cementing it in place within the bone.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic knee implant, comprising:
   a femoral cone augment configured to be implanted into a surgically-prepared cavity in a distal end of a femur of the patient's knee, the femoral cone augment comprising:
   a round elongated body having a superior end and an inferior end,
   a bore configured to receive a stem of a revision knee prosthesis extending through the elongated body, the bore being defined by a conically-shaped inner sidewall extending through the elongated body between its superior end and its inferior end,
   a medial impact lug and a lateral impact lug secured to the inner sidewall at a location between the superior end and the inferior end of the elongated body, wherein (i) the medial impact lug extends inwardly from a medial-most surface of the inner sidewall toward a central axis of the bore and has a flat, inferior-most impact surface, and (ii) the lateral impact lug extends inwardly from a lateral-most surface of the inner sidewall toward the central axis of the bore and has a flat, inferior-most impact surface, and a box cutout formed in a posterior side of the elongated body, the box cutout is configured to receive a box of a revision femoral prosthesis, wherein (i) the box cutout is defined in part by a flat, inferior-facing surface, and (ii) the impact surface of each of the medial and lateral impact lugs is coplanar with the flat, inferior-facing surface of the box cutout.

2. The orthopaedic knee implant of claim 1, wherein each of the medial and lateral impact lugs includes a curved outer body extending superiorly from the impact surface.

3. The orthopaedic knee implant of claim 2, wherein the curved outer body of each of the medial and lateral impact lugs is tapered in the superior/inferior direction such that a superior end thereof blends into the inner sidewall.

4. The orthopaedic knee implant of claim 1, wherein the impact surfaces of each of the medial and lateral impact lugs are coplanar with one another.

5. The orthopaedic knee implant of claim 1, wherein the inner sidewall has a number cement pockets formed therein.

6. An orthopaedic knee implant, comprising:

a femoral cone augment configured to be implanted into a surgically-prepared cavity in a distal end of a femur of a patient's knee, the femoral cone augment comprising:

a round elongated body having a superior end and an inferior end, a bore configured to receive a stem of a revision femoral prosthesis extending through the elongated body, the bore being defined by a conically-shaped inner sidewall extending through the elongated body between its superior end and its inferior end, a box cutout formed in a posterior side of the femoral cone augment, wherein the box cutout is configured to receive a box of the revision femoral prosthesis and is defined in part by a flat, inferior-facing surface, and a pair of impact lugs secured to the inner sidewall at a location between the superior end and the inferior end of the elongated body, wherein both of the pair of impact lugs (i) extend inwardly from the inner sidewall toward a central axis of the bore, and (ii) have a flat, inferior-most impact surface that is coplanar with the flat, inferior-facing surface of the box cutout.

7. The orthopaedic knee implant of claim 6, wherein both of the pair of impact lugs include a curved outer body extending superiorly from the impact surface.

8. The orthopaedic knee implant of claim 7, wherein the curved outer body of both of the pair of impact lugs is tapered in the superior/inferior direction such that a superior end thereof blends into the inner sidewall.

9. The orthopaedic knee implant of claim 6, wherein the pair of impact lugs includes a medial impact lug secured to a medial side of the inner sidewall and a lateral impact lug secured to a lateral side of the inner sidewall.

10. The orthopaedic knee implant of claim 6, wherein the impact surface of each of the number of impact lugs is coplanar with one another.

11. The orthopaedic knee implant of claim 6, wherein the inner sidewall has a number cement pockets formed therein.

* * * * *